(12) United States Patent
Gallo et al.

(10) Patent No.: US 8,012,714 B2
(45) Date of Patent: Sep. 6, 2011

(54) SEQUENCE DIVERSITY GENERATION IN IMMUNOGLOBULINS

(75) Inventors: Michael Gallo, North Vancouver (CA); Jaspal Singh Kang, Surrey (CA); Craig Robin Pigott, Vancouver (CA)

(73) Assignee: Innovative Targeting Solutions, Inc., Burnaby (CA)

(*) Notice: Subject to any disclaimer, the term of this patent is extended or adjusted under 35 U.S.C. 154(b) by 0 days.

(21) Appl. No.: 12/423,594

(22) Filed: Apr. 14, 2009

(65) Prior Publication Data

US 2009/0258392 A1  Oct. 15, 2009

Related U.S. Application Data

(60) Provisional application No. 61/044,795, filed on Apr. 14, 2008.

(51) Int. Cl.
*C12N 15/00* (2006.01)
*C12N 15/11* (2006.01)
*C12N 5/06* (2006.01)
*C12P 21/08* (2006.01)

(52) U.S. Cl. .............. 435/69.6; 435/320.1; 435/326; 536/23.53

(58) Field of Classification Search ............. 435/69.6, 435/320.1, 326; 536/25.53
See application file for complete search history.

(56) References Cited

U.S. PATENT DOCUMENTS

| | | | |
|---|---|---|---|
| 5,159,066 A | 10/1992 | Schatz et al. ............ 536/27 |
| 5,569,825 A | 10/1996 | Lonberg et al. | |
| 5,756,323 A | 5/1998 | Kallenbach et al. | |
| 2004/0156832 A1 | 8/2004 | Jolly | |
| 2006/0263787 A1 | 11/2006 | Evans et al. | |
| 2009/0111126 A1 | 4/2009 | Akamatsu et al. | |

OTHER PUBLICATIONS

Ferrier et al. (International Immunology 1989, 1:66-74).*
Oltz et al. (Mol. Cell Biol. 1993 13:6223-6230).*
Akamatsu et al., "Essential Residues in V(D)J Recombination Signals," The Journal of Immunology, 153:4520-4528, 1994.
Akamatsu et al., "Whole IgG surface display on mammalian cells: Application to isolation of neutralizing chicken monoclonal anti-IL-12 antibodies," Journal of Immunological Methods, 327:40-52, 2007.
Jung et al., "Mechanism and Control of V(D)J Recombination at the Immunoglobulin Heavy Chain Locus," Annu. Rev. Immunol., 24:541-570, 2006.
Kallenbach et al., "Three lymphoid-specific factors account for all junctional diversity characteristic of somatic assembly of T-cell receptor and immunoglobulin genes," Proc. Natl. Acad. Sci. USA, 89:2799-2803, Apr. 1992.
Landau et al., "Increased Frequency of N-Region Insertion in a Murine Pre-B-Cell Line Infected with a Terminal Deoxynucleotidyl Transferase Retroviral Expression Vector," Molecular and Cellular Biology, 7(9):3237-3243, Sep. 1987.
Nicholson et al., "Antibody Repertoires of Four- and Five-Feature Translocus Mice Carrying Human Immunoglobulin Heavy Chain and κ and λ Light Chain Yeast Artificial Chromosomes," The Journal of Immunology, 163:6898-6906, 1999.
Oltz et al., "A V(D)J Recombinase-Inducible B-Cell Line: Role of Transcriptional Enhancer Elements in Directing V(D)J Recombination," Molecular and Cellular Biology, 13(10):6223-6230, Oct. 1993.
Ramsden et al., "Conservation of sequence in recombination signal sequence spacers," Nucleic Acids Research, 22 (10):1785-1796, 1994.
Schatz, David G., "V(D)J recombination," Immunological Reviews, 200:5-11, 2004.
Alt et al., "Function and Control of Recombination-Activating Gene Activity," Annals New York Academy of Sciences 651(1):277-294, 1992.
Ferrier et al., "T cell receptor DJ but not VDJ rearrangement within a recombination substrate introduced into a pre-B cell line," International Immunology 1(1):66-74, 1989.
Hassanin et al., "Evolution of the recombination signal sequences in Ig heavy-chain variable region locus of mammals," PNAS 97(21):11415-11420, Oct. 10, 2000.
Parham, Peter, "The Immune System," 2nd ed., Garland Science, New York, N.Y., 2005, Chapter 3, p. 68.
Yu et al., "Differential Usage of VH Gene Segments Is Mediated by cis Elements," The Journal of Immunology 161:3444-3454, 1998.
International Search Report and Written Opinion, mailed Feb. 1, 2010, for PCT/US2009/040540, 16 pages.
Blackwell et al., "Recombination between immunoglobulin variable region gene segments is enhanced by transcription," Nature 324:585-589, 1986.
Chakraborty et al., "Repeat Organization and Epigenetic Regulation of the $D_H$-$C_\mu$ Domain of the Immunoglobulin Heavy-Chain Gene Locus," Molecular Cell 27:842-850, 2007.
Cortes et al., "In vitro V(D)J recombination: Signal joint formation," Proc. Natl. Acad. Sci. USA 93:14008-14013, 1996.
Cowell et al., "Computational tools for understanding sequence variability in recombination signals," Immunological Reviews 200:57-69, 2004.
Cuomo et al., "Analysis of regions of RAG-2 important to V(D)J recombination," Nucleic Acids Research 22(10):1810-1814, 1994.
Ferrier et al., "Separate elements control DJ and VDJ rearrangement in a transgenic recombination substrate," The EMBO Journal 9(1):117-125, 1990.
Hesse et al., "V(D)J recombination: a functional definition of the joining signals," Genes & Dev. 3:1053-1061, 1989.

(Continued)

*Primary Examiner* — Lynn Bristol
(74) *Attorney, Agent, or Firm* — Quarles & Brady LLP; Sara D. Vinarov

(57) ABSTRACT

Compositions and methods are disclosed for generating immunoglobulin structural diversity in vitro, and in particular, for reducing biases in V region and J segment gene utilization, and for generating immunoglobulin V-D-J recombination events in a manner that does not require D-J recombination to precede V-DJ recombination. Selection of advantageous combinations of immunoglobulin gene elements, including introduction of artificial diversity (D) segment genes and optimization of recombination signal sequence (RSS) efficiency, are disclosed.

44 Claims, 12 Drawing Sheets

OTHER PUBLICATIONS

Huse et al., "Generation of a Large Combinatorial Library of the Immunoglobulin Repertoire in Phage Lambda," *Science* 246:1275-1281, 1989.

Inlay et al., Critical roles of the immunoglobulin intronic enhancers in maintaining the sequential rearrangement of *IgH* and *Igk* lodi, *JEM* 203(7):1721-1732, 2006.

Kallenbach et al., "A rapid test for V(D)J recombinase activity," *Nucleic Acids Research* 18(22):6730, 1990.

Lee et al., "A Functional Analysis of the Spacer of V(D)J Recombination Signal Sequences," *PLoS Biology* 1(1):056-069, 2003.

Lieber et al., "Developmental stage specificity of the lymphoid V(D)J recombination activity," *Genes & Development* 1:751-761, 1987.

Maës et al., "Activation of V(D)J Recombination at the IgH Chain JH Locus Occurs within a 6-Kilobase Chromatin Domain and Is Associated with Nucleosomal Remodeling," *J Immunol* 176:5409-5417, 2006.

Nadel et al., "Sequence of the Spacer in the Recombination Signal Sequence Affects V(D)J Rearrangement Frequency and Correlates with Nonrandom Vκ Usage In Vivo," *J. Exp. Med.* 187(9):1495-1503, 1998.

Repasky et al., "Mutational Analysis of Terminal Deoxynucleotidyltransferase-Mediated N-Nucleotide Addition in V(D)J Recombination," *J. Immunol.* 172:5478-5488, 2004.

Roch et al., "V(D)J recombination frequency is affected by the sequence interposed between a pair of recombination signals: sequence comparison reveals a putative recombinational enhancer element," *Nucleic Acids Research* 25(12):2303-2310, 1997.

Sadofsky et al., "Expression and V(D)J recombination activity of mutated RAG-1 proteins," *Nucleic Acids Research* 21(24):5644-5650, 1993.

Silver et al., "Dispensable sequence motifs in the RAG-1 and RAG-2 genes for plasmid V(D)J recombination," *Proc. Natl. Acad. Sci. USA* 90:6100-6104, 1993.

Spicuglia et al., "Regulation of V(D)J recombination," *Current Opinion in Immunology* 18:158-163, 2006.

Williams et al., "Unequal $V_H$ Gene Rearrangement Frequency Within the Large $V_H$7183 Gene Family Is Not Due to Recombination Signal Sequence Variation, and Mapping of the Genes Shows a Bias of Rearrangement Based on Chromosomal Location," *J Immunol* 167:257-263, 2001.

* cited by examiner

SEQUENCE DIVERSITY GENERATION IN IMMUNOGLOBULINS

CROSS-REFERENCE TO RELATED APPLICATION

This application claims the benefit under 35 U.S.C. §119 (e) of U.S. Provisional Patent Application No. 61/044,795 filed Apr. 14, 2008. This provisional application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 520056_403_SEQUENCE_LISTING.txt. The text file is 3838 KB, was created on Apr. 14, 2009, and is being submitted electronically via EFS-Web.

BACKGROUND

1. Technical Field

The present invention relates generally to compositions and methods for use in generating antibodies. In particular, according to the invention embodiments described herein there is provided an in vitro molecular biological approach to generating immunoglobulins and modified immunoglobulins having structurally diverse variable regions and other advantageous properties.

2. Description of the Related Art

Adaptive immunity in higher organisms is intimately linked to the expression of antigen-specific immunoglobulin (antibodies) and T cell receptor (TCR) genes. Antibody molecules contain two chains (heavy and light), each of which comprises a variable region and a constant region. The variable region is responsible for antigen binding while the constant region imparts effector functions such as complement dependent cytotoxicity (CDC) and antibody-dependent cell-mediated cellular cytotoxicity (ADCC). In addition, the constant region of the IgG molecule contains a FcRn binding domain that is responsible for the extended half-life of antibodies relative to other serum proteins. In order to combat a large array of pathogens, the immune system has evolved the ability to generate vast repertoires of antibody and TCR binding specificities for various antigens. These large repertoires of antibody variable regions are not encoded in the genome, but instead result from the assembly of recombined germlne V (variable), D (diversity) and J (joining) gene segments.

The recombination of different immunoglobulin heavy chain (IgH) V, D, and J gene segments creates a wide repertoire of antibody variable regions having distinct binding specificities for different antigens. Antibody light chains (Kappa and Lambda) are also generated via the same type of recombination process except that the light chain does not have any D gene segments. These recombination events involve the breaking and joining of DNA segments in the genome. In response to antigen, somatic hypermutation (SHM) and class switch recombination (CSR) induce further modifications of immunoglobulin genes in B cells. CSR changes the IgH constant region from IgM to IgG concomitant with the initiation of SHM within the germinal center of secondary immune organs. CSR also provides alternate sets of constant regions with distinct effector functions (e.g., IgG1, IgG2, IgG3, IgG4, IgE and IgA). SHM introduces mutations, at a high rate, into variable region exons, ultimately allowing affinity maturation.

All of these genomic alteration processes require tight regulatory control mechanisms, both to ensure development of a normal immune system and to prevent potentially oncogenic processes, such as translocations, caused by errors in the recombination/mutation processes. The possible negative outcomes of a reaction that initiates double stranded chromosomal breaks include loss of important genetic information, unstable chromosomes, chromosomal translocations, tumorigenesis, or cell death, and it is therefore appreciated that the natural recombination mechanisms that underlie the generation of antibody diversity must be tightly regulated. Such antibody variable region (antigen receptor) gene rearrangement is regulated essentially at four different levels: expression of the RAG1/2 recombinase enzymes that mediate recombination, intrinsic biochemical properties of these recombinases and of the chromosomal cleavage reaction, the post-cleavage/DNA repair stage of the process, and the accessibility of the substrate to the recombinases.

In vitro assays studying the V(D)J recombination reaction were developed using transient substrates as well as integrated substrates in the late 1980s. Using these substrates, the genes for RAG-1 and RAG-2 were identified in 1989 (reviewed in Schatz, 2004 *Immunol Rev* 200:5-11). Since that time a large amount of literature has accumulated on these proteins and the biochemistry of the recombination reaction that gives rise to antibody structural diversity in vivo.

V(D)J Biochemistry

V(D)J recombination occurs at two steps. First, two lymphoid-specific recombinase proteins that are expressed in cells which are capable of immunoglobulin gene rearrangement (e.g., pre-B lymphocytes), RAG-1 and RAG-2, recognize signal sequences and form a synaptic complex with the assistance of HMG1, one of the non-histone chromatin proteins. Then, the RAG proteins cut DNA at the border between the signal sequence and the immunoglobulin polypeptide-coding sequence. At this cleavage step, DNA is nicked first by RAG proteins at the top strand, and then the 3'-hydroxyl group attacks the phosphodiester bond of the bottom strand by a direct nucleophilic reaction, resulting in formation of a hairpin intermediate at the coding end.

The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal"). To begin this lymphoid-specific process, two signals (one 12-signal and one 23-signal) are selected and rearranged under the "12/23 rule"; recombination does not occur between two RSS signals with the same size spacer. In spite of the specificity of the recombinase most of the nucleotide positions within the recombination signals are variable, especially those in the 23 signal. The consensus sequences being accepted as CACAGTG for the heptamer and ACAAAAACC for the nonamer. A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et. al 1994; Akamatsu et. al. 1994; Hesse et. al. 1989). Mutations of other nucleotides have minimal or inconsistent effects. The spacer, although more variable, also has an impact on recombination, and single-nucleotide replacements have been shown to significantly impact recombination efficiency (Fanning et. al. 1996, Larijani et. al 1999; Nadel et. al. 1998). Because of the large amount of sequence variability found at functional RSSs it is difficult to comprehensively evaluate the influence of specific sequences on recombination potential. Recently the Schatz laboratory developed genetic and functional screens to evaluate several thousand 12 spacer RSSs in the context of a consensus heptamer and non-consensus nonamer. They were able to demonstrate that non-consensus spacer nucleotides often impaired recombination (Lee et. al. 2003). It is believed that the spacer might influence recombination at a post-cleavage stage, perhaps during formation of the synaptic complex or coding joint resolution. Differences in the spacer can account for over a 30-fold range in recombination efficiency (Cowell et. al 2004). Studies have shown that the nonamer may be the primary determinant of RSS binding by the recombinase while the heptamer sequence guides cleavage.

The final recombination potential of any single RSS is the combination of all its sequences, which has made predictions difficult. Cowell et al. have generated an algorithm and have identified the optimal sequences for high efficiency recombination. Other in vitro studies have defined the minimal distance required between signal sequences as well as the influence of flanking coding sequences on recombination efficiency. Although it is difficult to predict the efficiency of a RSS by its sequence alone, an algorithm of good predictive potential has been generated and there are empirical data on specific RSSs on the basis of which a skilled person can select RSS polynucleotide sequences that would have significantly different recombination efficiencies (Ramsden et. al 1994; Akamatsu et. al. 1994; Hesse et. al. 1989 and Cowell et. al. 1994).

Following the (RSS) signal-directed DNA cleavage the broken DNA ends are repaired by double-strand break repair proteins. The coding ends are often processed before being repaired, which is an additional step that generates more potential for structural diversity from the reaction. Such processing involves deletion of nucleotides at the coding joint of antigen receptor genes, which is commonly observed at the $V_H$ 3' junction, at both sides (5' and 3') of the D segment, and at the 5' junction of the J segment, followed in some cases by addition of other nucleotides at these processing sites. Terminal deoxynucleotide transferase (TdT) has been identified as a polymerase that plays a role in such nucleotide addition during V(D)J recombination, thus contributing further diversity to the antibody repertoire (Landau et al., *Mol. Cell Biol.* 1987 7:3237). The diversity of the antibody repertoire is therefore the combined result of (i) different gene segment utilization through the recombination events, (ii) optional deletion and/or addition of one or more nucleotides at each of the junctions (e.g., mediation of junctional diversity, such as by TdT), and (iii) differential pairings of the various heavy and light chain combinations that may result from (i) and (ii) in different cells. In vivo the process is highly regulated and once a set of gene segments for a specific antigen receptor is successfully rearranged to generate a functional molecule the gene rearrangement process for additional antigen receptors is prohibited within a given lymphocyte; once successful heavy chain rearrangement is achieved no additional rearrangements take place at that locus. (Inlay et. al. 2006; Alt et. al. 1984)

The human genome has approximately 51 functional immunoglobulin $V_H$ (heavy chain variable), 25 functional D (diversity segments) and 6 $J_H$ (heavy chain joining region) gene segments that can be rearranged into a wide variety of V-D-J combinations and which, when combined with the other mechanisms described above, yield greater than $10^{12}$ unique products.

More specifically, the human immunoglobulin heavy chain repertoire contained on chromosome 14q32.3 has been sequenced and characterized (NCBI locus NG_001019 [SEQ ID NO:110]; vbase, 1997 MRC Centre for Protein Engineering; vbase.mrc-cpe.cam.ac.uk; Kabat E A, Wu T T, Perry H M, Gottesman K S, Foeller C, *Sequences of Proteins of Immunological Interest*, Edition: 5, illustrated, 1992 DIANE Publishing, 1992, Darby, Pa., (ISBN 094137565X, 9780941375658, 2719 pages); Tomlinson et al., 1992 *J Mol Biol* 227:776; Milner et al., 1995 *Ann NY Acad Sci* 764:50). It contains 51 functional VH gene segments and 9 non-rearranged open reading frames. The 51 functional gene segments are represented by 7 families. The VH1 family has 11 related members, VH2 has 3 related members, VH3 has 22 related members, VH4 has 11 related members, VH5 has 2 related members, VH6 and VH7 each are represented by a single family member. The human Ig locus also contains 25 functional D gene segments and 2 non-rearranged open reading frames. The D gene segments are represented by 7 families; D1 has 4 family members, D2 has 4 related family members, D3 has 5 related family members, D4 has 4 related family members, D5 has 4 related family members, D6 has 3 related family members and D7 has a single family member. The human Ig locus also contains 6 J gene segments each representing a unique family member JH1 thru JH6.

The human antibody light chains, kappa and lambda, are found on different chromosomes; 2p11-12 and 22q11.2 respectively. The entire locus for both kappa and lambda has been sequenced; human kappa (NG000833 [SEQ ID NO:111], distal duplicated, and NG000834 [SEQ ID NO:112], IgK proximal) and lambda (NG000002 [SEQ ID NO:113]; NCBI GeneID 3535; IgL@). The human kappa locus contains 40 functional Vkappa gene segments represented by 7 families; VKI has 19 family members, VKII has 9 family members, VKIII has 7 family members, VKIV and VKV are represented by single family members and VKVI has 3 family members. The VKVII family has only one family member and it is non-functional. The kappa locus contains 5 Jkappa gene segments all representing a distinct family JK1 thru JK5. The human lambda locus has a total of 31 functional gene segments represented by 10 families; VL1 has 5 family members, VL2 has 5 family members, VL3 has 9 family members, VL4 and VL5 each of 3 family members, VL7 has 2 family members and VL6, VL8, VL9, VL10 are each represented by a single family member. The lambda locus has seven J gene segment families all represented by a single family member but only 4 are functional and found in human antibody repertoires; these include JL1, JL2, JL3 and JL7. (See, e.g., Kabat et al., *Sequences of Proteins of Immunological Interest*, Edition: 5, 1992 DIANE Publishing, 1992, Darby, Pa., ISBN 094137565X, 9780941375658, 2719 pages.)

RAG-induced double-strand breaks (DSBs) also involve the general nonhomologous end-joining DNA repair pathway or NHEJ. The NHEJ pathway is present in all eukaryotic cells ranging from yeast to humans. The NHEJ pathway is needed to repair these physiologic breaks, as well as challenging pathologic breaks that arise from ionizing radiation and oxidative damage to DNA. Many DNA double strand repair proteins have been demonstrated as directly participating in V(D)J recombination. DNA-dependent protein kinase (DNA-PK) can phosphorylate other repair proteins as well as its own subunits of Ku 70 and Ku 86 (Schatz, 2004 *Immunol Rev* 200:5-11). Recently, another component of the V(D)J recombination mechanism, termed Artemis protein, has been shown to have a role as a nuclease involved in opening hairpin intermediates produced from the V(D)J cleavage. Artemis has dual specific nuclease activities (endonuclease or exonuclease activity). DNA-PK-dependent phosphorylation of Artemis appears to resolve the hairpin intermediates by changing its specificity from that of an exonuclease to an endonuclease. XRCC4 and DNA ligase IV are major double strand break repair proteins also implicated in V(D)J recombination. (Schatz, 2004 *Immunol Rev* 200:5-11; Dai et. al. (2003) *Proc Natl Acad Sci USA* 100:2462-7; Frank et al. (1998) *Nature* 396:173-7; Gellert (2002) *Annu Rev Biochem* 71:101-32; Grawunder et al. (1998) *J Biol Chem* 273:24708-14; Jones et al. J (2001) *Proc Natl Acad Sci USA* 98:12926-31; Modesti et al. (1999) *Embo J* 18:2008-18; Moshous et al. (2000) *Hum Mol Genet.* 9:583-8; Verkaik et al. 2002 *Eur J Immunol* 32:701-9)

RAG-1 has been shown to be evolutionarily highly conserved and homology has been reported in chickens, *Xenopus laevis*, rainbow trout, zebrafish and shark. It has been hypothesized that RAG-1 and RAG-2 may be members of the retroviral integrase superfamily and have been shown to be capable of transposition in vitro. A significant amount of detail is now understood about the RAG-1 and RAG-2 mediated recombination. The two proteins' role is to catalyze the first DNA cleavage steps in V(D)J recombination. RAG-1 has been shown to have inherent single-stranded (ss) DNA cleavage activity, which does not require, but is enhanced by, RAG-2. It has also been demonstrated that the V(D)J recombinase protein RAG-1 undergoes ubiquitinylation in cells. In vitro, the RING finger domain of RAG-1 acts as a ubiquitin ligase that mediates its own ubiquitinylation at a highly conserved K residue in the RAG-1 amino-terminal region. In fact, the N-terminal portion of RAG-1 has been shown to have a distinct enzymatic role separate from the rest of the protein, acting as an E3 ligase.

RAG2 has been shown to directly bind to the core histone proteins. The reaction has also been shown to be cell cycle regulated (Lee et al., 1999 *Immunity* 11:771). Studies on RAG-1 and RAG-2 have also been conducted in vitro with purified proteins. Mutational analyses of RAG-1 or RAG-2 have been performed to identify crucial amino acid residues or regions that might be involved in catalysis or interaction with other proteins during the V(D)J recombination process. The RAG-1 domains or amino acid (aa) residues responsible for the interaction with RAG-2 were not clearly defined although few putative regions for the RAG-2 interaction have been suggested. The core domains of RAG-1 (aa 384-1004) and RAG-2 (aa 1-383) have been previously identified, and these minimal regions of RAG proteins were fully catalytically active in vitro or in vivo. Mutagenesis performed by one group describes a particular mutation in RAG-1 that affects recombination by altering the specificity of target sequence usage. Recombination mediated by wild-type RAG-1 is tolerant of a wide range of coding sequences adjacent to the recombination signal, while the mutant RAG-1 was shown to more limited in the range of RSS that it could use.

Monoclonal antibodies have recently been validated as therapeutic agents. Initial use of mouse monoclonal antibodies in humans resulted in a mouse anti-human antibody (MAHA) response that destroyed the potential therapeutic antibody. The first approach to minimize the anti-mouse response was to generate a chimeric molecule with the mouse variable regions and human constant regions. These molecules still contained significant mouse sequences and a human anti-chimeric antibody (HACA) response was observed. Further attempts have been developed to further reduce the content of mouse sequences and a number of humanization approaches including framework and CDR grafting as examples have been developed.

Another approach was to generate fully human antibodies. Two distinct strategies were developed. The first involves the isolation of "naive" antibody sequences directly from humans. Large libraries have been generated using phage display to capture the human repertoire. These "naive" sequences are generally derived from human IgM cDNA libraries from human B-cells. These libraries are fully human but are in fact not completely "naive" since they have been subjected to in vivo positive and negative selection associated with immune tolerance; they are generally "naive" only to the antigen of interest in that these human IgM antibodies are likely to bind unknown antigens that were present in the human source of the B-cells.

The second strategy was to generate transgenic animals that contain the human Ig cis sequences. The use of transgenic mice results in a human antibody repertoire that is also generated in vivo, albeit in a mouse. Different transgenes have been generated and different methods have been used to introduce those transgenes into the genome of a mouse including: pronuclear injection, YAC integration into embryonic stem (ES) cells, microcell fusion of ES cells or targeted integration of human antibody sequences to the mouse Ig locus of ES cells. Additional groups are exploiting the somatic hypermutation or mutagenesis processes as means to generate fully human antibodies.

These approaches each have specific limitations. While a number of "humanized" antibodies are approved therapeutics, these proteins still contain mouse sequences and are not entirely human. In addition, the "humanization" process can be lengthy and often compromises the binding characteristics of the original antibody. Because of the resources and uncertainties involved with the process, "humanization" is often done only on the lead antibodies and by specialized groups with the expertise. An additional disadvantage of the humanization process is that it starts with a mouse antibody and the mouse CDR3. The mouse has fewer D gene segments than humans. The mouse D gene segments also appear to share significant homology and be therefore may not code for as many different amino acids (Schelonka et Al. (2005) *J Immunol* 175:6624-32). The mouse CDR3 has also been shown to contain fewer "N" nucleotide additions and as a result is shorter in length on average compared to the human CDR. As a result the mouse antibody repertoire is significantly less diverse than the human repertoire, and consequently rare antibodies are more difficult to find.

The use of transgenic animals has been attempted in efforts to address a number of these issues, and provides immunoglobulin variable segment sequences that are completely human. Although the repertoire from these animals is theoretically larger than a normal mouse, among the limitations of the transgenic approach is the fact that the human antibody repertoire is actually greater than the B-cell compartment of a mouse. Hence, although these transgenic systems have the potential for a larger antibody repertoire they are in fact limited by the number of B-cells in a mouse. In addition, generating antibodies to highly homologous proteins (human and mouse) is challenging in both normal and transgenic systems as B-cells are deleted as part of immune tolerance.

Another potential disadvantage of currently available transgenic systems is that antibodies generated from these transgenic animals have been subjected to in vivo selection processes involved in tolerance, such that antibodies that specifically recognize human and mouse proteins or protein domains that have high degrees of homology will often be deleted from the repertoire. Antibodies generated in transgenic animals also include mutations different from the germlne sequence as a result of hypermutation processes. Although these mutations are part of the affinity maturation process, many of them do not contribute to antigen binding, and for therapeutics it is therefore desirable to have these sequences removed in a process called "germlining". In addition, these proprietary transgenic technologies are expensive and are not widely available.

In view of these intrinsic limitations in the existing antibody methodologies, and given the limited access to the current technologies, there is clearly a need for additional strategies for the generation of fully human antibodies, including for therapeutic applications. The presently disclosed invention embodiments address this need and offer other related advantages.

BRIEF SUMMARY

According to certain embodiments of the present invention, there is provided a nucleic acid composition for generating immunoglobulin structural diversity, comprising (a) a first isolated nucleic acid that comprises one or a plurality of mammalian immunoglobulin heavy chain variable ($V_H$) region genes, each having (i) an immunoglobulin $V_H$ region encoding polynucleotide sequence, and (ii) a $V_H$ region recombination signal sequence (RSS) that is located 3' to the immunoglobulin $V_H$ region encoding polynucleotide sequence; (b) a second isolated nucleic acid that comprises one or a plurality of mammalian immunoglobulin heavy chain diversity (D) segment genes, each of said immunoglobulin D segment genes having (i) a D segment encoding polynucleotide sequence, (ii) a D segment upstream recombination signal sequence that is located 5' to each of said D segment encoding polynucleotide sequences and that is capable of functional recombination with the $V_H$ region recombination signal sequence, and (iii) a D segment downstream recombination signal sequence that is located 3' to each of said D segment encoding polynucleotide sequences; (c) a third isolated nucleic acid that comprises one or a plurality of mammalian immunoglobulin heavy chain joining ($J_H$) segment genes, each of said immunoglobulin $J_H$ segment genes having (i) a $J_H$ segment encoding polynucleotide sequence in operable linkage to an immunoglobulin heavy chain constant ($C_H$) region gene, and (ii) a $J_H$ segment recombination signal sequence that is located 5' to the $J_H$ segment encoding polynucleotide sequence and that is capable of functional recombination with the D segment downstream recombination signal sequence of (b); and (d) a fourth isolated nucleic acid that comprises a polynucleotide sequence encoding a membrane anchor domain polypeptide, wherein the nucleic acid composition can undergo at least two or more recombination events in a cell to form a recombined polynucleotide that encodes an immunoglobulin heavy chain polypeptide having a membrane anchor domain.

According to certain embodiments there is provided a nucleic acid composition for generating immunoglobulin structural diversity, comprising: (a) a first isolated nucleic acid that comprises one or a plurality of mammalian immunoglobulin heavy chain variable ($V_H$) region genes, each having (i) an immunoglobulin $V_H$ region encoding polynucleotide sequence, and (ii) a $V_H$ region recombination signal sequence (RSS) that is located 3' to the immunoglobulin $V_H$ region encoding polynucleotide sequence; (b) a second isolated nucleic acid that comprises one or a plurality of mammalian immunoglobulin heavy chain diversity (D) segment genes, each of said immunoglobulin D segment genes having (i) a D segment encoding polynucleotide sequence, (ii) a D segment upstream recombination signal sequence that is located 5' to each of said D segment encoding polynucleotide sequences and that is capable of functional recombination with the $V_H$ region recombination signal sequence, and (iii) a D segment downstream recombination signal sequence that is located 3' to each of said D segment encoding polynucleotide sequences; and (c) a third isolated nucleic acid that comprises one or a plurality of mammalian immunoglobulin heavy chain joining ($J_H$) segment genes, each of said immunoglobulin $J_H$ segment genes having (i) a $J_H$ segment encoding polynucleotide sequence in operable linkage to an immunoglobulin heavy chain constant ($C_H$) region gene, and (ii) a $J_H$ segment recombination signal sequence that is located 5' to the $J_H$ segment encoding polynucleotide sequence and that is capable of functional recombination with the D segment downstream recombination signal sequence of (b); wherein the nucleic acid composition can undergo at least two or more recombination events in a cell to form a recombined polynucleotide that encodes an immunoglobulin heavy chain polypeptide.

In certain further embodiments the nucleic acid composition is selected from (a) the nucleic acid composition in which (i) the mammalian immunoglobulin $V_H$ region genes and the mammalian immunoglobulin heavy chain D segment genes are present at a ratio of about 1:1 to 1:2, and (ii) the mammalian immunoglobulin $J_H$ segment genes and the mammalian immunoglobulin heavy chain D segment genes are present at a ratio of about 1:1 to 1:2; (b) the nucleic acid composition in which the mammalian immunoglobulin $V_H$ region genes and the mammalian immunoglobulin $J_H$ segment genes are present at a ratio of less than or equal to approximately 1:2 (V to J) to 2:1 (V to J); (C) the nucleic acid composition in which (i) the one or a plurality of mammalian immunoglobulin $V_H$ region genes, together with (ii) the one or a plurality of mammalian immunoglobulin $J_H$ segment genes, are not greater in number than the mammalian immunoglobulin heavy chain D segment genes; and (d) the nucleic acid composition in which there are 6, 7, 8, 9, 10, 11 or 12 mammalian immunoglobulin heavy chain D segment genes.

In certain other further embodiments (a) the first isolated nucleic acid comprises 12-50 contiguous $V_H$ region genes of which about 10% to about 30% of said $V_H$ region genes that are contiguous with a 5'-most located VH region gene each comprise a $V_H$ region RSS of low or medium RSS efficiency, and about 70% to about 90% of said $V_H$ region genes that are contiguous with a 3'-most located $V_H$ region gene each comprise a $V_H$ region RSS of high RSS efficiency; and (b) the second isolated nucleic acid comprises a plurality of contiguous D segment genes of which about 80% to about 90% of said D segment genes that are contiguous with a 5'-most located D segment gene each comprises a D segment upstream RSS of high RSS efficiency and a D segment downstream RSS of high RSS efficiency, and about 10% to about 20% of said D segment genes that are contiguous with a 3'-most located D segment gene each comprises a D segment upstream RSS of low or medium RSS efficiency and a D segment downstream RSS of low or medium RSS efficiency, wherein (i) the plurality of $V_H$ region genes, together with (ii) the one or a plurality of $J_H$ segment genes, are not greater in number than said plurality of D segment genes.

In certain other embodiments the nucleic acid composition is characterized by one or more of: (a) the first isolated nucleic acid comprises 12-50 contiguous $V_H$ region genes of which about 10% to about 30% of said $V_H$ region genes that are contiguous with a 5'-most located VH region gene each comprise a $V_H$ region RSS of low or medium RSS efficiency; (b) the first isolated nucleic acid comprises 12-50 contiguous $V_H$ region genes of which about 70% to about 90% of said $V_H$ region genes that are contiguous with a 3'-most located $V_H$ region gene each comprise a $V_H$ region RSS of high RSS efficiency; (c) the second isolated nucleic acid comprises a plurality of contiguous D segment genes of which about 80% to about 90% of said D segment genes that are contiguous with a 5'-most located D segment gene each comprise a D segment upstream RSS of high RSS efficiency and a D segment downstream RSS of high RSS efficiency; and (d) the second isolated nucleic acid comprises a plurality of contiguous D segment genes of which about 10% to about 20% of said D segment genes that are contiguous with a 3'-most located D segment gene each comprise a D segment upstream RSS of low or medium RSS efficiency and a D segment downstream RSS of low or medium RSS efficiency.

In certain embodiments the nucleic acid composition comprises 1, 2, 3, 4, 5, 6, 7 or 8 vectors. In another embodiment the membrane anchor domain polypeptide comprises a polypeptide that is selected from a transmembrane domain polypeptide, a glycosyl-phosphatidylinositol-linkage polypeptide, a lipid raft-associating polypeptide and a specific protein-protein association domain polypeptide. In certain embodiments the first, second, third and fourth isolated nucleic acids are joined in operable linkage as a single nucleic acid molecule, and in certain embodiments the first, second and third isolated nucleic acids are joined in operable linkage as a single nucleic acid molecule. In certain other embodiments the first, second, third and fourth isolated nucleic acids are each capable of integration into a mammalian host cell chromosome in operable linkage following said two or more recombination events, to form the polynucleotide that encodes the immunoglobulin heavy chain polypeptide having a membrane anchor domain, and in certain embodiments the first, second and third isolated nucleic acids are each capable of integration into a mammalian host cell chromosome in operable linkage following said two or more recombination events, to form the polynucleotide that encodes the immunoglobulin heavy chain polypeptide. In certain embodiments the nucleic acid composition comprises a vector which comprises the first, second, third and fourth isolated nucleic acids joined in operable linkage, and in certain embodiments the nucleic acid composition comprises a vector which comprises the first, second and third isolated nucleic acids joined in operable linkage. In certain embodiments the nucleic acid composition comprises two, three or four vectors each of which comprises at least one of said first, second, third and fourth isolated nucleic acids, wherein each of said vectors is capable of integration into a mammalian host cell chromosome in operable linkage to form the polynucleotide that encodes the immunoglobulin heavy chain polypeptide, or the immunoglobulin heavy chain polypeptide having a membrane anchor domain. In certain further embodiments the vector is selected from a virus, a plasmid, a cosmid, a transposon and an artificial chromosome.

In certain embodiments the mammalian immunoglobulin $V_H$ gene is selected from a human $V_H$ gene, a mouse $V_H$ gene, a rat $V_H$ gene, a rabbit $V_H$ gene, a canine $V_H$ gene, a feline $V_H$ gene, an equine $V_H$ gene, a bovine $V_H$ gene, a monkey $V_H$ gene, a baboon $V_H$ gene, a macaque $V_H$ gene, a chimpanzee $V_H$ gene, a gorilla $V_H$ gene, an orangutan $V_H$ gene, a camel $V_H$ gene, a llama $V_H$ gene, an alpaca $V_H$ gene and an ovine $V_H$ gene.

In certain embodiments the nucleic acid composition is under control of at least one operably linked recombination control element, which in certain further embodiments is an inducible recombination control element, which in certain still further embodiments is tightly regulated.

In certain embodiments there is provided a host cell comprising a mammalian cell that is capable of immunoglobulin gene rearrangement and that comprises a nucleic acid composition as described above. In certain embodiments the mammalian cell is selected from the a human cell, a non-human primate cell, a camelid cell, a hamster cell, a mouse cell, a rat cell, a rabbit cell, a canine cell, a feline cell, an equine cell, a bovine cell and an ovine cell. In certain embodiments the host cell is capable of expressing a mammalian RAG-1 gene, a mammalian RAG-2 gene and a mammalian TdT gene, or biologically active fragments or derivatives of said genes that are capable of mediating immunoglobulin gene rearrangement and junctional diversity. In certain further embodiments, expression of one or more of the mammalian RAG-1 gene, mammalian RAG-2 gene and mammalian TdT gene, or biologically active fragments or derivatives of said genes, is inducible expression.

In another embodiment there is provided a nucleic acid composition for generating immunoglobulin structural diversity, comprising: (a) a first isolated nucleic acid that comprises one or a plurality of mammalian immunoglobulin light chain variable ($V_L$) region genes, each having (i) an immunoglobulin $V_L$ region encoding polynucleotide sequence, and (ii) a $V_L$ region recombination signal sequence that is located 3' to the immunoglobulin $V_L$ region encoding polynucleotide sequence; (b) a second isolated nucleic acid that comprises one or a plurality of mammalian immunoglobulin heavy chain diversity (D) segment genes, each of said immunoglobulin D segment genes having (i) a D segment encoding polynucleotide sequence, (ii) a D segment upstream recombination signal sequence that is located 5' to each of said D segment encoding polynucleotide sequences and that is capable of functional recombination with the $V_L$ region recombination signal sequence, and (iii) a D segment downstream recombination signal sequence that is located 3' to each of said D segment encoding polynucleotide sequences; and (c) a third isolated nucleic acid that comprises one or a plurality of mammalian immunoglobulin light chain joining ($J_L$) segment genes, each of said immunoglobulin $J_L$ segment genes having (i) a $J_L$ segment encoding polynucleotide sequence in operable linkage to an immunoglobulin light chain constant ($C_L$) region gene, and (ii) a $J_L$ segment recombination signal sequence that is located 5' to the $J_L$ segment encoding polynucleotide sequence and that is capable of functional recombination with the D segment downstream recombination signal sequence of (b); wherein the nucleic acid composition can undergo at least two or more recombination events in a cell to form a recombined polynucleotide that encodes a polypeptide having an immunoglobulin $V_L$ region, an immunoglobulin $J_L$ segment, and an immunoglobulin $C_L$ region.

In another embodiment there is provided a nucleic acid composition for generating immunoglobulin structural diversity, comprising: (a) a first isolated nucleic acid that comprises one or a plurality of mammalian immunoglobulin light chain variable ($V_L$) region genes, each having (i) an immunoglobulin $V_L$ region encoding polynucleotide sequence, and (ii) a $V_L$ region recombination signal sequence that is located 3' to the immunoglobulin $V_L$ region encoding polynucleotide sequence; (b) a second isolated nucleic acid that comprises one or a plurality of mammalian immunoglobulin heavy chain diversity (D) segment genes, each of said immunoglobulin D segment genes having (i) a D segment encoding polynucleotide sequence, (ii) a D segment upstream recombination signal sequence that is located 5' to each of said D segment encoding polynucleotide sequences and that is capable of functional recombination with the $V_L$ region recombination signal sequence, and (iii) a D segment downstream recombination signal sequence that is located 3' to each of said D segment encoding polynucleotide sequences; (c) a third isolated nucleic acid that comprises one or a plurality of mammalian immunoglobulin light chain joining ($J_L$) segment genes, each of said immunoglobulin $J_L$ segment genes having (i) a $J_L$ segment encoding polynucleotide sequence in operable linkage to either a specific protein-protein association domain encoding polynucleotide or a membrane anchor domain encoding polynucleotide, and (ii) a $J_L$ segment recombination signal sequence that is located 5' to the $J_L$ segment encoding polynucleotide sequence and that is capable of functional recombination with the D segment downstream recombination signal sequence of (b), wherein the nucleic acid composition can undergo at least two or more recombination events in a cell to form a recombined polynucleotide that encodes a polypeptide having (i) an immunoglobulin $V_L$ region, (ii) an immunoglobulin $J_L$ segment and (iii) either a specific protein-protein association domain or a membrane anchor domain. In certain further embodiments the protein-protein association domain is selected from a mammalian immunoglobulin light chain ($C_L$) constant region, an RGD-containing polypeptide that is capable of integrin binding, a lipid raft-associating polypeptide domain, and a heterodimer-promoting polypeptide domain. In certain further embodiments the mammalian immunoglobulin light chain ($C_L$) constant region is selected from a kappa constant region and a lambda constant region. In certain other further embodiments at least one mammalian immunoglobulin heavy chain diversity (D) segment gene comprises one or a plurality of artificial D gene segments. In certain other further embodiments the recombined polynucleotide encodes a polypeptide having an immunoglobulin heavy chain D segment, which in certain further embodiments comprises an artificial D segment. In certain other related embodiments the first, second, and third isolated nucleic acids are joined in operable linkage as a single nucleic acid molecule. In certain other related embodiments the first, second, and third isolated nucleic acids are each capable of integration into a mammalian host cell chromosome in operable linkage following said two or more recombination events. In certain other embodiments the nucleic acid composition comprises a vector which comprises the first, second, and third isolated nucleic acids joined in operable linkage. In certain other embodiments the nucleic acid composition comprises two, three or four vectors each of which comprises at least one of said first, second and third isolated nucleic acids, wherein each of said vectors is capable of integration into a mammalian host cell chromosome in operable linkage to form the polynucleotide that encodes the polypeptide having an immunoglobulin $V_L$ region, $J_L$ segment and $C_L$ region, or that encodes the polypeptide having (i) an immunoglobulin $V_L$ region, (ii) an immunoglobulin $J_L$ segment and (iii) either a specific protein-protein association domain or a membrane anchor domain. In certain further embodiments the vector is selected from a virus, a plasmid, a cosmid, a transposon and an artificial chromosome.

According to certain embodiments of the above described nucleic acid composition, the mammalian immunoglobulin $V_L$ gene is selected from a human $V_L$ gene, a mouse $V_L$ gene, a rat $V_L$ gene, a rabbit $V_L$ gene, a canine $V_L$ gene, a feline $V_L$ gene, an equine $V_L$ gene, a bovine $V_L$ gene, a monkey $V_L$ gene, a baboon $V_L$ gene, a macaque $V_L$ gene, a chimpanzee $V_L$ gene, a gorilla $V_L$ gene, an orangutan $V_L$ gene, and an ovine $V_L$ gene.

According to certain embodiments the above described nucleic acid composition is under control of at least one operably linked recombination control element, which in certain further embodiments is an inducible recombination control element and which in certain still further embodiments is tightly regulated. According to certain embodiments the above described nucleic acid composition comprises a first nucleic acid that comprises at least one expression control sequence that is located 5' to the one or a plurality of immunoglobulin variable region genes. In certain further embodiments the expression control sequence is selected from a promoter, a regulated promoter, a repressor binding site and an activator binding site. In certain still further embodiments the regulated promoter is selected from a tightly regulated promoter and an inducible promoter.

In another embodiment there is provided a host cell comprising a mammalian cell that is capable of immunoglobulin gene rearrangement and that comprises any one or more of the above described nucleic acid compositions. In certain embodiments the mammalian cell is selected from a human cell, a non-human primate cell, a camelid cell, a hamster cell, a mouse cell, a rat cell, a rabbit cell, a canine cell, a feline cell, an equine cell, a bovine cell and an ovine cell. In certain embodiments the host cell is capable of expressing a mammalian RAG-1 gene, a mammalian RAG-2 gene and a mammalian TdT gene, or biologically active fragments or derivatives of said genes that are capable of mediating immunoglobulin gene rearrangement and junctional diversity. In certain embodiments expression of one or more of the mammalian RAG-1 gene, mammalian RAG-2 gene and mammalian TdT gene, or biologically active fragments or derivatives of said genes, is inducible expression.

In another embodiment of the present invention there is provided a method for generating structural diversity in one or a plurality of immunoglobulin heavy chain variable ($V_H$) region genes, comprising: (a) introducing a nucleic acid composition as described herein that comprises one or a plurality of immunoglobulin heavy chain variable ($V_H$) region genes into a host cell that comprises a mammalian cell that is capable of immunoglobulin gene rearrangement; and (b) maintaining the host cell under conditions and for a time sufficient for the nucleic acid composition to undergo two or more recombination events to form a recombined polynucleotide that encodes an immunoglobulin heavy chain polypeptide, and thereby generating structural diversity in one or a plurality of immunoglobulin $V_H$ region genes. In certain further embodiments (a) the step of introducing comprises introducing the nucleic acid composition described above that can undergo at least two or more recombination events in a cell to form a recombined polynucleotide that encodes an immunoglobulin heavy chain polypeptide having a membrane anchor domain, and (b) the step of maintaining results in formation of a recombined polynucleotide that encodes an immunoglobulin heavy chain polypeptide having a membrane anchor domain.

In another embodiment there is provided a method for generating structural diversity in one or a plurality of immunoglobulin light chain variable ($V_L$) region genes, comprising (a) introducing a nucleic acid composition as described herein that comprises one or a plurality of immunoglobulin light chain variable ($V_L$) region genes into a host cell that comprises a mammalian cell that is capable of immunoglobulin gene rearrangement; and (b) maintaining the host cell under conditions and for a time sufficient for the nucleic acid composition to undergo one, two or more recombination events to form a recombined polynucleotide that encodes a polypeptide which comprises an immunoglobulin light chain polypeptide, and thereby generating structural diversity in one or a plurality of immunoglobulin $V_L$ region genes. In certain related embodiments there is provided a method comprising at least one of the above described methods, wherein the step of introducing comprises introducing at least one nucleic acid composition as described above, under conditions and for a time sufficient for chromosomal integration of the nucleic acid composition, to obtain at least one chromosomally integrated nucleic acid composition. In certain related embodiments there is provided a method according to one or more of the methods described above wherein the step of introducing comprises introducing sequentially and in any order two or more of the above described nucleic acid compositions, under conditions and for a time sufficient for chromosomal integration of the nucleic acid compositions, to obtain at least two chromosomally integrated nucleic acid compositions. In certain further embodiments of those just described, less than one of said recombination events occurs per cell cycle of the host cell. In certain other further embodiments there is provided a method that comprises, subsequent to the step of introducing and prior to the step of maintaining, expanding the host cell to obtain a plurality of host cells that are capable of immunoglobulin gene rearrangement and that comprise the at least one chromosomally integrated nucleic acid composition.

In another embodiment there is provided a method for generating structural diversity in one or a plurality of immunoglobulin variable region genes, comprising: (a) introducing at least one nucleic acid composition as described above into a host cell that comprises a mammalian cell that is capable of immunoglobulin gene rearrangement, under conditions and for a time sufficient for chromosomal integration of the at least one nucleic acid composition, to obtain at least one chromosomally integrated nucleic acid composition; (b) expanding the host cell to obtain a plurality of host cells that are capable of immunoglobulin gene rearrangement and that comprise the at least one chromosomally integrated nucleic acid composition; and (c) maintaining the host cell under conditions and for a time sufficient for the nucleic acid composition to undergo two or more recombination events to form a recombined polynucleotide that encodes an immunoglobulin polypeptide, and thereby generating structural diversity in one or a plurality of immunoglobulin variable region genes. In certain embodiments related to the above described methods, the at least one chromosomally integrated nucleic acid composition is under control of at least one operably linked recombination control element, which in certain further embodiments is an inducible recombination control element, and which in certain still further embodiments is tightly regulated.

In another related embodiment there is provided a method as described above that further comprises, subsequent to the step of introducing and prior to the step of maintaining, expanding the host cell to obtain a plurality of host cells that are capable of immunoglobulin gene rearrangement and that comprise the at least one chromosomally integrated nucleic acid composition, wherein the at least one chromosomally integrated nucleic acid composition is under control of at least one operably linked recombination control element that is an inducible recombination control element, and wherein the step of maintaining comprises contacting the plurality of host cells with a recombination inducer.

In certain embodiments related to the above described methods, the host cell comprises a rearranged immunoglobulin $V_L$ gene. In certain embodiments related to the above described methods, the host cell comprises a rearranged immunoglobulin $V_H$ gene. In certain embodiments related to the above described methods, the host cell that is capable of immunoglobulin gene rearrangement is selected from the group consisting of: (a) a host cell that is capable of dividing without immunoglobulin gene rearrangement occurring; (b) a host cell that can be induced to express one or more recombination control elements selected from a RAG-1 gene and a RAG-2 gene; and (c) a host cell that expresses first and second recombination control elements that comprise, respectively, a RAG-1 gene and a RAG-2 gene, wherein expression of at least one of said recombination control elements can be substantially impaired.

These and other aspects of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

DETAILED DESCRIPTION

Certain embodiments of the invention disclosed herein are based on the surprising discovery that an in vitro system for generating antibody diversity can be constructed using appropriately selected nucleic acid molecules that comprise immunoglobulin V, D, J and C region encoding polynucleotide sequences and recombination signal sequences (RSS). As described herein, by the assembly of such appropriately selected components and their introduction into suitable recombination-competent host cells, previously insurmountable challenges associated with the temporal regulation of V(D)J recombination can be overcome. Despite the identification over 18 years ago of the cis elements and trans factors involved in immunoglobulin gene rearrangement, as described above, an in vitro system for generating large antibody repertoires de novo has not been described prior to the present disclosure.

In particular, according to the present application it is disclosed for the first time that in an in vitro antibody gene recombination system, it is not required that an immunoglobulin D-J gene recombination event precedes a V-to-DJ recombination event in order to generate immunoglobulin sequence diversity.

In addition, the present invention provides, in certain embodiments, compositions and methods that overcome the presumed inefficiencies that would otherwise accompany generation of a productive in-frame V(D)J product using an in vitro system that lacks the regulatory mechanisms that are present in a developing lymphocyte. In the absence of these regulatory systems that exist in vivo there would be extreme biases in segment utilization.

In this regard and without wishing to be bound by theory, the presently disclosed embodiments successfully overcome problems associated with inefficiency in the generation by recombination of productive V-D-J junctions, and biases in the relative utilization of particular V, D and/or J gene segments, when cellular regulatory mechanisms, which govern the temporal steps of first mediating a D-J recombination event prior to a V-(D-J) recombination event, are not present. Such inefficiencies and biases arise due to the need for multiple recombination events having unequal probabilities to take place during immunoglobulin gene rearrangement (and during which intervening sequences that include unused coding regions are deleted) in order for certain V, D and J segments to be utilized, given the disparity in the number of V, D and J genes.

Figure 1A:
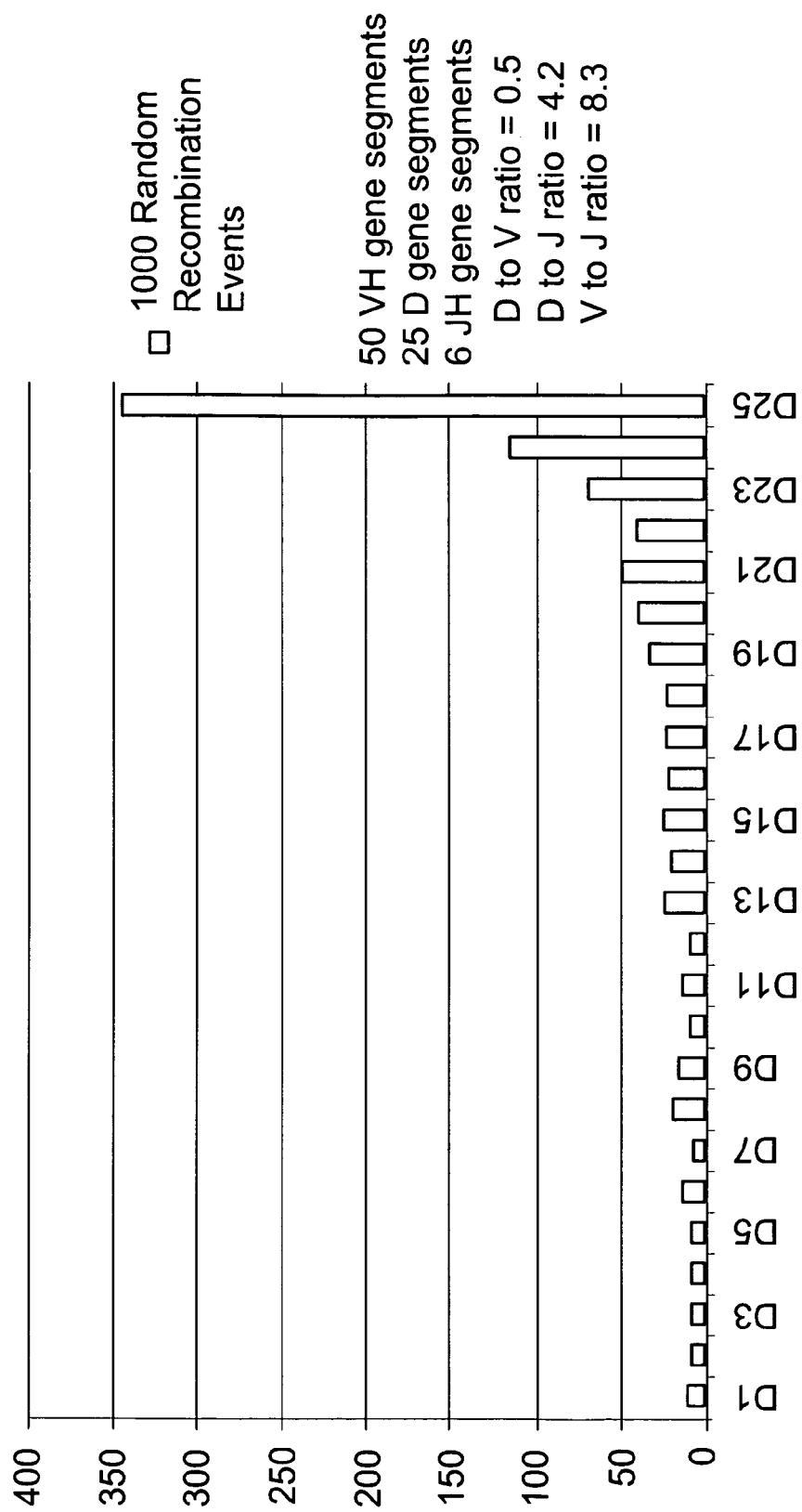
FIG. 1 shows theoretical Ig $V_H$ locus D segment utilization by (FIG. 1A) locus having 50 functional $V_H$, 25 functional D and 6 functional $J_H$ gene segments.
(FIG. 1B) theoretical Ig $V_H$ locus having 21 functional $V_H$, 18 functional D and 6 functional $J_H$ gene segments.
Figure 1B:
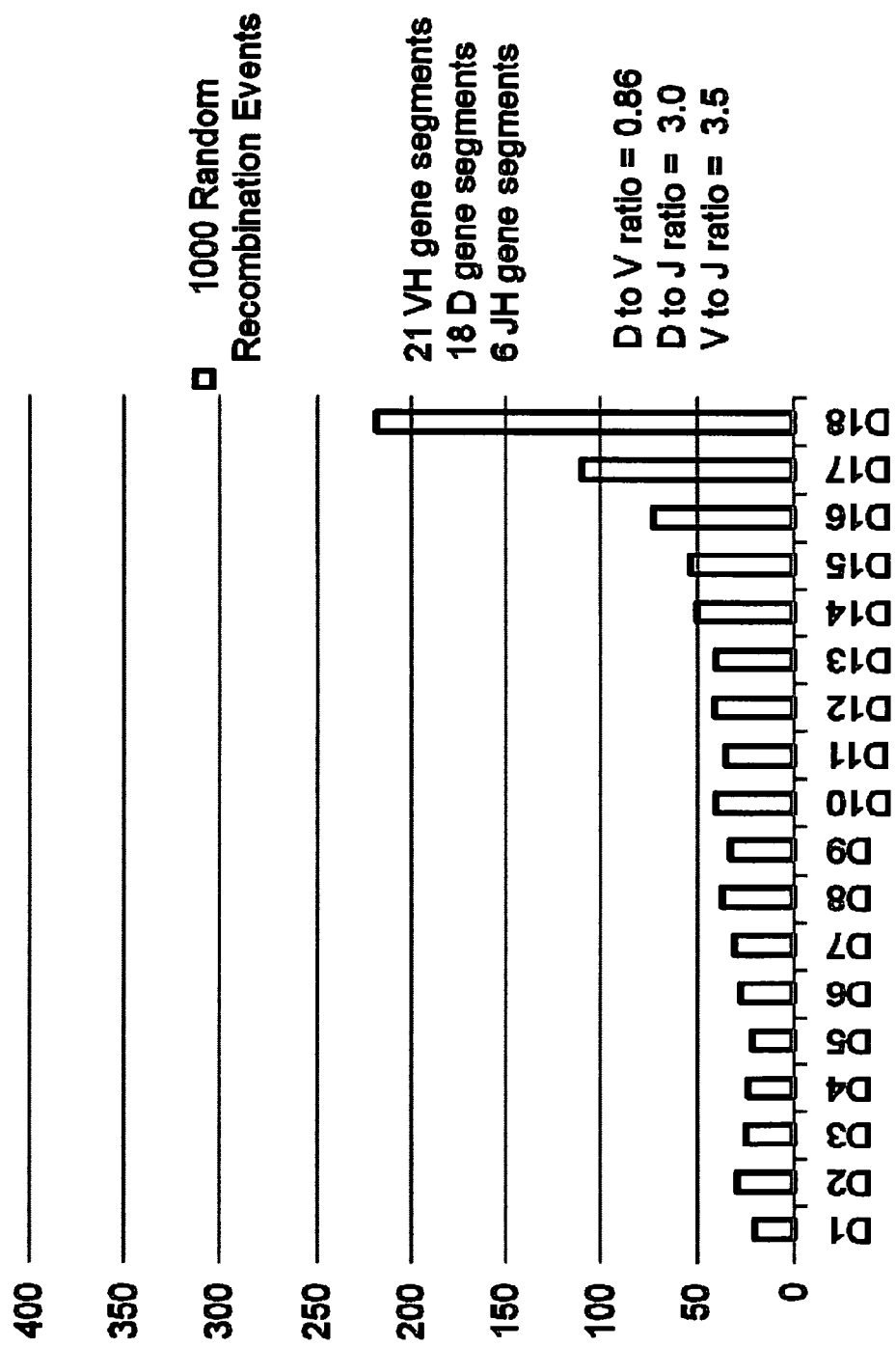

For example, the human Ig $V_H$ locus comprises 51 functional $V_H$, 25 functional D and 6 functional $J_H$ gene segments. As shown in FIG. 1A, 1,000 random V-D-J recombination events (according to a paradigm whereby random V-D events and random D-J events are queried for selection of a common D segment, and whereby equal efficiencies of recombination signal sequences are assumed) within a theoretical Ig $V_H$ locus having 50 functional $V_H$, 25 functional D and 6 functional $J_H$ gene segments, generate an output set having significant disparities in D segment utilization. Further inefficiencies are likely to result from non-productive recombination events. Inversional recombination events will also impact the efficiency of the reaction but do not have a significant impact on segment utilization since gene segment sequences are inverted and not lost. As shown in FIG. 1B, even by reducing the complexity of the theoretical Ig $V_H$ locus to one having 21 functional $V_H$, 18 functional D and 6 functional $J_H$ gene segments, gross disparities in D segment utilization persist.

Figure 2A:
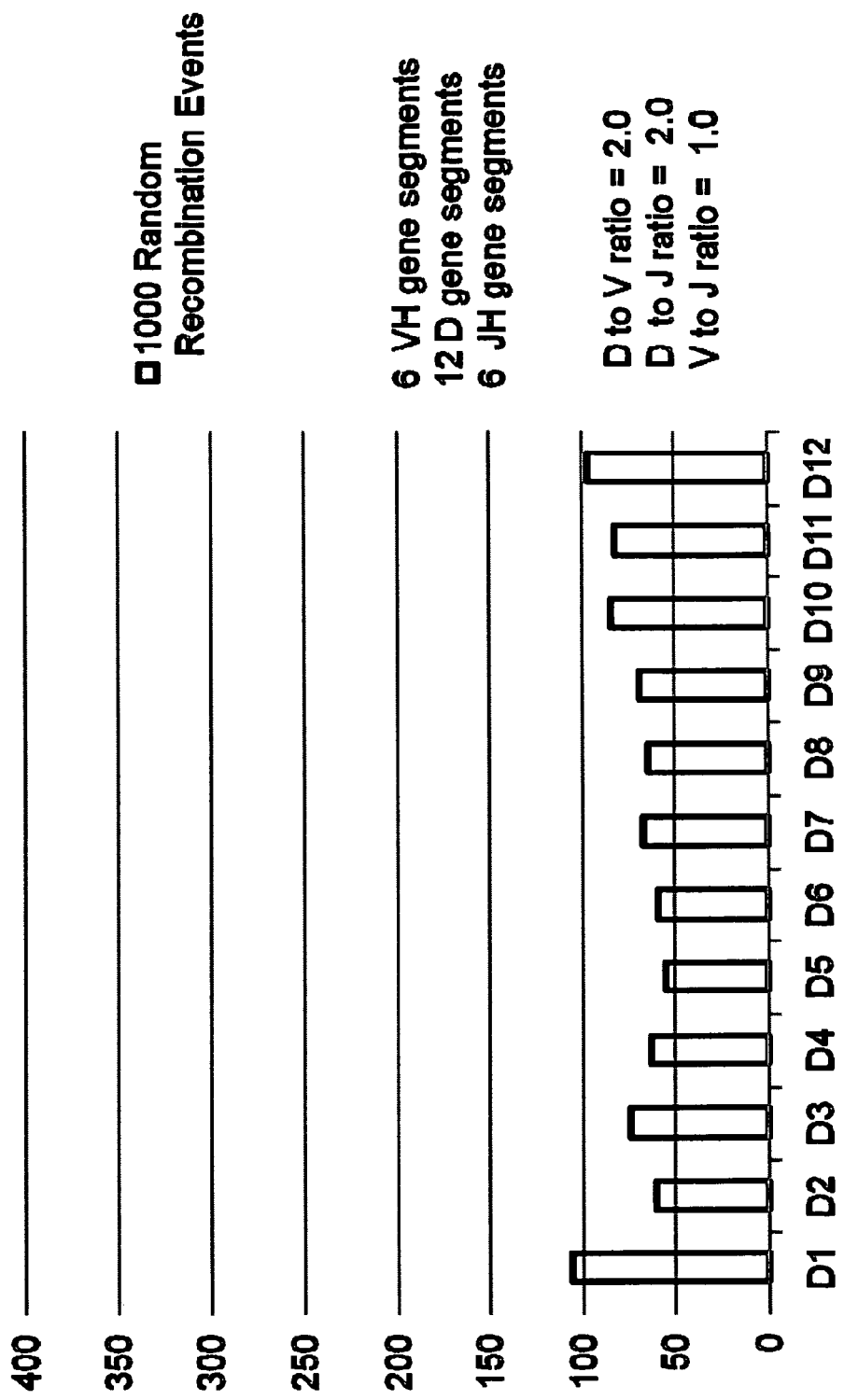
FIG. 2 shows theoretical Ig $V_H$ locus D segment utilization by (FIG. 2A) locus having 6 functional $V_H$, 12 functional D and 6 functional $J_H$ gene segments.
(FIG. 2B) theoretical Ig $V_H$ locus having 12 functional $V_H$, 12 functional D and 12 functional $J_H$ gene segments.
(FIG. 2C) theoretical Ig $V_H$ locus having 13 functional $V_H$, 10 functional D and 9 functional $J_H$ gene segments.
Figure 2B:
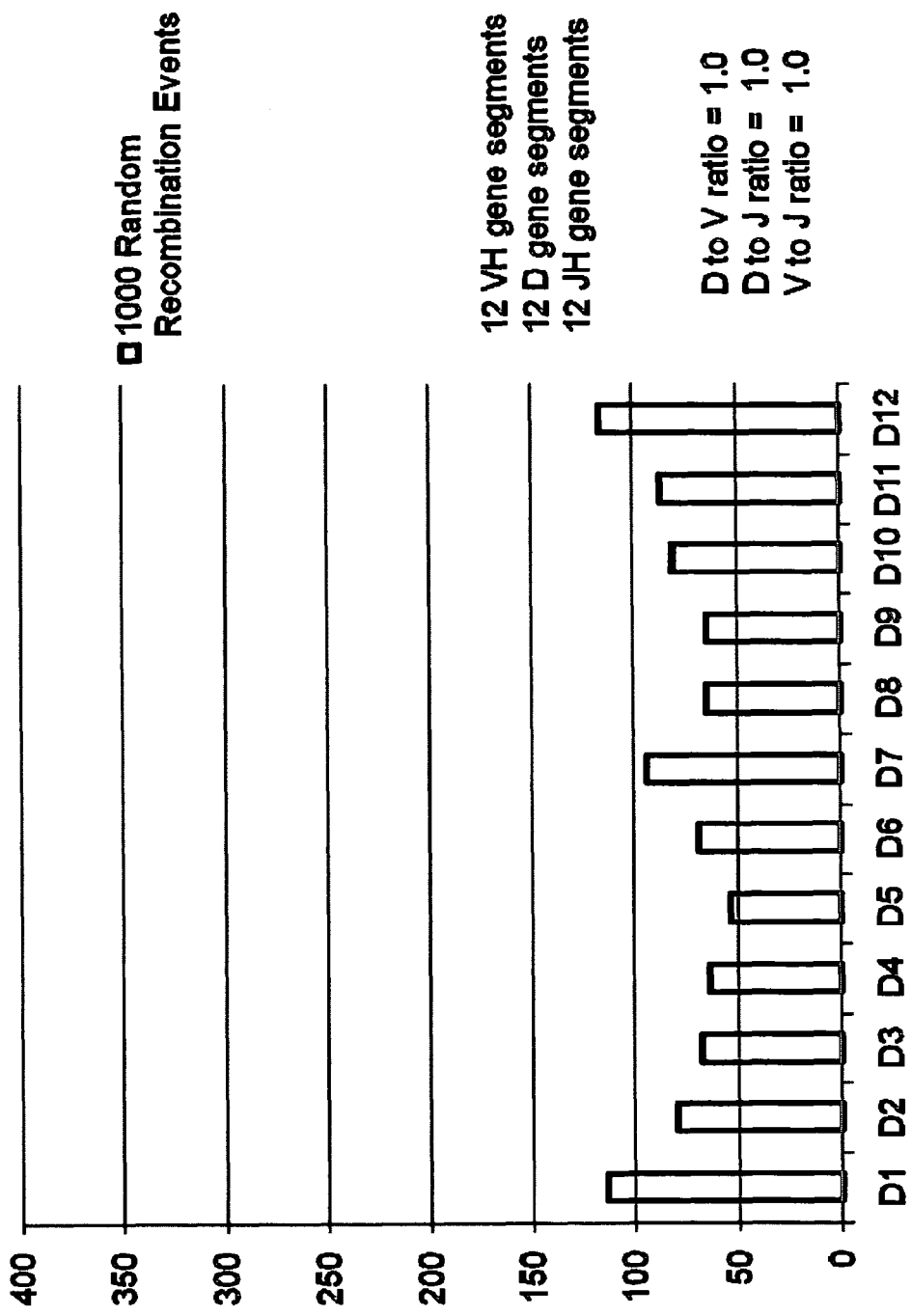
Figure 2C:
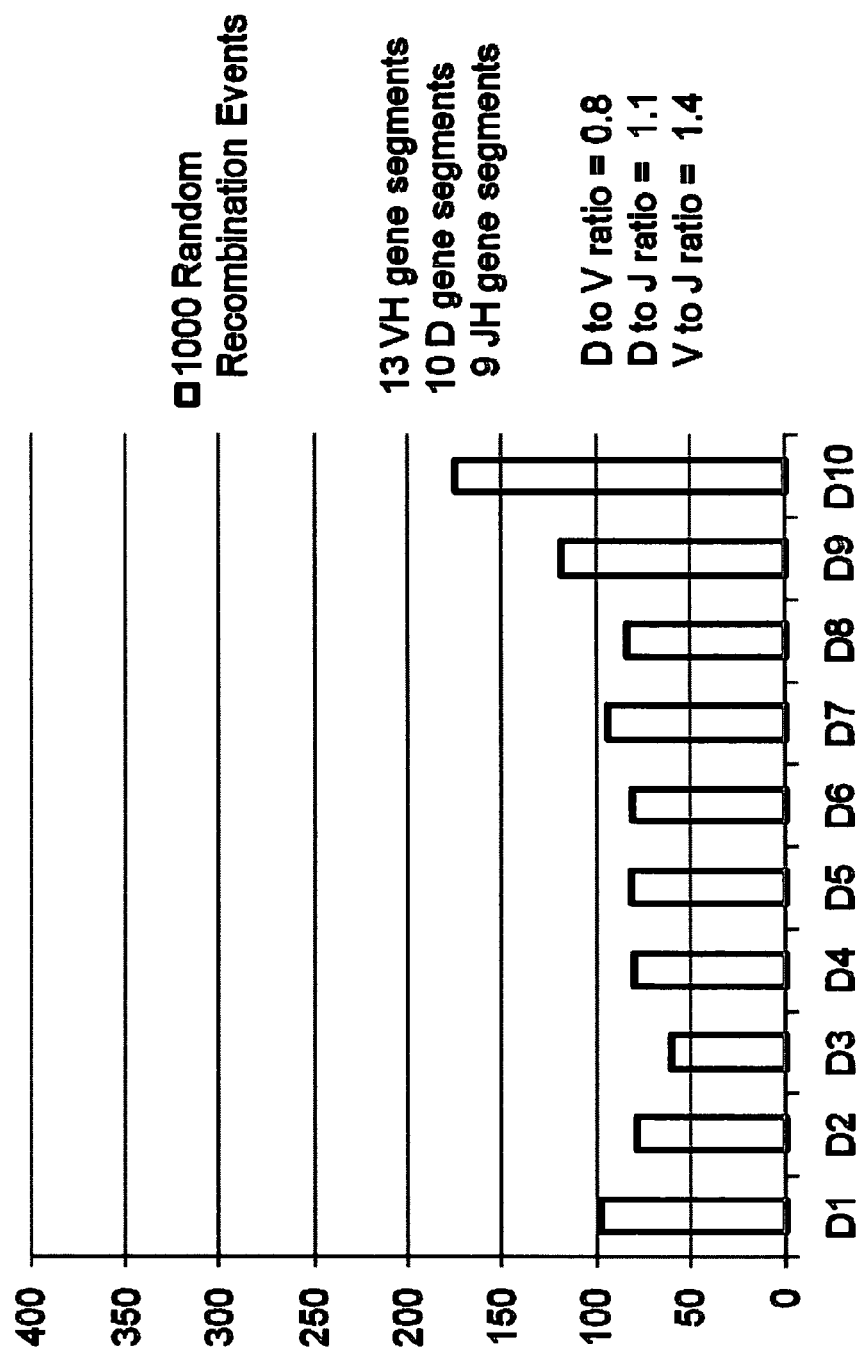

By contrast, according the present disclosure there are provided for the first time compositions and methods in which greater immunoglobulin structural diversity can be generated in vitro through selection of appropriate relative representation of the immunoglobulin gene elements to generate a highly diverse repertoire. As shown in FIG. 2, for example, such enhanced structural diversity is obtained when the ratio of $V_H$ region genes to D segment genes is about 1:1 to 1:2 and the ratio of $J_H$ segment genes to D segment genes is about 1:1 to 1:2, or when the ratio of $V_H$ region genes to $J_H$ segment genes is about 1:2 (V to J) to 2:1 (V to J), or when the combined number of $V_H$ region genes together with $J_H$ segment genes is not greater than the number of D segment genes when there is a plurality of D gene segments, or when 6, 7, 8, 9, 10, 11 or 12 D segment genes are present. A parameter that is described as being "about" a certain quantitative value typically may have a value that varies (i.e., may be greater than or less than) from the stated value by no more than 50%, and in preferred embodiments by no more than 40%, 30%, 25%, 20%, 15%, 10% or 5%. According to certain preferred embodiments as elaborated herein, the unexpected arrival at the present subject matter thus results from previously unappreciated significance of the gene segment usage biases that become apparent in vitro in the absence of the regulation normally imparted during recombination in vivo (as discussed supra), and of the importance of the relative ratios of the gene segments.

According to preferred embodiments disclosed herein, a nucleic acid composition for generating immunoglobulin structural diversity may be assembled from herein specified immunoglobulin gene elements, including naturally occurring and artificial sequences, using genetic engineering methodologies and molecular biology techniques with which those skilled in the art will be familiar. Useful immunoglobulin genetic elements for producing the compositions described herein include mammalian Ig heavy chain variable ($V_H$) and light chain variable ($V_L$) region genes, natural or artificial Ig diversity (D) segment genes, Ig heavy chain joining ($J_H$) and light chain joining ($J_L$) segment genes, and Ig locus recombination signal sequences (RSSs). Immunoglobulin variable (V) region genes are known in the art and include in their polypeptide-encoding sequences at least the polynucleotide coding sequence for one antibody complementarity determining region (CDR), for example, a first or a second CDR known as CDR1 or CDR2 according to conventional nomenclature with which those skilled in the art will be familiar, preferably coding sequence for two CDRs, for example, CDR1 and CDR2, and more preferably coding sequence for CDR1 and CDR2 and at least a portion (e.g., 1, 2, 3, 4, 5, 6, 7, 8, 9, 10, 11, 12, 13 or more amino acids) of CDR3, where it will be appreciated that typically one or more amino acids of CDR3 may be encoded at least in part by at least one nucleotide that is present in a D segment gene and/or in a J segment gene. (See, e.g., Lefranc M.-P., 1997 *Immunology Today* 18:509; Lefranc, 1999 *The Immunologist*, 7:132-13; Lefranc et al., 2003 *Dev. Comp. Immunol.* 27:55-77; Ruiz et al., 2002 *Immunogenetics* 53:857-883; Kaas et al., 2007 *Current Bioinformatics* 2:21-30; Kaas et al., 2004 *Nucl. Acids. Res.*, 32:D208-D210.)

Immunoglobulin D segment genes are also known in the art and as provided herein may include coding regions for natural or non-naturally occurring D segments which coding regions comprise 1, 2, 3, 4, 5, 6, 7, 8, 9, 10, 11, 12, 13, 14, 15, 16, 17, 18, 19, 20, 21, 22, 23 or 24 nucleotides. Immunoglobulin J segment genes are also known in the art, for example, from immunoglobulin genes or cDNAs that have been sequenced, and typically comprise J segment-encoding regions of about 1-51 nucleotides.

As described herein, many such Ig gene sequences are therefore known in the art (e.g., Kabat et al., *Sequences of Proteins of Immunological Interest*, Edition: 5, 1992 DIANE Publishing, 1992, Darby, Pa., ISBN 094137565X, 9780941375658; Tomlinson et al., 1992 *J Mol Biol* 227:776; Milner et al., 1995 *Ann N Y Acad Sci* 764:50) and can be used in the several embodiments herein disclosed, including mammalian Ig gene sequences from human, mouse, rat, rabbit, canine, feline, equine, bovine, monkey, baboon, macaque, chimpanzee, gorilla, orangutan, camel, llama, alpaca and ovine genomes. Preferred embodiments relate to human Ig gene sequences but the invention is not intended to be so limited.

Other genetic elements that may be useful in certain herein disclosed embodiments include membrane anchor domain polypeptide encoding polynucleotide sequences and variants or fragments thereof (e.g., primary sequence variants or truncated products that retain 3D structural properties of the corresponding unmodified polypeptide, such as space-filling, charge distribution and/or hydrophobicity/hydrophilicity) that encode membrane anchor domain polypeptides that localize the polypeptides in which they are present to the surfaces of cells in which they are expressed.

Other genetic elements that may be useful in certain herein disclosed embodiments include specific protein-protein association domain encoding polynucleotide sequences and variants and fragments thereof (e.g., primary sequence variants or truncated products that retain 3D structural properties of the corresponding unmodified polypeptide, such as space-filling, charge distribution and/or hydrophobicity/hydrophilicity) that mediate specific protein-protein associations such as specific binding, as described herein.

Specific binding interactions such as a specific protein-protein association or a specific antibody-antigen binding interaction preferably includes a protein-protein binding event, or an antibody-antigen binding event, having an affinity constant, $K_a$, of greater than or equal to about $10^4 \text{ M}^{-1}$, more preferably of greater than or equal to about $10^5 \text{ M}^{-1}$, more preferably of greater than or equal to about $10^6 \text{ M}^{-1}$, and still more preferably of greater than or equal to about $10^7 \text{ M}^{-1}$. Affinities of specific binding partners including antibodies can be readily determined using conventional techniques, for example, those described by Scatchard et al. (*Ann. N.Y. Acad. Sci. USA* 51:660 (1949)), by Harlow et al., in *Antibodies: A Laboratory Manual*, Cold Spring Harbor Laboratory (1988), by Weir, *Handbook of Experimental Immunology*, 1986, Blackwell Scientific, Boston, by Scopes, *Protein Purification: Principles and Practice*, 1987 Springer-Verlag, New York, by surface plasmon resonance (BIAcore, Biosensor, Piscataway, N.J., see, e.g., Wolff et al., *Cancer Res.* 53:2560-2565 (1993)) or by other techniques known to the art.

As noted above, certain genetic elements that may be useful in presently disclosed embodiments include recombination signal sequences (RSSs), which are nucleic acid sequences that comprise a heptamer and a nonamer separated by a spacer of either 12 or 23 nucleotides, and that are specifically recognized in a complex recombination mechanism according to which a first RSS having a 12-nucleotide spacer recombines with a second RSS having a 23-nucleotide spacer. The orientation of the RSS determines if recombination results in a deletion or inversion of the intervening sequence.

As also described above, extensive investigations of RSS processes have led to an understanding of nucleotide positions within RSSs that cannot be varied without compromising RSS functional activity in genetic recombination mechanisms, and of other nucleotide positions within RSSs that can be varied to alter (e.g., increase or decrease in a statistically significant manner) the efficiency of RSS functional activity in genetic recombination mechanisms, and of other positions within RSSs that can be varied without having any significant effect on RSS functional activity in genetic recombination mechanisms (e.g., Ramsden et. al 1994; Akamatsu et. al. 1994 *J Immunol* 153:4520; Hesse et. al. 1989 *Genes Dev* 3:1053; Fanning et. al. 1996; Larijani et. al 1999; Nadel et. al. 1998 *J Exp Med* 187:1495; Lee et al. 2003 PLoS Biol 1:E1; Cowell et al. 2004 *Immunol. Rev.* 200:57).

According to the presently contemplated embodiments, an RSS may be any RSS that is known to the art, including sequence variants of known RSSs that comprise one or more nucleotide substitutions (e.g., about 1, 2, 3, 4, 5, 6, 7, 8, 9, 10, 11, 12, 13, 14, 15, 16, 17, 18 or more substitutions) relative to the known RSS sequence and which, by virtue of such substitutions, predictably have low efficiency (e.g., about 1% or less, relative to a high efficiency RSS), medium efficiency (e.g., about 10% to about 20%, relative to a high efficiency RSS) or high efficiency, including those variants for which one or more nucleotide substitutions relative to a known RSS sequence will have no significant effect on the recombination efficiency of the RSS (e.g., the success rate of the RSS in promoting formation of a recombination product, as known in the art and readily determined according to assays such as those disclosed in Hesse et al., 1989 *Genes Dev* 3:1053; Akamatsu et al., 1994 *J Immunol* 153:4520; Nadel et al., 1998 *J Exp Med* 187:1495; Lee et al., 2003 *PLoS Biol* 1:E1; Cowell et al., 2004 *Immunol Rev* 200:57).

Further according to the presently disclosed embodiments, it is to be understood that when, for instance, a first nucleic acid comprising a first RSS is described as being capable of functional recombination with a second RSS that is present in a second nucleic acid, such capability includes compliance with the 12/23 rule for RSS nucleotide spacers as described herein and known in the art, such that if the first RSS comprises a 12-nucleotide spacer then the second RSS will comprise a 23-nucleotide spacer, and similarly if the first RSS comprises a 23-nucleotide spacer then the second RSS will comprise a 12-nucleotide spacer.

Certain embodiments of the presently disclosed nucleic acid compositions comprise one or more of first, second, third and fourth isolated nucleic acids as described herein, where such nucleic acids may be separate molecules or may be joined into a single nucleic molecule, or may be present as two or three nucleic acid molecules, so long as the nucleic acid is capable of undergoing recombination events to form a recombined polynucleotide that encodes an immunoglobulin polypeptide as recited. These nucleic acid compositions may comprise one or more RSSs which, as noted above, may be any RSS provided the 12/23 rule for RSS spacers is satisfied in any particular nucleic acid composition as a whole. The identities of particular RSSs may be specified by qualifying the RSS according to a particular genetic element with which it is associated in an isolated nucleic acid.

For example, where a nucleic acid composition comprises a first isolated nucleic acid that comprises one or a plurality of mammalian immunoglobulin heavy chain variable ($V_H$) region genes, each having a $V_H$ encoding polynucleotide sequence and a RSS that is situated 3' to the $V_H$ encoding polynucleotide sequence, the RSS may be referred to as a "$V_H$ region RSS" that is located 3' to the $V_H$ encoding sequence. As another example, where a nucleic acid composition comprises a second isolated nucleic acid that comprises one or a plurality of mammalian immunoglobulin heavy chain diversity (D) segment genes, each having a D segment encoding polynucleotide sequence and two RSSs, with the first RSS being situated 5' to the D segment encoding sequence and the second RSS being situated 3' to the D segment encoding sequence, the first RSS may be referred to as "a D segment upstream RSS" that is located 5' to each D segment encoding sequence, and the second RSS may be referred to as "a D segment downstream RSS" that is located 3' to each D segment encoding sequence. The skilled person will accordingly appreciate what is meant by other similarly specified RSSs, including, for example, an RSS that is "a $J_H$ segment RSS" that is located 5' to a $J_H$ segment encoding polynucleotide sequence, another RSS that is "a $V_L$ region RSS" that is located 3' to a $V_L$ region encoding polynucleotide sequence, and another RSS that is "a $J_L$ segment RSS" that is located 5' to a $J_L$ segment encoding polynucleotide sequence.

Examples of RSS sequences known to the art, including their characterization as high, medium or low efficiency RSSs, are presented in Table 1.

TABLE 1

EXEMPLARY RECOMBINATION SIGNAL SEQUENCES

| heptamer H12 | spacer S12 | nonamer N12 | Seq. ID No. | heptamer H23 | spacer S23 | nonamer N23 | Seq Id No: * |
|---|---|---|---|---|---|---|---|
| Part I. Efficiency: HIGH | | | | | | | |
| CACAGTG | ATACAG ACCTTA | ACAAAAAC C | 29 | CACAGTG | GTAGTACTCCACTGTCTGGCACAAAAACC TGT | | 30 4 |
| CACAGTG | CTACAG ACTGGA | ACAAAAAC C | 31 | CACAGTG | GTAGTACTCCACTGTCTGGCACAAAAACC TGT | | 32 3 |
| CACAGTG | CTCCAG GGCTGA | ACAAAAAC C | 33 | CACAGTG | GTAGTACTCCACTGTCTGGGACAAAAACC TGT | | 34 1 |
| CACAGTG | CTACAG ACTGGA | ACAAAAAC C | 35 | CACAGTG | TTGCAACCACATCCTGAGTGACAAAAACC TGT | | 36 2 |
| CACAGTG | CTACAG ACTGGA | ACAAAAAC C | 37 | CACAGTG | GTAGTACTCCACTGTCTGGCACAAAAACC TGT | | 38 2 |
| CACAGTG | CTACAG ACTGGA | ACAAAAAC C | 39 | CACAGTG | ACGGAGATAAAGGAGGAAG CAGG | ACAAAAACC | 40 2 |
| CACAGTG | GTACAG ACCAAT | ACAGAAAC C | 41 | CACAGTG | GCCGGGCCCCGCGGCCCG GCGGC | ACAAAAACC | 42 5 |
| Part II. Efficiency: MEDIUM (~10-20% of High) | | | | | | | |
| CACGGTG | CTACAG ACTGGA | ACAAAAAC C | 43 | CACAGTG | GTAGTACTCCACTGTCTGGCACAAAAACC TGT | | 44 3 |
| CACAATG | CTACAG ACTGGA | ACAAAAAC C | 45 | CACAGTG | GTAGTACTCCACTGTCTGGCACAAAAACC TGT | | 46 3 |
| CACAGCG | CTACAG ACTGGA | ACAAAAAC C | 47 | CACAGTG | GTAGTACTCCACTGTCTGGCACAAAAACC TGT | | 48 3 |
| CACAGTG | CTACAG ACTGGA | ACAAAAAC C | 49 | CACAATG | GTAGTACTCCACTGTCTGGCACAAAAACC TGT | | 50 3 |
| CACAGTG | CTACAG ACTGGA | ACAAAAAC C | 51 | CACAGCG | GTAGTACTCCACTGTCTGGCACAAAAACC TGT | | 52 3 |
| CACAGTG | CTACAG ACTGGA | ACAAAAAC C | 53 | CACAGTA | GTAGTACTCCACTGTCTGGCACAAAAACC TGT | | 54 3 |
| CACAGTG | CTACAG ACTGGA | ACAAAAAC C | 55 | CACAGTG | GTAGTACTCCACTGTCTGGCACAATAACC TGT | | 56 3 |
| CACAGTG | CTACAG ACTGGA | ACAAAAAC C | 57 | CACAGTG | GTAGTACTCCACTGTCTGGCACAAGAACC TGT | | 58 3 |
| CACAGTG | CTACAG ACTGGA | ACAAAAAC C | 59 | CACAGTG | GTAGTACTCCACTGTCTGGCACACGAACC TGT | | 60 3 |
| CACAGTG | CTACAG ACTGGA | CAAAAACC C | 61 | CACAGTG | GTAGTACTCCACTGTCTGGCACAAAAACC TGT | | 62 3 |
| CACAGTG | CTACAG ACTGGA | ACAAAAAC C | 63 | CACAGTG | GTAGTACTCCACTGTCTGGCACACGAACC TGT | | 64 3 |
| CACAATG | CTACAG ACTGGA | ACAAAAAC C | 65 | CACAATG | GTAGTACTCCACTGTCTGGCACAAAAACC TGT | | 66 3 |
| CACAGCG | CTACAG ACTGGA | ACAAAAAC C | 67 | CACAGCG | GTAGTACTCCACTGTCTGGCACAAAAACC TGT | | 68 3 |

TABLE 1-continued

EXEMPLARY RECOMBINATION SIGNAL SEQUENCES

| heptamer H12 | spacer S12 | nonamer N12 | Seq. ID No. | heptamer H23 | spacer S23 | nonamer N23 | Seq Id No: * |
|---|---|---|---|---|---|---|---|
| Part III. Efficiency: LOW (~1% or less of High) | | | | | | | |
| TACAGTG | CTACAG ACTGGA | ACAAAAAC C | 69 | CACAGTA | GTAGTACTCCACTGTCTGGCACAAAAACC TGT | | 70 3 |
| GACAGTG | CTACAG ACTGGA | ACAAAAAC C | 71 | CACAGTG | GTAGTACTCCACTGTCTGGCACAAAAACC TGT | | 72 3 |
| CATAGTG | CTACAG ACTGGA | ACAAAAAC C | 73 | CACAATG | GTAGTACTCCACTGTCTGGCACAAAAACC TGT | | 74 3 |
| CACAATG | CTACAG ACTGGA | ACAAAAAC C | 75 | CATAGTG | GTAGTACTCCACTGTCTGGCACAAAAACC TGT | | 76 3 |
| CACAGTG | CTACAG ACTGGA | ACAAAAAC C | 77 | CACAGTG | GTAGTACTCCACTGTCTGGTGTCTCTGA TGT | | 78 3 |
| CAGAGTG | CTCCAG GGCTGA | ACAAAAAC C | 79 | CACAGTG | GTAGTACTCCACTGTCTGGGACAAAAACC TGT | | 80 1 |
| CACAGTG | CTCCAG GGCTGA | AAAAAAAC C | 81 | CACAGTG | GTAGTACTCCACTGTCTGGGACAAAAACC TGT | | 82 1 |
| CTCAGTG | CTCCAG GGCTGA | ACAAAAAC C | 83 | CACAGTG | GTAGTACTCCACTGTCTGGGACAAAAACC TGT | | 84 1 |

*(1) Akamatsu et al. 1994; (2) Cowell et al. 2004; (3) Hesse et al. 1989; (4) Lee et al. 2003; (5) Nadel et al. 1998.

Certain preferred embodiments contemplate construction of nucleic acid compositions for generating immunoglobulin structural diversity as provided herein whereby selection of RSSs of known efficiencies at prescribed positions may advantageously counteract biases in particular immunoglobulin gene utilization that would otherwise result from the relative locations of the several Ig genetic elements. More specifically, and without wishing to be bound by theory, the nucleic acid compositions disclosed herein are envisioned as comprising, in a 5' to 3' orientation according to molecular biology conventions for designating directionality to a DNA coding strand:

(a) one or a plurality of Ig V region genes, each having (i) an Ig V region encoding polynucleotide sequence and (ii) a V region RSS that is located 3' to the V region encoding polynucleotide;

(b) one or a plurality of Ig D segment genes, each having (i) a D segment encoding polynucleotide sequence, (ii) a D segment upstream RSS that is located 5' to the D segment encoding polynucleotide, and (iii) a D segment downstream RSS that is located 3' to the D segment encoding polynucleotide; and (c) one or a plurality of Ig J segment genes, each having (i) a J segment encoding polynucleotide sequence and (ii) a J segment RSS that is located 5' to the J segment encoding polynucleotide.

According to such a configuration, it will be appreciated that in the course, simultaneously or sequentially and in either order, of functional recombination of the V region RSS with the D segment upstream RSS, and functional recombination of the D segment downstream RSS with the J segment RSS, unused intervening V, D and J genes are deleted such that if the selection of V, D and J genes is random, the frequency of usage of particular genes will be biased.

For example, V region genes situated closer to the 5' end of the construct are likely to be overused in productive RSS-RSS recombination events, because they have a lower probability of being deleted during V-D recombination, while V region genes situated closer to the 3' end of (a) are likely to be underused given the higher probability they will be deleted during recombination. Similarly, D segment genes situated at or near the 5' end of (b) are likely to be underused, while those situated at or near the 3' end of (b) are more likely to survive deletion events accompanying recombinase-mediated DNA cleavage and subsequent repair, and so would be overused in productive recombination events.

As provided herein, enhanced generation of immunoglobulin structural diversity in the present artificial system is accomplished through efficient and relatively unbiased utilization of Ig V, D and J genetic elements, including by designing nucleic acid constructs that have defined relative ratios of V, D and J genes and/or restricted number of D segment genes and/or by strategic positioning of RSSs of predefined efficiencies.

Accordingly, in certain embodiments there is provided a nucleic acid composition for generating Ig structural diversity that comprises one or a plurality of Ig V region genes, Ig D segment genes, and Ig J segment genes as described herein, and optionally further comprising a polynucleotide encoding a membrane anchor domain polypeptide and/or a polynucleotide encoding a specific protein-protein association domain, in which (a) the V region genes and the D segment genes are present at a ratio of about 1:1 to 1:2, and the J segment genes and the mammalian D segment genes are present at a ratio of about 1:1 to 1:2; or in which (b) the V region genes and the J segment genes are present at a ratio of about 1:2 (V to J) to 2:1 (V to J); or in which (c) the V region genes, together with the J segment genes, are not greater in number than the D segment genes; or in which (d) there are 6, 7, 8, 9, 10, 11 or 12 D segment genes.

In certain further embodiments, (a) 12-50 contiguous V region genes (in preferred embodiments $V_H$ region genes) are present of which about 10% to about 30% of said V region genes are contiguous with a 5'-most located V region gene and each V region gene comprises a V region (preferably a $V_H$ region) RSS of low or medium RSS efficiency, and of which about 70% to about 90% of said V region genes are contiguous with a 3'-most located V region gene and each comprises a V region RSS of high RSS efficiency; and (b) a plurality of contiguous D segment genes are present of which (i) about 80% to about 90% of said D segment genes are contiguous with a 5'-most located D segment gene and each comprises a D segment upstream RSS of high RSS efficiency and a D segment downstream RSS of high RSS efficiency, and (ii) about 10% to about 20% of said D segment genes are contiguous with a 3'-most located D segment gene and each comprises a D segment upstream RSS of low or medium RSS efficiency and a D segment downstream RSS of low or medium RSS efficiency, wherein the plurality of V region genes, together with the one or a plurality of J segment genes, are not greater in number than said plurality of D segment genes.

It will be understood by those familiar with the art that by convention and due to nucleic acid 5'-to-3' polarity, a nucleic acid coding strand comprises an upstream or 5' end (or 5' terminus) and a downstream or 3' end (or 3' terminus) such that in the linear polymer containing a plurality of linked and tandemly, consecutively and/or sequentially arrayed (e.g., contiguous) genes, a single gene (e.g., of a designated class, such as a V region gene) may be situated closer to the 5' terminus than all others (e.g., the "5'-most located" gene) and a different single gene (e.g., of the designated class) may be situated closer to the 3' terminus than all the others (e.g., the "3'-most located" gene). Hence, distribution of RSSs having specified recombination efficiencies amongst the plurality of contiguous genes in the nucleic acid molecule will vary according to the number of genes that are used in a particular construct, in order for a specified percentage of such genes to comprise a specified RSS type. Additionally and as provided herein according to certain preferred embodiments such RSS distributions will accordingly confer gene utilizations that are about equal, thereby advantageously providing compositions for generating increased Ig structural diversity.

In related but distinct embodiments, there is accordingly provided a nucleic acid composition for generating Ig structural diversity that comprises one or a plurality of Ig V region genes, Ig D segment genes, and Ig J segment genes as described above, and that is characterized by one or more of (a) 12-50 contiguous V (preferably $V_H$) region genes are present of which about 10% to about 30% are contiguous with a 5'-most located V region gene and each V region gene comprises a V region RSS of low or medium RSS efficiency; (b) 12-50 contiguous V (preferably $V_H$) region genes are present of which about 70% to about 90% are contiguous with a 3'-most located V region gene and each V region gene comprises a V region RSS of high RSS efficiency; (c) a plurality of contiguous D segment genes are present of which about 80% to about 90% are contiguous with a 5'-most located D segment gene and each D segment gene comprises a D segment upstream RSS of high RSS efficiency and a D segment downstream RSS of high RSS efficiency; and (d) a plurality of contiguous D segment genes are present of which about 10% to about 20% are contiguous with a 3'-most located D segment gene and each comprises a D segment upstream RSS of low or medium RSS efficiency and a D segment downstream RSS of low or medium RSS efficiency.

As disclosed herein according to certain embodiments there are provided nucleic acid compositions for generating immunoglobulin structural diversity by including, for example by way of illustration and not limitation in a composition that contains immunoglobulin light chain-encoding sequences (e.g., $V_L$ and $J_L$), an immunoglobulin diversity (D) segment gene, which may in certain related embodiments comprise a naturally occurring D segment encoding sequence (e.g., Corbett et al., 1997 *J Mol Biol* 270:587; NCBI locus NG_001019; vbase, 1997 MRC Centre for Protein Engineering). In certain distinct but related embodiments, however, a nucleic acid composition as provided herein, for instance and without limitation, an Ig light-chain or light-chain fusion protein encoding nucleic acid composition, may comprise an artificial D segment gene that may comprise a non-naturally occurring sequence encoding an artificial D segment and that is positioned to be recombined between $V_L$ and $J_L$, and which may comprise a nucleotide sequence representing a subset or combination of sequences found in any human D segment gene including a single nucleotide, a dinucleotide or a fusion of complete or partial human D segment gene sequences, but which in preferred embodiments is not generally recognized as a conventional human D segment gene. Such an artificial D segment encoding sequence of 1, 2, 3, 4, 5, 6, 7, 8, 9, 10, 11, 12, 13, 14, 15, 16, 17, 18, 19, 20, 21, 22, 23 or 24 nucleotides is contemplated. Accordingly, a D segment encoding sequence may include a single nucleotide, or any dinucleotide, or any combination of two or more fused D segment encoding polynucleotide sequences from two or more distinct, recognized immunoglobulin D segment genes that occur naturally in a genome, preferably the human genome. Non-limiting examples of D segment encoding polynucleotide sequences are presented in Table 2.

TABLE 2

EXEMPLARY D SEGMENT ENCODING SEQUENCES

| D | # | Nucleotide Sequence | SEQ ID NO: |
|---|---|---|---|
| D1 | 1-1 | GGTACAACTGGAACGAC | 85 |
| | 1-7 | GGTATTACTGGAACTAC | 86 |
| | 1-20 | GGTATAACTGGAACGAC | 87 |
| | 1-26 | GGTATAGTGGGAGCTACTAC | 88 |
| D2 | 2-2 | AGGATATTGTAGTAGTACCAGCTGCTATACC | 89 |
| | 2-8 | AGGATATTGTACTAATGGTGIATGCTATACC | 90 |
| | 2-15 | AGGATATTGTAGTGGTGGTAGCTGCTACTCC | 91 |
| | 2-21 | AGCATATTGTGGTGGTGACTGCTATTCC | 92 |
| D3 | 3-3 | GTATTACGATTTTTGGAGTGGTTATTATACC | 93 |
| | 3-9 | GTATTACGATATTTTGACTGGTTATTATAAC | 94 |
| | 3-10 | GTATTACTATTGGTTCGGGGAGTTATTATAAC | 95 |
| | 3-16 | GTATTATTGATTACGTTTGGGGGAGTTATCGTTATACC | 96 |
| | 3-22 | GTATTACTATGATAGTAGTGGTTATTACTAC | 97 |
| D4 | 4-4 | TGACTACAGTAACTAC | 98 |
| | 4-11 | TGACTACAGTAACTAC | 99 |
| | 4-17 | TGACTACGGTGACTAC | 100 |
| | 4-23 | TGACTACGGTGGTAACTCC | 101 |
| D5 | 5-5 | GTGGATACAGCTATGGTTAC | 102 |
| | 5-12 | GTGGATATAGTGGCTACGATTAC | 103 |
| | 5-18 | GTGGATACAGCTATGGTTAC | 104 |
| | 5-24 | GTAGAGATGGCTACAATTAC | 105 |
| D6 | 6-6 | GAGTATAGCAGCTCGTCC | 106 |
| | 6-13 | GGGTATAGCAGCAGCTGGTAC | 107 |
| | 6-19 | GGGTATAGCAGTGGCTGGTAC | 108 |
| D7 | 7-27 | CTAACTGGGGA | 109 |

In certain embodiments a D segment gene may therefore be provided on immunoglobulin light chain diversity generating constructs, as described in detail, for instance, in Example 2. The inclusion of a D segment gene converts an otherwise bimolecular reaction system into a tripartite system. Because of the 12/23 pairing rule (discussed supra), in an exemplary bimolecular system all the V segments may be adjacent to RSSs (i.e., V region RSSs) having spacers of a first common size (e.g., utilizing either 12 or 23 nucleotides) and the J segments are all adjacent to RSSs (i.e., J segment RSSs) having spacers of a second common size that is not the same as the first common size used in V region RSS spacers. In other words, if the V region RSSs contain 23-nucleotide spacers then the J segment RSSs would contain 12-nucleotide spacers, and vice versa. This configuration directs V to J recombination, but without the regulation found in vivo it would continue to consume Ig gene segments until either only a single V or J gene segment remains, or until the recombinase is turned off by cellular mechanisms. In the absence of being able to turn off the recombinase in a specific cell that has completed recombination as is accomplished in vivo, continuing recombination would result in the vast underrepresentation of proximal V-J segments and would favor usage of the distal segments. In a tripartite system, the V and J segments would both use RSSs having the same spacer sizes (i.e., V region RSSs and J segment RSSs would have the same spacer size, being either 12- or 23-nucleotides) and the D segment gene RSSs (i.e., the D segment upstream RSS and the D segment downstream RSS) would each use the complementary RSS signal size (i.e., 23 nucleotides if V region RSSs and J segment RSSs use 12-nucleotide spacers, and 12 nucleotides if V region RSSs and J segment RSSs use 23-nucleotide spacers). In this exemplary configuration, because the V region RSSs and J segment RSSs have spacers of the same size, the 12/23 rule prevents them from recombining directly. Instead recombination proceeds through a D segment gene that comprises a D segment upstream RSS and a D segment downstream RSS having spacers of the same size. In certain related embodiments and without wishing to be bound by theory, it is contemplated therefore that limiting the number of D segment genes may limit the number of rounds of recombination that a particular Ig diversity-generating nucleic acid composition can undergo; recombination stops when there is only a single D segment remaining and all D segment RSSs have been utilized. In another related embodiment in which the Ig diversity-generating nucleic acid composition comprises one D segment gene, V-D recombination can occur only once via functional recombination of the D segment upstream RSS with the V region RSS, and D-J recombination can occur only once via functional recombination of the D segment downstream RSS with the J segment RSS, thus reducing biases in gene segment utilization.

As the D segment is found naturally in heavy chains and not light chains, these and related embodiments also contemplate unprecedented expansion of the immunoglobulin light chain variable region repertoire, by providing the D segment as an additional combinatorial source of structural diversity through V-D-J recombination events as described herein.

Among the several embodiments described herein, there are also provided the means for generating structurally diverse immunoglobulin gene libraries, including recombined genes encoding antibodies having membrane anchor domains that permit their display on the surfaces of host cells expressing such immunoglobulin genes. Advantages associated with cell surface expression, as distinct from secreted forms, of structurally diverse immunoglobulins as described herein, will be readily appreciated by persons familiar with the art in view of the present disclosure, for example, to facilitate the identification and/or selection of cells containing a particular rearranged immunoglobulin gene, such as a cell expressing an antibody having a desired antigen specificity.

In addition, certain preferred embodiments include the use of host cells that are capable of immunoglobulin gene rearrangement, but that may usefully be expanded in number without immunoglobulin gene rearrangement taking place. In certain particularly preferred embodiments, such host cells are capable of expressing recombination control elements that mediate immunoglobulin gene rearrangement events, but the expression of control elements is regulated in such a manner as to permit expansion of the host cell population prior to permitting the V-D-J gene rearrangement which generates CDR3 sequence diversity.

As also described elsewhere herein, recombination control elements include the RAG-1, and RAG-2 genes and their respective gene products, for which defined roles in regulating immunoglobulin gene rearrangement/recombination events have been biochemically defined. Preferably such recombination control elements are operably linked to the nucleic acid compositions that, as described herein, comprise immunoglobulin structural domain-encoding polynucleotide sequences and recombination signal sequences (RSSs). According to certain such embodiments a nucleic acid composition for generating Ig structural diversity as provided herein is under control of an operably linked recombination control element when one, two or more recombination events that the nucleic acid composition undergoes to form a recombined polynucleotide that encodes an immunoglobulin polypeptide or fusion protein are mediated by the recombination control element. The recombination control element may be inducible, for example, through regulation of its expression by a promoter such as a tightly regulated promoter.

For example and in certain preferred embodiments, a host cell that comprises a nucleic acid composition for generating Ig structural diversity as provided herein, and that also comprises an operably linked inducible recombination control element that controls one or more recombination events which give rise to a productive immunoglobulin or Ig fusion protein encoding polynucleotide, may contain the chromosomally integrated nucleic acid composition under conditions wherein at least one component of the recombination control element (e.g., RAG-1 or RAG-2) is not constitutively (productively, e.g., at functionally relevant levels) expressed, but may be expressed upon exposure of the host cell to an inducer.

Such a host cell may advantageously be expanded to obtain a population of host cells bearing the chromosomally integrated nucleic acid composition, such that the expanded population can be induced with the inducer to obtain a population of cells each expressing a structurally diverse immunoglobulin subsequent to two or more recombination events to form a recombined polynucleotide that encodes the immunoglobulin, where such recombination events are mediated by recombination control elements the expression of which is induced by the inducer. This important feature of these and related preferred embodiments allows recombination to occur subsequent to expansion of the host cell population. According to non-limiting theory, such preferred embodiments (in which Ig gene recombination takes place only after expansion of a host cell population) offer particular advantages associated with increasing the opportunities for different structurally diverse immunoglobulins to result from random recombination events in a large number of distinct cells that have chromosomally integrated the herein disclosed nucleic acid compositions for generating Ig structural diversity. Further according to non-limiting theory, absent such an opportunity to first expand the host cell population, an Ig gene recombination-competent cell having a chromosomally integrated nucleic acid composition for generating Ig structural diversity would be able to complete recombination soon after subcloning, such that only a limited number of different antibodies would have been generated.

Certain related embodiments advantageously provide non-naturally occurring immunoglobulin fusion proteins that usefully feature immunoglobulin heavy chains having a membrane anchor domain polypeptide, and/or recombination-mediated assembly of functional immunoglobulin light chains having either or both of (i) a heavy chain diversity (D) segment (including an artificial D segment as described herein) and (ii) a specific protein-protein association domain (e.g., all or a protein-protein associating portion of a mammalian immunoglobulin $C_L$ chain, or an RGD-containing polypeptide that is capable of integrin binding, or a heterodimer-promoting polypeptide domain, or other such domains as described herein and known in the art), or a lipid raft-associating polypeptide domain, where such modified immunoglobulin structures may facilitate generation of large antibody repertoires and identification of cells expressing an immunoglobulin or immunoglobulin-like molecule having a desired V region.

Hence, according to certain embodiments disclosed herein there are provided immunoglobulin fusion polypeptides and proteins that localize to the cell surface by virtue of having naturally present or artificially introduced structural features that direct the fusion protein to the cell surface (e.g., Nelson et al. 2001 *Trends Cell Biol.* 11:483; Ammon et al., 2002 *Arch. Physiol. Biochem.* 110:137; Kasai et al., 2001 *J. Cell Sci.* 114:3115; Watson et al., 2001 *Am. J. Physiol. Cell Physiol.* 281:C215; Chatterjee et al., 200 *J. Biol. Chem.* 275:24013) including by way of illustration and not limitation, secretory signal sequences, leader sequences, plasma membrane anchor domain polypeptides such as hydrophobic transmembrane domains (e.g., Heuck et al., 2002 *Cell Biochem. Biophys.* 36:89; Sadlish et al., 2002 *Biochem J.* 364:777; Phoenix et al., 2002 *Mol. Membr. Biol.* 19:1; Minke et al., 2002 *Physiol. Rev.* 82:429) or glycosylphosphatidylinositol attachment sites ("glypiation" sites, e.g., Chatterjee et al., 2001 *Cell Mol. Life. Sci.* 58:1969; Hooper, 2001 *Proteomics* 1:748; Spiro, 2002 *Glycobiol.* 12:43R), cell surface receptor binding domains, extracellular matrix binding domains, or any other structural feature that causes the fusion protein to localize to the cell surface.

Particularly preferred are fusion proteins that comprise a plasma membrane anchor domain, which may include a transmembrane polypeptide domain typically comprising a membrane spanning domain (e.g., an α-helical domain) which includes a hydrophobic region capable of energetically favorable interaction with the phospholipid fatty acyl tails that form the interior of the plasma membrane bilayer, or which may include a membrane-inserting domain polypeptide typically comprising a membrane-inserting domain which includes a hydrophobic region capable of energetically favorable interaction with the phospholipid fatty acyl tails that form the interior of the plasma membrane bilayer (e.g., outer leaflet phospholipids) but that may not span the entire membrane. Such features are well known to those of ordinary skill in the art, who will further be familiar with methods for introducing nucleic acid sequences encoding these features into the subject expression constructs by genetic engineering, and with routine testing of such constructs to verify cell surface localization of the product. Well known examples of transmembrane proteins having one or more transmembrane polypeptide domains include members of the integrin family, CD44, glycophorin, MHC Class I and II glycoproteins, EGF receptor, G protein coupled receptor (GPCR) family, porin family and other transmembrane proteins. Certain embodiments contemplate using a portion of a transmembrane polypeptide domain such as a truncated polypeptide having membrane-inserting characteristics as may be determined according to standard and well known methodologies.

Certain other embodiments relate to immunoglobulin fusion polypeptides having a specific protein-protein association domain (e.g., Ig $C_L$ polypeptide regions that mediate association to cell surface Ig H chains; $\beta_2$-microglobulin polypeptide regions that mediate association to class I MHC molecule extracellular domains, etc.), an RGD-containing polypeptide that is capable of integrin binding, a lipid raft-associating polypeptide domain, and/or a heterodimer-promoting polypeptide domain. A number of such domains are exemplified by the presently cited publications but these and related embodiments are not intended to be so limited and contemplate other specific protein-protein associating polypeptide domains that are capable of specifically associating with an extracellularly disposed region of a cell surface protein, glycoprotein, lipid, glycolipid, proteoglycan or the like, even where, importantly, such associations may in certain cases be initiated intracellularly, for instance, concomitant with the synthesis, processing, folding, assembly, transport and/or export to the cell surface of a cell surface protein. In another related embodiment, there may be included in the structure of an Ig fusion polypeptide as described herein a domain of a protein, such as a subunit of an integrin, that is known to associate with another cell surface protein that is membrane anchored and exteriorly disposed on a cell surface. Non-limiting examples of such polypeptide domains include, for $C_L$ H-chain-associating domains: (Azuma, T. and Hamaguchi, K. (1976). *J Biochem* 80:1023-38; Hamel et. al. (1987). *J Immunol* 139:3012-20; Horne et. al. (1982). *J Immunol* 129:660-4; Lilie et. al. (1995). *J Mol Biol* 248:190-201; Masuda et. al. (2006). *Febs J* 273:2184-94; Padlan et. al. (1986). *Mol Immunol* 23:951-60; Rinfret et. al. (1985). *J Immunol* 135:2574-81); for RGD-containing polypeptides including those that are capable of integrin binding, Heckmann, D. and Kessler, H. (2007). *Methods Enzymol* 426:463-503 and Takada et. al. (2007). *Genome Biol* 8:215; for lipid raft-associating domains, Browman et. al. 2007). *Trends Cell Biol* 17:394-402; Harder, T. (2004). *Curr Opin Immunol* 16:353-9; Hayashi, T. and Su, T. P. (2005). *Life Sci* 77:1612-24; Holowka, D. and Baird, B. (2001). *Semin Immunol* 13:99-105; Wollscheid et. al. (2004) *Subcell Biochem* 37:121-52).

Extracellular domains include portions of a cell surface molecule, and in particularly preferred embodiments cell surface molecules that are integral membrane proteins or that comprise a plasma membrane spanning transmembrane domain, that extend beyond the outer leaflet of the plasma membrane phospholipid bilayer when the molecule is expressed at a cell surface, preferably in a manner that exposes the extracellular domain portion of such a molecule to the external environment of the cell, also known as the extracellular milieu. Methods for determining whether a portion of a cell surface molecule comprises an extracellular domain are well known to the art and include experimental determination (e.g., direct or indirect labeling of the molecule, evaluation of whether the molecule can be structurally altered by agents to which the plasma membrane is not permeable such as proteolytic or lipolytic enzymes) or topological prediction based on the structure of the molecule (e.g., analysis of the amino acid sequence of a polypeptide) or other methodologies.

Host Cells

According to particularly preferred embodiments a host cell is capable of utilizing recombination signals and undergoing RAG-1/RAG-2 mediated recombination and, more importantly, the recombination is controlled. Preferably the host cell is capable of cell divisions without recombination. For example, in certain embodiments one nucleic acid composition as provided herein may be introduced into a host cell, or in certain other embodiments two or more nucleic acid compositions as provided herein may be introduced into a host cell sequentially and in any order, under conditions and for a time sufficient for chromosomal integration of the nucleic acid composition(s), to obtain one, two or more chromosomally integrated nucleic acid compositions that can undergo at least two or more recombination events in the cell to form a recombined polynucleotide that encodes an immunoglobulin polypeptide, wherein less than one of said recombination events occurs per cell cycle of the host cell. As described herein, these and related embodiments permit expansion of the host cell population prior to the completion of recombination events that give rise to functionally recombined artificial immunoglobulin genes, to obtain a host cell population having immunoglobulin structural diversity.

Control of recombination in such host cells may be achieved according to the compositions and methods described herein, including but not limited to the use of an operably linked recombination control element (e.g., an inducible recombination control element, which may be a tightly regulated inducible recombination control element), and/or through the use of one or more low efficiency RSSs in the nucleic acid composition(s), and/or through the use of low host cell expression levels of one or more of RAG1 or RAG-2, and/or through design of the nucleic acid composition to integrate at a chromosomal integration site offering poor accessibility to host cell recombination mechanisms (e.g., RAG1, RAG-2).

Cell lines to be used as host cells may in certain preferred embodiments additionally contain a functional TdT gene that may be expressed to provide additional diversity at the junctions (e.g., D-J and V-D junctions).

Cell lines may in certain embodiments be pre-B cells or pre-T cells that express these immunoglobulin gene rearrangement-competent cell-specific proteins (e.g., are capable of being induced to express RAG1, RAG-2 and TdT, or alternatively, constitutively express RAG1, RAG-2 and TdT but can be modified to substantially impair the expression of one, two or all three of these enzymes), or genes encoding each of these recombination-associated enzymes can be introduced into a non-B cell expression host cell, for example CHO or 293 cells. For RAG1/2 (also sometimes referred to as RAG-1 and Rag-2, see, e.g., Schatz, D G et. al. (1989) *Cell* 59:1035-48; Oettinger, M. A. et. al. (1990) *Science* 248:1517-23; for TdT see, e.g., That, T. H. & Kearney, J. F. (2004). *J Immunol* 173:4009-19; Koiwai, O. et. al. (1987). *Biochem Biophys Res Commun* 144:185-90; Peterson, R. C. et. al. (1984). *Proc Natl Acad Sci USA* 81:4363-7; for transfection of a host cell with all three of RAG-1, RAG-2 and TdT see, e.g., U.S. Pat. No. 5,756,323.

These and other host cells may be used according to contemplated embodiments of the present invention. For example, it has also been observed that expression of RAG-1 and/or RAG-2 is not restricted to immature developing B-cells in the bone marrow and pre-T cells of the developing thymus, but can also be observed in mature B-cells in vivo and in vitro (Maes et al., 2000 *J Immunol.* 165:703; Hikida et al., 1998 *J Exp Med.* 187:795; Casillas et. al., 1995 *Mol Immunol.* 32:167; Rathbun et. al., 1993 *Int Immunol.* 5:997, Hikida et. al., 1996 *Science* 274:2092). Cell lines have also been shown to continue recombination in vitro and undergo light chain replacement (Maes et. al. 2000 *J Immunol.* 165:703). The secondary rearrangement of Ig genes is speculated to promote receptor editing and has been shown to occur in the germinal centers of secondary lymphoid tissue like the lymph node. IL-6 has been shown to have a role in the regulation of RAG-1 and RAG-2 in mature B-cells in both inducing and terminating expression of the recombinase for secondary rearrangements. (Hillion et. al. 2007 *J Immunol.* 179:6790)

In addition to mature B-cells undergoing secondary rearrangement, RAG-1 and RAG-2 have also been shown to be expressed in mature T-cell lines including Jurkat T-cells. CEM cells have been shown to have V(D)J recombination activity using extrachromosomal substrates (Gauss et. al. 1998 *Eur J Immunol.* 28:351). Treatment of wild-type Jurkat T cells with chemical inhibitors of signaling components revealed that inhibition of Src family kinases using PP2, FK506 etc. overcame the repression of RAG-1 and resulted in increased RAG-1 expression. Mature T-cells have also been shown to reactivate recombination with treatment of anti-CD3/IL7 (Lantelme et. al. 2008 *Mol Immunol.* 45:328).

Recently, tumor cells of non-lymphoid origin have also been shown to express RAG-1 and RAG-2 (Zheng et. al. (2007 Mol Immunol. 44: 2221, Chen et. al. (2007 Faseb J. 21: 2931). Accordingly and without wishing to be restricted by theory, these cells may also be suitable for use as host cells in the presently described in vitro system for generating immunoglobulin structural diversity. According to related embodiments that are contemplated herein, reactivation of V(D)J recombination would provide another approach to generating a suitable host cell with inducible recombinase expression. Use of other host cells is contemplated according to certain embodiments, which may vary depending on the particular mammalian immunoglobulin genes that are employed or for other reasons, including a human cell, a non-human primate cell, a camelid cell, a hamster cell, a mouse cell, a rat cell, a rabbit cell, a canine cell, a feline cell, an equine cell, a bovine cell and an ovine cell.

Alternatively, only one of the RAG-1, or RAG-2 genes may be stably integrated into a host cell, and the other gene can be introduced by transfection to regulate whether or not recombination can take place. For example, a cell line that is stably transfected with TdT and RAG-2 would be recombinationally silent. Upon transient transfection with RAG-1, or viral infection with RAG-1, the cell lines would become recombinationally active. The skilled person will appreciate from these illustrative examples that other similar approaches may be used to control the onset of recombination in a host cell.

Another approach may be to use specific small interfering RNA (siRNA) to repress the expression in a host cell of RAG-1 and/or RAG-2 by RNA interference (RNAi) (including specific siRNAs the biosynthesis of which within a cell may be directed by introduced encoding DNA vectors having regulatory elements for controlling siRNA production), and then to relieve such repression when it is desired to induce recombination.

For instance, in certain such embodiments a cell line in which active RAG-1- and/or RAG-2-specific siRNA expression is present will be recombinationally silent. Activation of recombination occurs when RAG-1- and/or RAG-2-specific siRNA expression is shut off or repressed. Regulation of such siRNA expression may be achieved using inducible systems like the Tet system or other similar expression-regulating components. These include the Tet/on and Tet/off system (Clontech Inc., Palo Alto, Calif.), the Regulated Mammalian Expression system (Promega, Madison, Wis.), and the GeneSwitch System (Invitrogen Life Technologies, Carlsbad, Calif.). Alternatively, host cells may be transfected with an expression vector that encodes a repressing protein that prevents transcription of the inhibiting RNA.

In yet another alternative embodiment according to which RAG-1- and/or RAG-2-specific siRNA expression may regulate the recombination competence of the host cell, deletion of the introduced siRNA encoding sequences by use of the Cre/Lox recombinase system (e.g., Sauer, 1998 *Methods* 14:381; Kaczmarczyk et al., 2001 *Nucleic Acids Res* 29:E56; Sauer, 2002 *Endocrine* 19:221; Kondo et al., 2003 *Nucleic Acids Res* 31:e76) may also permit activation of recombination mechanisms. Activation of recombination capability in a host cell may also be achieved by transfecting or infecting an expression construct containing the repressed gene with modified codons so that it is not inhibited by the siRNA molecules.

Substantial impairment of the expression of one or more recombination control elements (e.g., a RAG-1 gene, or RAG-2 gene) may be achieved by any of a variety of methods that are well known in the art for blocking specific gene expression, including antisense inhibition of gene expression, ribozyme mediated inhibition of gene expression, siRNA mediated inhibition of gene expression, cre recombinase regulation of expression control elements using the Cre/Lox system in the design of constructs encoding one or more recombination control elements, or other molecular regulatory strategies. As used herein, expression of a gene encoding a recombination control element is substantially impaired by any such method for inhibiting when host cells are substantially but not necessarily completely depleted of functional DNA or functional mRNA encoding the recombination control element, or of the relevant RAG-1, or RAG-2 polypeptide. Recombination control element expression is substantially impaired when cells are preferably at least 50% depleted of DNA or mRNA encoding the endogenous RAG-1, and/or RAG-2 polypeptide (as detected using high stringency hybridization) or 50% depleted of detectable RAG-1 and/or RAG-2 polypeptide (e.g., as measured by Western immunoblot); and more preferably at least 75% depleted of detectable RAG-1, and/or RAG-2 polypeptide. Most preferably, recombination control element expression is substantially impaired when host cells are depleted of >90% of their endogenous RAG-1 and/or RAG-2 DNA, mRNA, or polypeptide.

It will be appreciated that certain embodiments disclosed herein relate to the use of nucleic vectors for the assembly of the nucleic acid compositions for generating immunoglobulin structural diversity, and also for RAG-1, RAG-2 and/or TdT gene expression and for regulatory constructs such as siRNA regulators of RAG-1, RAG-2 and/or TdT expression. A wide variety of suitable nucleic acid vectors are known in the art and may be employed as described or according to conventional procedures, including modifications, as described for example in Sambrook et al., Molecular Cloning: A Laboratory Manual, Cold Spring Harbor Laboratories, Cold Spring Harbor, N.Y., 1989; Ausubel et al., Current Protocols in Molecular Biology, Greene Publ. Assoc. Inc. & John Wiley & Sons, Inc., Boston, Mass., 1993); Maniatis et al. (Molecular Cloning, Cold Spring Harbor Laboratory, Plainview, N.Y., 1982) and elsewhere.

Other vectors that may be adapted for use according to certain herein disclosed embodiments include those described by Choi, S. & Kim, U. J. (2001) 175:57-68; Fabb, S. A. & Ragoussis, J. (1995) *Mol Cell Biol Hum Dis Ser* 5:104-24; Monaco, Z. L. & Moralli, D. (2006). *Biochem Soc Trans* 34:324-7; Ripoll et. al. (1998). *Gene* 210:163-72. Also contemplated are the use of protoplast fusion systems such as those described by Caporale et. al. (1990). *Gene* 87:285-9; Ferguson et. al. (1986). *J Biol Chem* 261:14760-3, Sandri-Goldin et. al. (1981). *Mol Cell Biol* 1:743-52; and yeast artificial chromosome (YAC) spheroblast fusion as described by Davies, N. P. and Huxley, C. (1996). *Methods Mol Biol* 54:281-92; Gnirke et. al (1991). *Embo J* 10:1629-34; Ikeno et. al. (1998). *Nat Biotechnol* 16:431-9; Jakobovits, A et. al. (1993). *Nature* 362:255-8; Pavan et. al. (1990). *Mol Cell Biol* 10:4163-9. In preferred embodiments the nucleic acid compositions for generating immunoglobulin structural diversity as provided herein are stably integrated into host cell chromosomes using known methodologies and where such integration can be confirmed according to established techniques (e.g., Sambrook et al., 1989; Ausubel et al., 1993; Maniatis et al. 1982). Related embodiments contemplate chromosomal EBV elements that mediate integration, and other embodiments contemplate extrachromosomal maintenance of natural or artificial centromere-containing constructs.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the vector (e.g., an expression vector) is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding an immunoglobulin region.

In certain preferred embodiments the expression control sequence is a "regulated promoter", which may be a promoter as provided herein and may also be a repressor binding site, an activator binding site or any other regulatory sequence that controls expression of a nucleic acid sequence as provided herein. In certain particularly preferred embodiments the regulated promoter is a tightly regulated promoter that is specifically inducible and that permits little or no transcription of nucleic acid sequences under its control in the absence of an induction signal, as is known to those familiar with the art and described, for example, in Guzman et al. (1995 *J.*

*Bacteriol.* 177:4121), Carra et al. (1993 *EMBO J.* 12:35), Mayer (1995 *Gene* 163:41), Haldimann et al. (1998 *J. Bacteriol.* 180:1277), Lutz et al. (1997 *Nuc. Ac. Res.* 25:1203), Allgood et al. (1997 *Curr. Opin. Biotechnol.* 8:474) and Makrides (1996 *Microbiol. Rev.* 60:512), all of which are hereby incorporated by reference. In other preferred embodiments of the invention a regulated promoter is present that is inducible but that may not be tightly regulated. In certain other preferred embodiments a promoter is present in the recombinant expression construct of the invention that is not a regulated promoter; such a promoter may include, for example, a constitutive promoter such as an insect polyhedrin promoter. The expression construct also contains a ribosome binding site for translation initiation and a transcription terminator. The vector may also include appropriate sequences for amplifying expression.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the immunoglobulin polypeptides or fusion proteins. Such retroviral vector particles then may be employed, to transduce eukaryotic cells, either in vitro or in vivo. The transduced eukaryotic cells will express the nucleic acid sequence(s) encoding the immunoglobulin polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

As described herein, certain embodiments relate to compositions that are capable of delivering nucleic acid molecules comprising mammalian immunoglobulin gene regions and/or encoding immunoglobulin fusion proteins. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264:16985-16987, 1989) and lipid-DNA combinations (see Felgner et al., *Proc. Natl. Acad. Sci. USA* 84:7413-7417, 1989).

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of immunoglobulin or immunoglobulin fusion expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*). Additional methods include spheroplast fusion and protoplast fusion.

Nucleic Acids

The nucleic acids of the present invention, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an immunoglobulin or a region thereof (e.g., a V region, a D segment, a J region, a C region, etc.) or an immunoglobulin fusion polypeptide for use according to the present embodiments may be identical to the coding sequence known in the art for any given immunoglobulin gene regions or fusion polypeptide domains (e.g., membrane anchor domains, extracellular domain-associating polypeptides, etc.), or may be a different coding sequence, which, as a result of the redundancy or degeneracy of the genetic code, encodes the same immunoglobulin region or fusion polypeptide.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons), and may also include regulatory elements (e.g., promoters, enhancers, repressor binding sites and the like), and may also include recombination signal sequences (RSSs) as described herein.

The nucleic acids for use according to the embodiments described herein may include, but are not limited to: only the coding sequence for an immunoglobulin or immunoglobulin fusion polypeptide; the coding sequence for the immunoglobulin or immunoglobulin fusion polypeptide and additional coding sequence; the coding sequence for the immunoglobulin or immunoglobulin fusion polypeptide (and optionally additional coding sequence) and non-coding sequence, such as introns or non-coding sequences 5' and/or 3' of the coding sequence for the immunoglobulin or immunoglobulin fusion polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" or "polynucleotide encoding" an immunoglobulin or immunoglobulin fusion protein encompasses a nucleic acid which includes only coding sequence for an immunoglobulin or immunoglobulin fusion polypeptide as well as a nucleic acid which includes additional coding and/or non-coding sequence(s).

Nucleic acids and oligonucleotides for use as described herein can be synthesized by any method known to those of skill in this art (see, e.g., WO 93/01286, U.S. application Ser. No. 07/723,454; U.S. Pat. No. 5,218,088; U.S. Pat. No. 5,175, 269; U.S. Pat. No. 5,109,124). Identification of oligonucleotides and nucleic acid sequences for use in the present invention involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

As known in the art "similarity" between two polypeptides is determined by comparing the amino acid sequence and conserved amino acid substitutes thereto of the polypeptide to the sequence of a second polypeptide. Fragments or portions of the nucleic acids encoding polypeptides of the present invention may be used to synthesize full-length nucleic acids of the present invention. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 *Nucl. Ac. Res.* 25:3389) which weights sequence gaps and sequence mismatches according to the default weightings provided by the National Institutes of Health/NCBI database (Bethesda, Md.; see ncbi.nlm.nih.gov/cgi-bin/BLAST/nph-newblast).

Determination of the three-dimensional structures of representative polypeptides (e.g., immunoglobulins, membrane anchor domain polypeptides, specific protein-protein association domains, etc.) may be made through routine methodologies such that substitution of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007). Some additional non-limiting examples of computer algorithms that may be used for these and related embodiments, such as for rational design of membrane anchor domains or specific protein-protein association domains as provided herein, include Desktop Molecular Modeler (See, for example, Agboh et al., *J. Biol. Chem.,* 279, 40: 41650-57 (2004)), which allows for determining atomic dimensions from spacefilling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488).

A truncated molecule may be any molecule that comprises less than a full length version of the molecule. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

In other preferred embodiments, truncated molecules are polypeptides that comprise less than the full length amino acid sequence of a particular protein or polypeptide component. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues. In certain particularly preferred embodiments truncated nucleic acid molecules may have a deletion of 270-330 contiguous nucleotides. In certain other particularly preferred embodiments truncated polypeptide molecules may have a deletion of 80-140 contiguous amino acids.

The present invention further relates to variants of the herein referenced nucleic acids which encode fragments, analogs and/or derivatives of an immunoglobulin or immunoglobulin fusion polypeptide. The variants of the nucleic acids encoding such polypeptides may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded polypeptide.

Variants and derivatives of immunoglobulin or immunoglobulin fusion polypeptide may be obtained by mutations of nucleotide sequences encoding such polypeptides or any portion thereof. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest. An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed by the invention. For example, sequences encoding Cys residues that are not desirable or essential for biological activity can be altered to cause the Cys residues to be deleted or replaced with other amino acids, preventing formation of incorrect or undesirable intramolecular disulfide bridges upon renaturation.

Immunoglobulins

As described herein and as also known in the art, immunoglobulins comprise products of a gene family the members of which exhibit a high degree of sequence conservation, such that amino acid sequences of two or more immunoglobulins or immunoglobulin domains or regions or portions thereof (e.g., VH domains, VL domains, hinge regions, CH2 constant regions, CH3 constant regions) can be aligned and analyzed to identify portions of such sequences that correspond to one another, for instance, by exhibiting pronounced sequence homology. (See, e.g., Kabat et al., *Sequences of Proteins of Immunological Interest*, Edition: 5, 1992 DIANE Publishing, 1992, Darby, Pa.; Tomlinson et al., 1992 *J Mol Biol* 227:776; Milner et al., 1995 *Ann N Y Acad Sci* 764:50.) Determination of sequence homology may be readily determined with any of a number of sequence alignment and analysis tools, including computer algorithms well known to those of ordinary skill in the art, such as Align or the BLAST algorithm (Altschul, *J. Mol. Biol.* 219:555-565, 1991; Henikoff and Henikoff, *Proc. Natl. Acad. Sci. USA* 89:10915-10919, 1992), which is available at the NCBI website (ncbi.nlm.nih.gov/cgi-bin/BLAST). Default parameters may be used.

Portions of a particular immunoglobulin reference sequence and of any one or more additional immunoglobulin sequences of interest that may be compared to the reference sequence are regarded as "corresponding" sequences, regions, fragments or the like, based on the convention for numbering immunoglobulin amino acid positions according to Kabat, *Sequences of Proteins of Immunological Interest*, ($5^{th}$ ed. Bethesda, Md.: Public Health Service, National Institutes of Health (1991)). For example, according to this convention, the immunoglobulin family to which an immunoglobulin sequence of interest belongs is determined based on conservation of variable region polypeptide sequence invariant amino acid residues, to identify a particular numbering system for the immunoglobulin family, and the sequence(s) of interest can then be aligned to assign sequence position numbers to the individual amino acids which comprise such sequence(s). Preferably at least 70%, more preferably at least 80%-85% or 86%-89%, and still more preferably at least 90%, 92%, 94%, 96%, 98% or 99% of the amino acids in a given amino acid sequence of at least 1000, more preferably 700-950, more preferably 350-700, still more preferably 100-350, still more preferably 80-100, 70-80, 60-70, 50-60, 40-50 or 30-40 consecutive amino acids of a sequence, are identical to the amino acids located at corresponding positions in a reference sequence such as those disclosed by Kabat et al. (1991) or Kabat et al. (1992) or in a similar compendium of related immunoglobulin sequences, such as may be generated from public databases (e.g., Genbank, SwissProt, etc.) using sequence alignment tools as described above. In certain preferred embodiments, an immunoglobulin sequence of interest or a region, portion, derivative or fragment thereof is greater than 95% identical to a corresponding reference sequence, and in certain preferred embodiments such a sequence of interest may differ from a corresponding reference at no more than 1, 2, 3, 4, 5, 6, 7, 8, 9 or 10 amino acid positions.

Human immunoglobulin gene libraries are currently generated by any number of techniques with which those having ordinary skill in the art will be familiar. Such methods include but are not limited to, Epstein Barr Virus (EBV) transformation of human peripheral blood cells (e.g., containing B lymphocytes), in vitro immunization of human B cells, fusion of spleen cells from immunized transgenic mice carrying human immunoglobulin genes inserted by yeast artificial chromosomes (YAC), isolation from human immunoglobulin V region phage libraries, or other procedures as known in the art and based on the disclosure herein. See, e.g., U.S. Pat. No. 5,877,397; Bruggemann et al., 1997 *Curr. Opin. Biotechnol.* 8:455-58; Jakobovits et al., 1995 *Ann. N.Y. Acad. Sci.* 764: 525-35. In the described human immunoglobulin gene-carrying transgenic mice, human immunoglobulin heavy and light chain genes have been artificially introduced by genetic engineering in germlne configuration, and the endogenous murine immunoglobulin genes have been inactivated. See, e.g., Bruggemann et al., 1997 *Curr. Opin. Biotechnol.* 8:455-58. For example, human immunoglobulin transgenes may be mini-gene constructs, or transloci on yeast artificial chromosomes, which undergo B cell-specific DNA rearrangement and hypermutation in the mouse lymphoid tissue. See, Bruggemann et al., 1997 *Curr. Opin. Biotechnol.* 8:455-58.

According to certain embodiments, structurally diverse non-human, human, or humanized immunoglobulin heavy chain and/or light chain variable regions such as can be generated using the compositions and methods disclosed herein, may be constructed as single chain Fv (sFv) polypeptide fragments (single chain antibodies). See, e.g., Bird et al., 1988 *Science* 242:423-426; Huston et al., 1988 *Proc. Natl. Acad. Sci. USA* 85:5879-5883. Multi-functional sFv fusion proteins may be generated by linking a polynucleotide sequence encoding an sFv polypeptide in-frame with at least one polynucleotide sequence encoding any of a variety of known effector proteins. These methods are known in the art, and are disclosed, for example, in EP-B1-0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., 1995 *J. Immunol. Methods* 188:1-7. Other examples of effector proteins are enzymes. As a non-limiting example, such an enzyme may provide a biological activity for therapeutic purposes (see, e.g., Siemers et al., 1997 *Bioconjug Chem.* 8:510-19), or may provide a detectable activity, such as horseradish peroxidase-catalyzed conversion of any of a number of well-known substrates into a detectable product, for diagnostic uses. Still other examples of sFv fusion proteins include Ig-toxin fusions, or immunotoxins, wherein the sFv polypeptide is linked to a toxin. Those having ordinary skill in the art will appreciate that a wide variety of polypeptide sequences have been identified that, under appropriate conditions, are toxic to cells. As used herein, a toxin polypeptide for inclusion in an immunoglobulintoxin fusion protein may be any polypeptide capable of being introduced to a cell in a manner that compromises cell survival, for example, by directly interfering with a vital function or by inducing apoptosis. Toxins thus may include, for example, ribosome-inactivating proteins, such as *Pseudomonas aeruginosa* exotoxin A, plant gelonin, bryodin from *Bryonia dioica*, or the like. See, e.g., Thrush et al., 1996 *Annu. Rev. Immunol.* 14:49-71; Frankel et al., 1996 *Cancer Res.* 56:926-32. Numerous other toxins, including chemotherapeutic agents, antimitotic agents, antibiotics, inducers of apoptosis (or "apoptogens", see, e.g., Green and Reed, 1998, *Science* 281:1309-1312), or the like, are known to those familiar with the art, and the examples provided herein are intended to be illustrative without limiting the scope and spirit of the invention.

A sFv may be fused to peptide or polypeptide domains that permit detection of specific binding between the fusion protein and a desired antigen. For example, the fusion polypeptide domain may be an affinity tag polypeptide. Binding of the sFv fusion protein to a binding partner (e.g., an antigen of interest such as a diagnostic or therapeutic target molecule) may therefore be detected using an affinity polypeptide or peptide tag, such as an avidin, streptavidin or a H is (e.g., polyhistidine) tag, by any of a variety of techniques with which those skilled in the art will be familiar. Detection techniques may also include, for example, binding of an avidin or streptavidin fusion protein to biotin or to a biotin mimetic sequence (see, e.g., Luo et al., 1998 *J. Biotechnol.* 65:225 and references cited therein), direct covalent modification of a fusion protein with a detectable moiety (e.g., a labeling moiety), noncovalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support.

The following Examples are presented by way of illustration and not limitation.

EXAMPLES

Example 1

Specific Constructs for the Recombination Control Elements and Mediators of Junctional Diversity This Example describes the sequences of the recombination control elements and mediators of junctional diversity [SEQ ID NOS:1-6]. These elements were codon optimized (Geneart, Inc., Toronto, Canada) for translation in mammalian cells and contain 5' HindIII and 3' XbaI restriction sites to facilitate cloning into expression vectors containing CMV or SV40 promoters. The RAG-1 polynucleotide [SEQ ID NO:1]

encodes human RAG-1 polypeptide [SEQ ID NO:2], and was gene optimized for expression in mammalian cells. The translation product of this construct was identical to the deduced translation of RAG-1 mRNA in the Genbank database (NM_000448). The polynucleotide sequence is provided in SEQ ID NO:1 and the amino acid sequence is provided in SEQ ID NO:2. The RAG-2 polynucleotide [SEQ ID NO:3] encodes the human RAG-2 polypeptide [SEQ ID NO:4], and was codon optimized (Geneart, Inc., Toronto, Canada) for expression in mammalian cells. The translation product of this construct was identical to the deduced translation of RAG-2 mRNA in the Genbank database (NM_000536). The polynucleotide sequence is provided in SEQ ID NO:3 and the amino acid sequence is provided in SEQ ID NO:4. ITS-5 [SEQ ID NO:5] encoded human TdT, codon optimized (Geneart, Inc., Toronto, Canada) for expression in mammalian cells. The translation product of ITS-5 was identical to the deduced translation of TdT mRNA in the Genbank sequence (NM_004088). The polynucleotide sequence is provided in SEQ ID NO:5 and the amino acid sequence is provided in SEQ ID NO:6. RAG-1 and RAG-2 were cloned into pcDNA3.1(+) (Invitrogen, Carlsbad, Calif.) and were shown to mediate VDJ recombination (described below).

Example 2

RAG-1/RAG-2 Mediated Recombination

Figure 3:
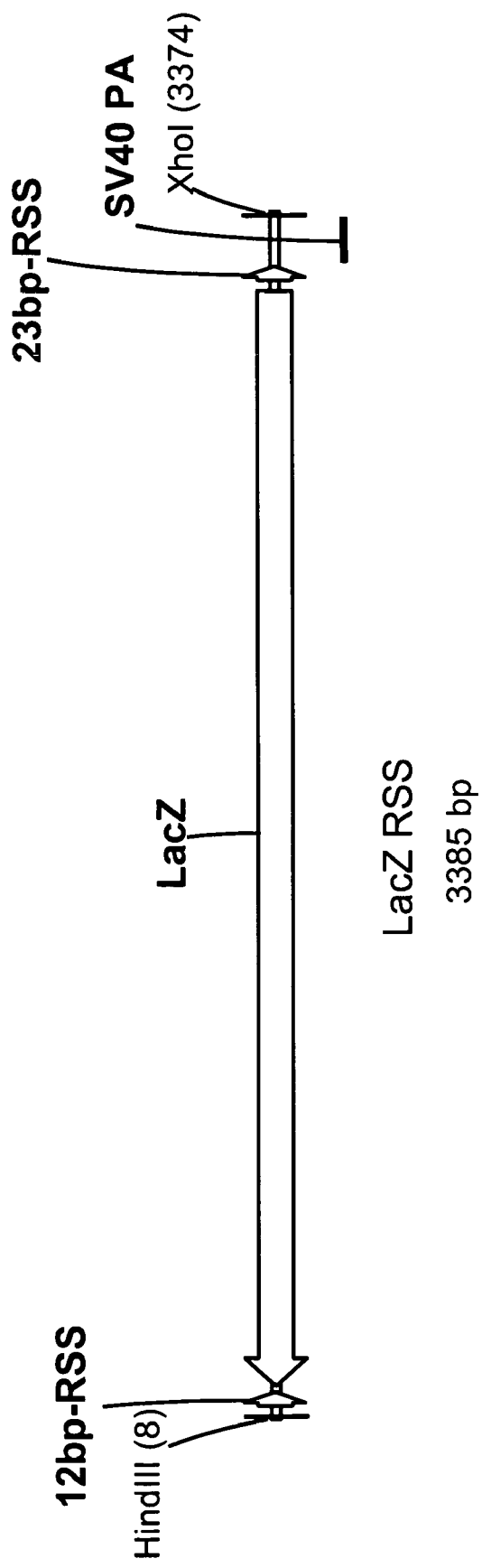
FIG. 3 shows a schematic diagram of the LacZ-RSS. The RSS with the 12 base pair recombination signal sequence and the RSS with the 23 base pair recombination signal sequence are positioned in the same orientation. The HindIII-XhoI fragment of LacZ-RSS was inserted into pcDNA3.1(+) so that the LacZ open reading frame is in the opposite orientation relative to the CMV promoter to create vector V25. V25 is an inversional VDJ substrate.

RAG-1/RAG-2 mediated recombination was targeted through cis recombination signal sequences (RSS). DNA containing the *E. coli* LacZ gene flanked by RSS sequences was custom synthesized by Geneart Inc. (Toronto, Canada) with HindIII and XhoI ends for subsequent cloning (LacZ-RSS, SEQ ID NO:7). A recombination substrate vector, V25, was generated by cloning the HindIII/XhoI restriction fragment containing coding sequence for the beta-galactosidase reporter flanked by upstream and downstream RSSs, LacZ-RSS, into plasmid vector pcDNA3.1(+) (Invitrogen, Carlsbad, Calif.). FIG. 3 shows a schematic diagram of LacZ-RSS. The polynucleotide sequence of LacZ-RSS is provided in SEQ ID NO:7 and the translated amino acid sequence is provided in SEQ ID NO:8. The recombination substrate encoded the bacterial enzyme LacZ (beta-galactosidase) and was codon optimized for expression in mammalian cells, such that the LacZ was flanked by two recombination signal sequences in the same orientation. The sequences of the RSSs were as follows:

```
12-bp RSS:
                                    [SEQ ID NO: 18]
CACAGTGCTCCAGGGCTGAACAAAAACC 23-bp RSS:
                                    [SEQ ID NO: 19]
CACAGTGGTAGTACTCCACTGTCTGGGTGTACAAAACC
```

The LacZ coding sequence was initially in the reverse orientation relative to the CMV promoter and thus no beta-galactosidase was expressed when the vector was transected into cells. An SV40 polyadenylation signal next to the 23-bp RSS ensured that unintended expression of lacZ was minimal prior to recombination. In the presence of RAG-1/RAG-2, the orientation of the LacZ coding sequence was reversed since the recombination signals were in the same orientation, generating an inversional event. Following recombination LacZ coding sequence was placed in the same orientation as the CMV promoter and beta-galactosidase was expressed. Beta-galactosidase enzymatic activity expressed by cells that had undergone RAG-1/RAG-2 mediated recombination was assayed with colorimetric β-gal substrates, by enzyme linked immunosorbent assay (ELISA) and by microscopy.

The RAG-1 and RAG-2 constructs were confirmed to mediate recombination using the following procedure. 293-H cells were transfected according to the supplier's recommendations (Invitrogen, Carlsbad, Calif., Cat. No. 11631-017). Cells were seeded at 20,000 cells/well in a tissue culture treated 96-well plate and incubated overnight. The next day, cells were transfected with Lipofectamine 2000 (Invitrogen, Carlsbad, Calif., Cat. No. 11668-019) according to the manufacturer's recommendations. Cells were transfected with 67 ng of the LacZ-RSS plasmid, 0 or 33 ng of the RAG-2 plasmid and 0, 8, 17, 33 or 67 ng of the RAG-1 plasmid. Carrier plasmid was added such that all samples received the same total amount of DNA. Two days after transfection, cell lysates were prepared and beta-galactosidase activity was determined using the calorimetric substrate chlorophenol red-β-D-galactopyranoside (Sigma, St. Louis, Mo., Cat. No. 59767-25MG-F).

Figure 4:
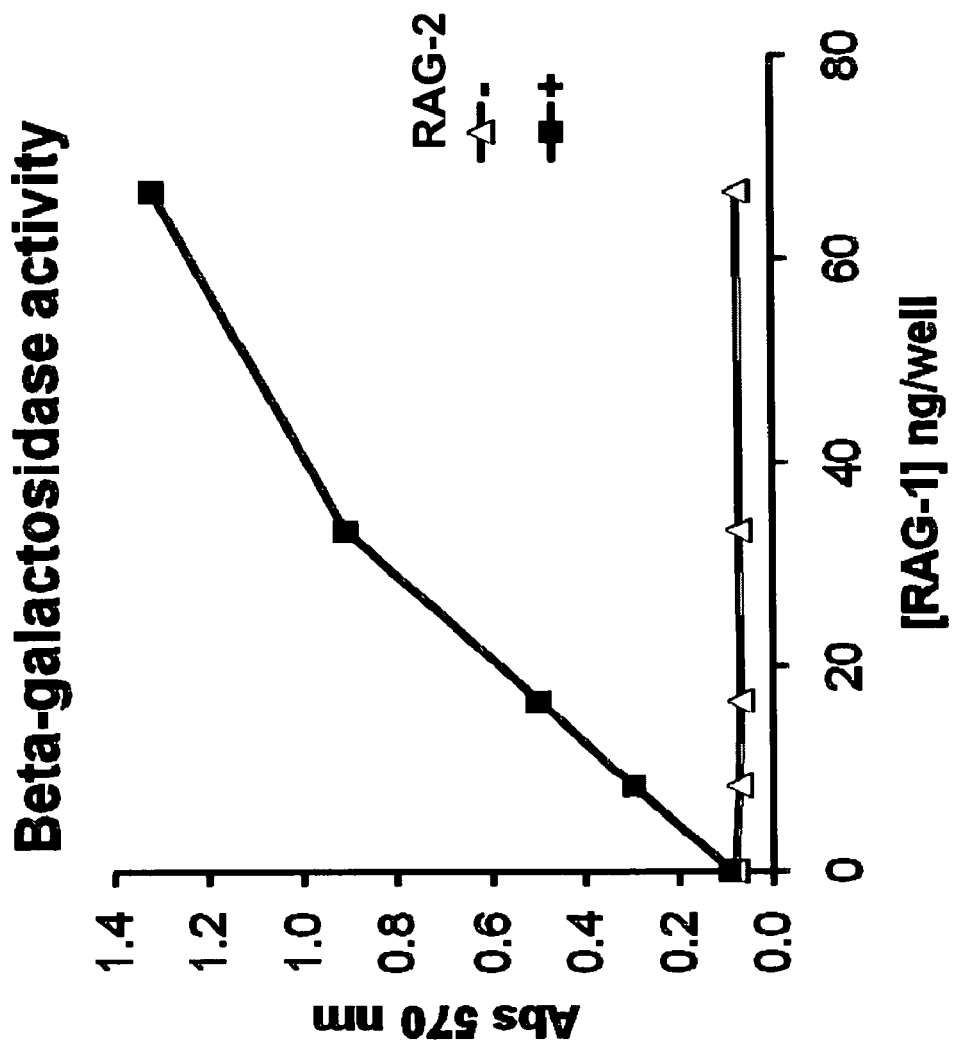
FIG. 4 shows RAG-1/RAG-2 mediated recombination of a β-gal substrate (LacZ-RSS). 293 Cells were transfected with 67 ng of the LacZ-RSS plasmid, 0 (diamonds) or 33 ng (squares) of the RAG-2 plasmid and 0, 8, 17, 33 or 67 ng of the RAG-1 plasmid. Carrier plasmid was added such that all samples received the same total amount of DNA. Two days after transfection, cell lysates were prepared and beta-galactosidase activity was determined using the calorimetric substrate chlorophenol red-β-D-galactopyranoside (Sigma, St. Louis, Mo., Cat. No. 59767-25MG-F).

The results shown in FIG. 4 demonstrated that recombination was dependent on the expression of both RAG-1 and RAG-2. The figure also shows that recombination activity increased with increasing amounts of the RAG-1 plasmid during the transfection step.

Example 3

RAG-1/RAG-2 Induced Recombination of an Integrated Substrate

A stable cell line integrated with the recombination substrate V25, prepared as described above (e.g., Example 2), was generated by transfection of HEK-293 cells with Lipofectamine™ 2000 according to the manufacturer's instructions (Invitrogen, Carlsbad, Calif.). Stable pools of transfected cells were selected using 1 mg/ml G418. Stably selected cell pools were subsequently split into a 96 well plate and 24 hours later wells were transiently transfected with equal amounts of the RAG1 and RAG2 expression vectors (RAG-1 and RAG-2 coding sequences, respectively, cloned into pcDNA3.1(+) (Invitrogen, Carlsbad, Calif.). Forty-eight hours following transfection cells were fixed and stained for beta-galactosidase activity according to the manufacturer's instructions (Cat. # K1465-01, Invitrogen, Carlsbad, Calif.), by which a detectable blue stain indicates beta-galactosidase activity.

Staining was allowed to proceed overnight. There were no blue cells observed amongst 293 cells that were stably integrated with V25 but that had not been transiently transfected with RAG-1 and RAG-2. Amongst 293 cells that were stably integrated with V25 and transiently transfected with RAG-1 and RAG-2, blue stained cells were readily detectable by light microscopy, with multiple blue stained cells observed per field. The results demonstrated that recombination of the integrated substrate was successfully induced by the transient expression of RAG-1 and RAG-2.

Example 4

Diversifying an Immunoglobulin Heavy Chain

An antibody (immunoglobulin) molecule is a heterodimer comprised of two subunits, a heavy chain and a light chain. This example demonstrates the assembly of intact antibodies as the result of the recombination of surface Ig heavy chain encoding VDJ recombination substrates in HEK-293 cells transiently expressing RAG-1 and RAG-2 and the human kappa light chain.

Figure 5:
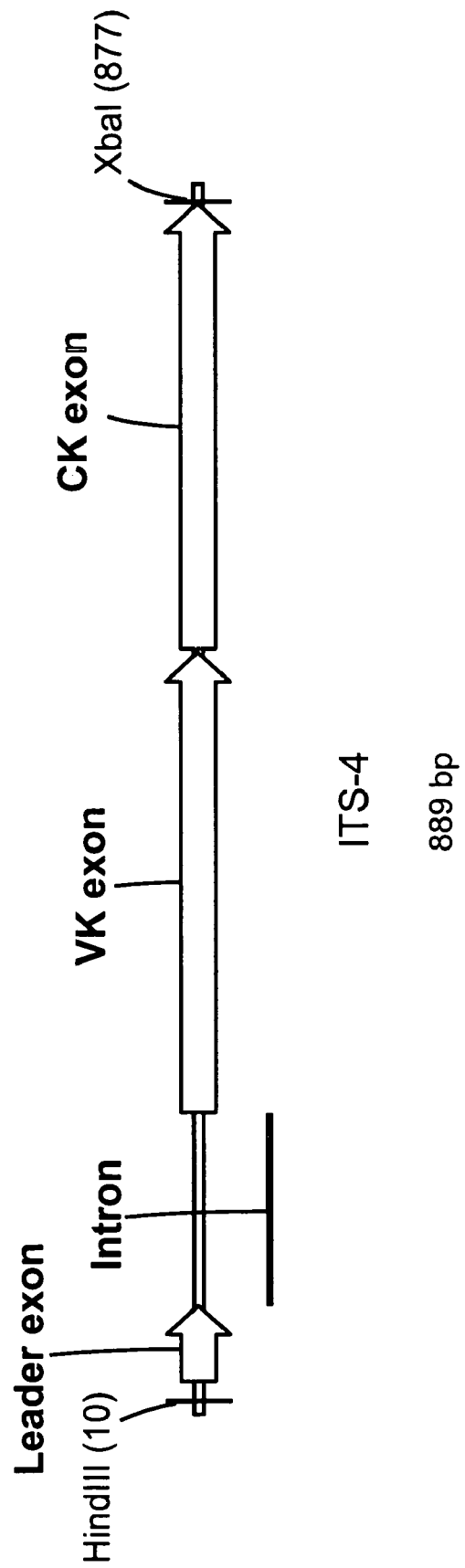
FIG. 5 shows a schematic diagram of ITS-4, a vector encoding a functional immunoglobulin kappa antibody light chain protein.

A light chain vector encoding a functional immunoglobulin kappa chain was prepared containing a leader exon, an intron, a V kappa exon and a constant kappa exon, and was designated ITS-4. The sequence of the constant region was based on the Genebank sequence NG_000834. The entire coding sequence was codon optimized (Geneart, Inc., Toronto, Canada) for expression in mammalian cells. FIG. 5 shows a schematic diagram of ITS-4. The polynucleotide sequence is provided in SEQ ID NO:9 and the amino acid sequence is provided in SEQ ID NO:10.

Figure 6:
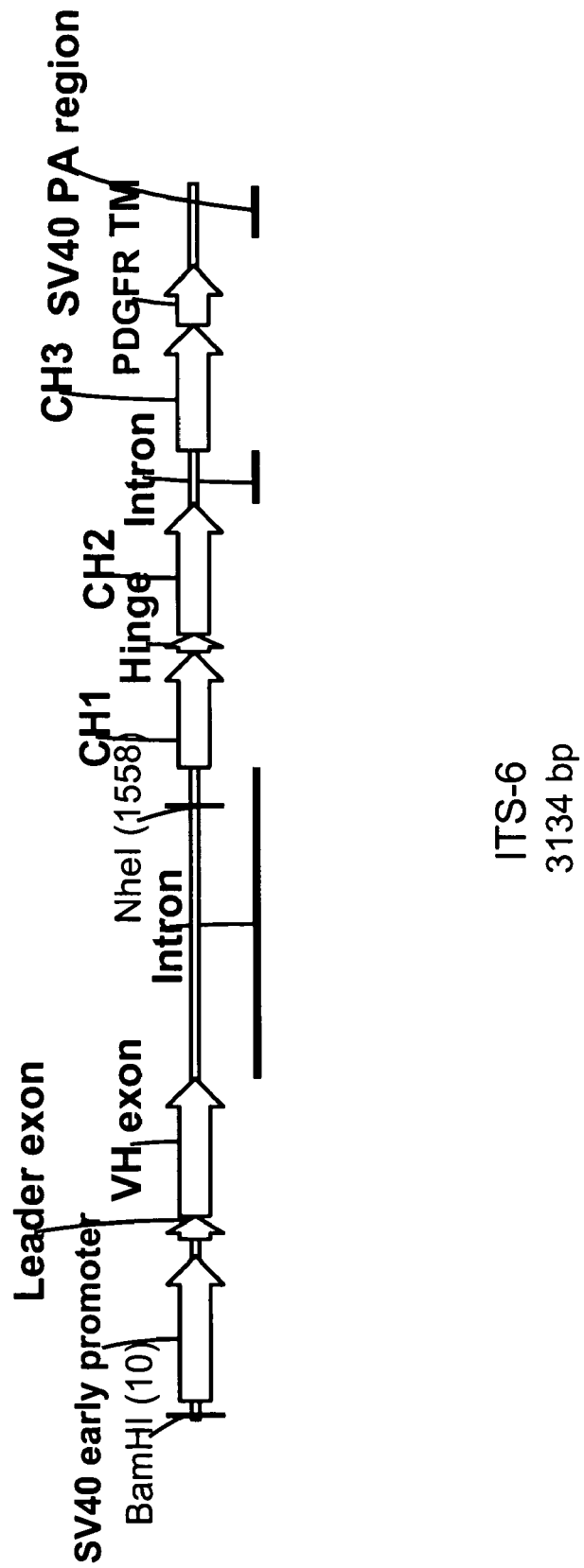
FIG. 6 shows a schematic diagram of ITS-6, a vector encoding a functional immunoglobulin IgG heavy chain membrane-expressed protein.

A heavy chain vector designed to express IgG on the surface of the cell was also generated, and designated ITS-6. ITS-6 [SEQ ID NO:11] encoded a functional human IgG1 antibody heavy chain [SEQ ID NO:12] that localized to the cell surface and was anchored to the plasma membrane by a transmembrane domain derived from the human platelet derived growth factor receptor (PDGFR). A schematic diagram of ITS-6 is shown in FIG. 6. Expression was driven by a SV40 promoter. An SV40 polyadenylation signal was present at the downstream (3') end of the construct. There were two introns in the construct, one between the VDJH exon (preassembled heavy chain exon) and the CH1 exon, and the other between the CH2 exon and the CH3 exon. The restriction enzyme sites BamHI and NheI facilitated substitution of the variable domain for VDJ substrates. Transfection of HEK-293 cells with both ITS-6 and ITS-4 (co-transfection) resulted in human IgG expressed on the surface of cells. The ITS-6 vector was the backbone for all additional tripartite antibody diversification vectors. The polynucleotide sequence of ITS-6 is provided in SEQ ID NO:11 and the amino acid sequence is provided in SEQ ID NO:12.

The vector ITS-6 [SEQ ID NO:6] was modified to remove the functional antibody encoding sequences and replace them with VH gene segments with appropriate recombination signal sequences (RSSs), D gene segments with and appropriate RSSs, and J gene segments with appropriate RSSs, to create recombination vectors designated V64 [SEQ ID NOS:14-15], V67 [SEQ ID NO:16] and V86 [SEQ ID NO:17]. In each vector, each V segment had an upstream SV40 early promoter and a downstream 23-bp RSS in the forward orientation. The D segments each had an upstream 12-bp RSS in the reverse orientation and a downstream 12-bp RSS in the forward orientation. The J segments had an upstream 23-bp RSS in the reverse orientation and a downstream splice donor site. The sequences of the 12-bp and 23-bp RSSs were as follows:

```
12-bp RSS:
                                  [SEQ ID NO: 20]
CACAGTGGTACAGACCAATACAAAAACC 23-bp RSS:
                                  [SEQ ID NO: 19]
CACAGTGGTAGTACTCCACTGTCTGGGTGTACAAAAACC
```

Figure 7:
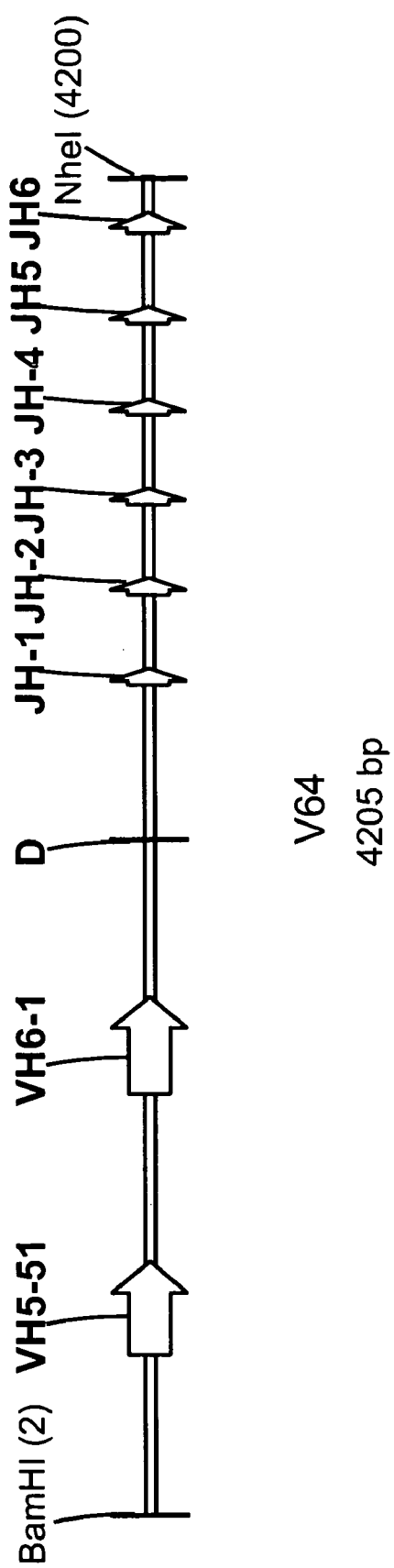
FIG. 7 shows a schematic diagram of V64, a tripartite immunoglobulin diversifying vector with a 2:1:6 (V:D:J) ratio.

V64 encoded a VDJ heavy chain recombination substrate consisting of two V segments, a single D segment and six J segments (schematic diagram shown in FIG. 7). The sequences of two V64 variants are shown in SEQ ID NO:14 and SEQ ID NO:15, each having a different D segment. In these two variants, each V segment had an upstream SV40 early promoter and a downstream 23-bp RSS in the forward orientation. The D segment had an upstream 12-bp RSS in the reverse orientation and a downstream 12-bp in the forward orientation. The J segments each had an upstream 23-bp RSS in the reverse orientation and a downstream splice donor site. The sequences of the 12-bp and 23-bp RSSs were as follows:

```
Upstream V64.1 12-bp RSS
                                  SEQ ID NO: 21
CACATAGCAGGAGGGCCTTCACAAAAAGC Downstream V64.1 12-bp RSS
                                  SEQ ID NO: 22
CACAGTGATGAACCCAGCAGCAAAAACT Upstream V64.3 12-bp RSS
                                  SEQ ID NO: 23
CACAGTAGGAGGGGCCTTCACAAAAAGC Downstream V64.3 12-bp RSS
                                  SEQ ID NO: 24
CACAGTGATGAAACTAGCAGCAAAAACT 23-bp RSS (all)
                                  SEQ ID NO: 19
CACAGTGGTAGTACTCCACTGTCTGGGTGTACAAAAACC
```

Vector V67 encoded a VDJ heavy chain recombination substrate having one V segment, a single D segment and six J segments. The V segment had an upstream SV40 early promoter and a downstream 23-bp RSS in the forward orientation. The D segment had an upstream 12-bp RSS in the reverse orientation and a downstream 12-bp in the forward orientation. The J segments each had an upstream 23-bp RSS in the reverse orientation and a downstream splice donor site. The sequence of the 12-bp and 23-bp RSSs were as follows:

```
Upstream 12-bp RSS:
                                  [SEQ ID NO: 25]
CACATAGCAGGAGGGCCTTCACAAAAAGC Downstream 12-bp RSS:
                                  [SEQ ID NO: 26]
CACAGTGATGAACCCAGCAGCAAAAACT 23-bp RSS (all):
                                  [SEQ ID NO: 19]
CACAGTGGTAGTACTCCACTGTCTGGGTGTACAAAAACC
```

Figure 8:
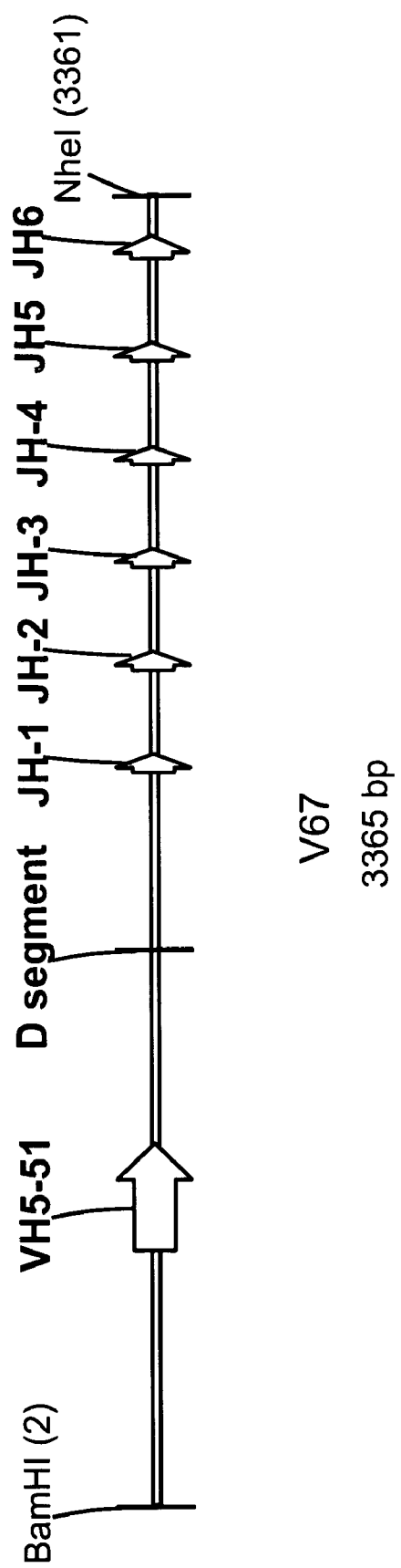
FIG. 8 shows a schematic diagram of V67, a tripartite immunoglobulin diversifying vector with a 1:1:6 (V:D:J) ratio.
Figure 9:
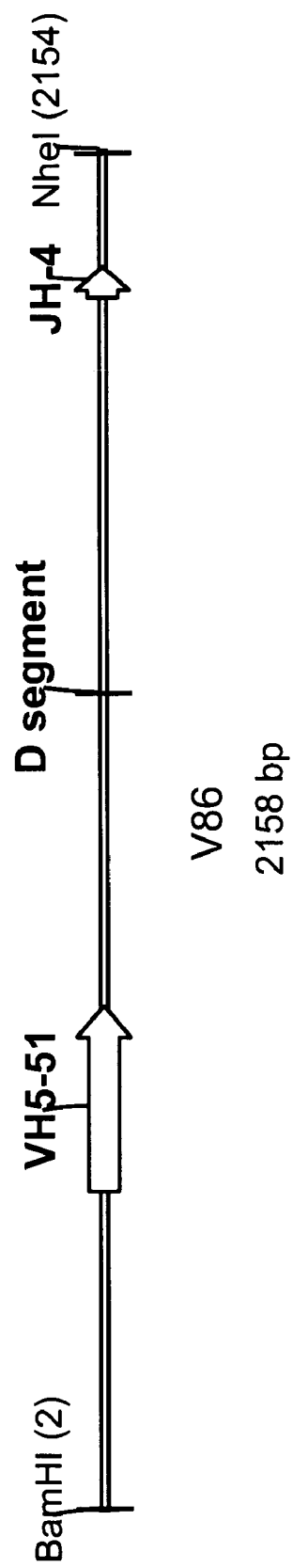
FIG. 9 shows a schematic diagram of V86, a tripartite immunoglobulin diversifying vector with a 1:1:1 (V:D:J) ratio.

A schematic diagram of V67 is shown in FIG. 8. The sequence is shown in SEQ ID NO:16.

Another antibody generating substrate, V86, encoded a heavy chain recombination substrate having one V segment, one D segment and one J segment. The V segment had an upstream SV40 early promoter and a downstream 23-bp RSS in the forward orientation. The D segment had an upstream 12-bp RSS in the reverse orientation and a downstream 12-bp in the forward orientation. The J segment had an upstream 23-bp RSS in the reverse orientation and a downstream splice donor site. The sequences of the 12-bp and 23-bp RSSs were as follows:

```
Upstream 12-bp RSS:
                                  SEQ ID NO: 27
CACATAGCAGGAGGGCCTTCACAAAAAGC Downstream 12-bp RSS:
                                  SEQ ID NO: 28
CACAGTGATGAACCCAGCAGCAAAAACT
```

A schematic diagram of V86 is shown in FIG. 12. The V86 sequence is shown in SEQ ID NO:17. The antibody generation vectors V67 and V86 were shown to generate a membrane expressed antibody when co-transfected with RAG-1, RAG-2 and a human kappa chain antibody.

Briefly, 293-HEK cells were split 1:4 into 10 cm² dishes 24 hours prior to transfection. Transfection was performed with Lipofectamine™ 2000 (Invitrogen, cat #11668-019) per the manufacturer's suggested protocol. The heavy chain recombining vector (12.0 µg), V67 or V86, was transfected with an equal mass of DNA representing a 1:1:1:1 ratio of RAG-1, RAG-2, ITS-4 and V25, respectively. V25 was included as an internal control for recombination. In addition to the heavy chain recombining substrates (V67 or V86), ITS-6 was also transfected as a positive control. 72 hours post-transfection, media were aspirated and the cells were washed 1× with 5 ml of PBS and then detached using 1 ml of 0.1× trypsin for 5 minutes at room temperature. Following this 5-minute incubation, the trypsin was neutralized with 8 ml of DMEM supplemented with 10% FBS. The cells were then transferred to a 15 ml conical vial and centrifuged at approximately 800 g for 5 minutes. Media were then aspirated and the cells were resuspended in 500 ul of PBS containing 2% FBS (staining buffer) transferred to a 1.5 ml microcentrifuge tube and centrifuged for an additional 2 minutes at 3000 rpm. Media were then aspirated and the cells were resuspended in 200 µl of staining buffer with 1:200 dilution of a Goat-anti-Human IgG H+L–PE conjugated polyclonal antibody (Cedarlane, Burlington, N.C., Cat. #109-115-098, stock concentration 0.5 µg/ml). The cells were incubated on ice for 1 hour and then washed 2 times with 200 µl PBS and finally resuspended into 100 µl of staining buffer. Positive cells were visualized by fluorescence microscopy and quantified using flow cytometry (Table 3).

TABLE 3

Immunocytofluorimetric Detection of Surface Ig Positive (sIg+) Transfectants

| Vector Name | Description | Surface Ig Positive Events | |
|---|---|---|---|
| | | # of Events | % Positive |
| V2 | Empty vector | 476 | 0.05% |
| ITS-6 | Recombined Heavy Chain | 26824 | 27.82% |
| V67 | 1V-1D-6J substrate | 1486 | 0.15% |
| V86 | 1V-1D-1J substrate | 1074 | 0.11% |

Transfection with the control ITS-6 vector showed that a large fraction of cells expressed membrane human IgG1. Transfection with V67 and V86 each showed a low percentage of positive cells. Although these frequencies were relatively low, fluorescent cells were visualized under the microscope for each vector (V67 and V86).

In a separate experiment, stable cell lines were generated using the V64.1 and V64.3 substrates (described above). HEK-293H cells were transfected with equal amounts of five expression plasmids using Lipofectamine 2000 (Invitrogen, Cat. #11668-019) as per the manufacturer's suggested protocol. The vectors included: 1) RAG1, 2) RAG2, 3) V64, (2V-1D-6J), heavy chain VDJ substrate, 4) a fully recombined antibody light chain (ITS-4) and 5) a vector containing the puromycin resistance gene. Forty-eight hours post-transfection, cells were selected using 1.0 ug/ml puromycin for 2 weeks. Puromycin resistant clones were then plucked and expanded into 6 well dishes. Once the cells had achieved confluence, media were aspirated and the cells were washed 1× with 2 ml of PBS and then detached using 0.5 ml of 0.1× trypsin for 5 minutes at room temperature. Following the 5 minute incubation the trypsin was neutralized with 2 ml of DMEM supplemented with 10% FBS. Half of the cells were then transferred to a 1.5 ml microcentrifuge tube and spun at 3000 rpm for 2 minutes. Media were then aspirated and the cells were resuspended in 200 ul of PBS containing 2% FBS (staining buffer) with 1:200 dilution of a Goat anti-Human IgG H+ L–PE conjugated polyclonal antibody (Cedarlane, Cat #109-115-098, stock concentration 0.5 ug/ml). The cells were incubated at 4 degree Celsius for 1 hr and then washed 2 times with 150 ul PBS, then resuspended into 100 ul of staining buffer. Positive cells were visualized using fluorescent microscopy and quantified using flow cytometry (Table 4).

The transfection resulted in host cells containing chromosomally integrated, fully assembled (e.g., rearranged relative to the germline) and functional immunoglobulin light chain gene that was constitutively expressed (ITS-4). The stable cell line also expressed RAG-1 and RAG-2 and a heavy chain diversity generating vector(s) encoding an Ig fusion protein having a membrane anchor domain as described herein (V64). The light chain was secreted and was not found on the cell surface unless associated with a membrane-associating heavy chain. Cells that did not produce Ig heavy chain gene VDJ events, or that generated out-of-frame products, were not able to generate a heavy chain. Cells that did produce a functionally rearranged heavy chain gene were able to assemble the expressed heavy chain in association with the light chain and so generated a membrane bound antibody, due to the membrane anchoring domains included in the heavy chain diversity generating vector. Clones of 293 cells harboring integrated V64 (2V-1 D-6J) VDJ substrates were analyzed by FACS (10,000 cells analyzed). A number of clones were identified that expressed human IgG on the cell surface of a significant number of cells (Table 5). Immunofluorescence microscopy readily permitted visualization of cells with fluorescently stained human IgG on their surfaces.

TABLE 4

Immunocytofluorimetric Detection of Surface Ig Positive (sIg+) Transfectants by Fluorescence Activated Cell Sorter (FACS) Analysis

| Filename | Clone ID | Description | % Surface Ig Positive Cells |
|---|---|---|---|
| Specimen_001_1.fcs | 1 | V64.3 clone 1 | 0.2% |
| Specimen_001_4_003.fcs | 7 | V64.3 clone 7 | 5.4% |
| Specimen_001_4_012.fcs | 16 | V64.1 clone 8 | 8.2% |
| Specimen_001_4_021.fcs | 25 | V64.1 clone 17 | 10.5% |
| Specimen_001_4_023.fcs | 27 | V64.1 clone 19 | 3.1% |

With such demonstrated expression of the antibody product of VDJ recombination on the cell surface, antigen-binding or anti-Ig binding assays can be performed to identify cells expressing Ig heavy chains having desired binding properties.

It should be appreciated that in related alternative embodiments, the above described process can be conducted with a stably integrated immunoglobulin heavy chain gene in the host cell, into which are introduced light chain diversity generating vectors assembled as described herein. A rearranged heavy chain gene recovered from a host cell expressing an immunoglobulin having desired binding properties and identified as described above in this Example, can be integrated into a host cell and subsequently a light chain diversity generating vector can be used. For example and according to non-limiting theory, by this approach both the heavy chain and the light chain CDR3s are selected for a desired binding activity (e.g., specific binding to a desired antigen) to generate high affinity antibodies.

Example 5

Diversifying Both Heavy and Light Chains in a Single Host Cell

This Example describes introducing Ig heavy and light chain diversification constructs into the same host cell. In order to avoid the recombination signals from the two constructs being utilized inappropriately (e.g., $V_H$ to $J_L$ etc.) it is preferred to have the constructs introduced sequentially so that they integrate into different chromosomes. A trans-chromosomal recombination event between the two constructs is not impossible but kinetically the intrachromosomal recombination event is favored. At least one D segment gene is present on each nucleic acid construct for generating immunoglobulin diversity, so that all V and J gene segments (both heavy chain and light chain) contain the same RSS spacer size (i.e., 12 or 23 nucleotide signals as described above) whilst the D segment gene contains the functionally complementary RSS spacer size (i.e., 23 nt if V and J use 12 nt; 12 nt if V and J use 23 nt); this configuration precludes direct V to J recombination events.

Including the D segment gene on the Ig light chain diversity construct promotes the generation of a diverse light chain repertoire. Again, because of the 12/23 rule it prevents direct V to J recombination. In the in vitro system, which does not contain the regulatory controls found in vivo that terminate recombination following the successful completion of a functional light chain gene assembly, multiple rounds of light chain recombination transpire until either the expression of the recombinase is stopped or all the light chain V and J gene segments are consumed. In either event significant biases are observed and proximal V and J genes (e.g., V region genes further from the 5' terminus and J segment genes further from the 3' terminus) are more frequently deleted and under-utilized.

The tripartite V-D-J assembly process for Ig light chain gene recombination promotes an unprecedentedly diverse light chain repertoire. The D segment encoding polynucleotides of the D segment gene(s) include natural D segment encoding gene sequences found in the human genome and/or artificial D segment encoding sequences.

In a preferred embodiment artificial D segment genes having D segment encoding polynucleotide sequences with between 1 and 6 nucleotides predominantly containing a "G" or "C" are included so as to mimic the biased addition of TdT. Because N nucleotide addition is generally lower at the light chain locus and deletions occur at both the 5' and 3' ends of the D segment encoding sequence, the remaining G/C nucleotides are functionally equivalent to TdT additions and provide additional diversity at the light chain locus. The products from larger species of such D-like segments with high G/C content thus represent the functional equivalents of larger N nucleotide insertions.

Although an artificial D segment encoding sequence having one or only a few nucleotides (e.g., 2, 3, 4, 5) is likely on a probabilistic basis to be eliminated by deletion accompanying recombination, low probability successful recombination events that utilize the D segment encoding sequence enhance light chain sequence diversity, and delusional events that eliminate the D segment still contribute to reduced positional (e.g., 5' or 3') bias in the usage of light chain V and J gene segments in productive recombination.

Another nucleic acid composition for generating Ig structural diversity includes three D segment genes on a light chain diversity generating construct: 3' to the V region genes is a first D segment encoding gene having the nucleotide sequence 5'-(GCGC)-3' situated between a first D segment upstream RSS and a first D segment downstream RSS; downstream from the first D segment encoding gene is a second D segment encoding gene having a single "G" nucleotide situated between a second D segment upstream RSS and a second D segment downstream RSS; downstream from the second D segment encoding gene is a third D segment encoding gene that is proximal to a J segment gene and that has the nucleotide sequence 5'-(GGCGCC)-3' situated between a third D segment upstream RSS and a third D segment downstream RSS. In this exemplary light chain diversity-generating composition, D segment encoding sequences are separated by sequences that are also found separating D segment genes of the heavy chain locus in the human genome.

REFERENCES

Azuma et al., 1976 *J Biochem* 80:1023; Alt et al., 1984 *Embo J* 3:1209; Chaney et al., 1986 *Somat Cell Mol Genet.* 12:237; Caporale et al., 1990 *Gene* 87:285; Alessandrini et al., 1991 *Mol Cell Biol* 11:2096; Akamatsu et al., 1994 *J Immunol* 153:4520; Bradshaw et al., 1995 *Nucleic Acids Res* 23:4850; Connor et al., 1995 *J Immunol* 155:5268; Corbett et al., 1997 *J Mol Biol* 270:587; Sauer, 1998 *Methods* 14:381; Arakawa et al., 2001 *BMC Biotechnol* 1:7; Choi et al., 2001 *Methods Mol Biol* 175:57; Chowdhury et al., 2001 *Embo J* 20:6394; Kaczmarczyk et al., 2001 *Nucleic Acids Res* 29:E56; Sauer, 2002 *Endocrine* 19:221; Bruce et al., 2003 *Rna* 9:1264; Cowell et al., 2003 *J Exp Med* 197:207; Kondo et al., 2003 *Nucleic Acids Res* 31:e76; Chatterjee et al., 2004 *Nucleic Acids Res* 32:5668; Chowdhury et al., 2004 *Immunol Rev* 200:182; Ciubotaru et al., 2004 *Mol Cell Biol* 24:8727; Cowell et al., 2004 *Immunol Rev* 200:57; Arnaout, 2005 *BMC Genomics* 6:148; Afshar et al., 2006 *J Immunol* 176:2439; Baird et al., 2006 *Rna* 12:1755; Browman et al., 2007 *Trends Cell Biol* 17:394; Chakraborty et al., 2007 *Mol Cell* 27:842; Chen et al., 2007 *Faseb J* 21:2931; Ferguson et al., 1986 *J Biol Chem* 261:14760; Engler et al., 1987 *Proc Natl Acad Sci USA* 84:4949; Galli et al., 1988 *Proc Natl Acad Sci USA* 85:2439; Ferrier et al., 1990 *Embo J* 9:117; Gnirke et al., 1991 *Embo J* 10:1629; Gauss et al., 1992 *Nucleic Acids Res* 20:6739; Gauss et al., 1992 *Genes Dev* 6:1553; Gauss et al., 1993 *Mol Cell Biol* 13:3900; Gerstein et al., 1993 *Genes Dev* 7:1459; Ezekiel et al., 1995 *Immunity* 2:381; Fabb et al., 1995 *Mol Cell Biol Hum Dis Ser* 5:104; Davies et al., 1996 *Methods Mol Biol* 54:281; Dul et al., 1996 *J Immunol* 157:2969; Eastman et al., 1996 *Nature* 380:85; Fanning et al., 1996 *Immunogenetics* 44:146; Gauss et al., 1996 *Mol Cell Biol* 16:258; Eastman et al., 1997 *Nucleic Acids Res* 25:4370; Ezekiel et al., 1997 *Mol Cell Biol* 17:4191; Delassus et al., 1998 *J Immunol* 160:3274; Frank et al., 1998 *Nature* 396:173; Gauss et al., 1998 *Eur J Immunol* 28:351; Grawunder et al., 1998 *J Biol Chem* 273:24708; Eastman et al., 1999 *Mol Cell Biol* 19:3788; Fugmann et al., 2000 *Annu Rev Immunol* 18:495; Gellert, 2002 *Annu Rev Biochem* 71:101; Dai et al., 2003 *Proc Natl Acad Sci USA* 100:2462; De et al., 2004 *Mol Cell Biol* 24:6850; Espinoza et al., 2005 *J Immunol* 175:6668; Drejer-Teel et al., 2007

Mol Cell Biol 27:6288; Horne et al., 1982 *J Immunol* 129: 660; Hamel et al., 1987 *J Immunol* 139:3012; Hesse et al., 1987 *Cell* 49:775; Hoeijmakers et al., 1987 *Exp Cell Res* 169:111; Koiwai et al., 1987 *Biochem Biophys Res Commun* 144:185; Kojima et al., 1987 *Biochem Biophys Res Commun* 143:716; Ichihara et al., 1988 *Embo J* 7:4141; Hesse et al., 1989 *Genes Dev* 3:1053; Hendrickson et al., 1991 *Proc Natl Acad Sci USA* 88:4061; Huang et al., 1992 *J Clin Invest* 89:1331; Ichihara et al., 1992 *Immunol Lett* 33:277; Kim, U. J. et al., 1992 *Nucleic Acids Res* 20:1083; Jakobovits et al., 1993 *Nature* 362:255; Knarr et al., 1995 *J Biol Chem* 270:27589; Huxley, 1997 *Trends Genet.* 13:345; Julicher et al., 1997 *Genomics* 43:95; Hikida et al., 1998 *J Exp Med* 187:795; Ikeno et al., 1998 *Nat Biotechnol* 16:431; Kim, S.Y. et al., 1998 *Genome Res* 8:404; Hesslein et al., 2001 *Adv Immunol* 78:169; Holowka et al., 2001 *Semin Immunol* 13:99; Kaczmarczyk et al., 2001 *Nucleic Acids Res* 29:E56; Jones et al., 2003 *Proc Natl Acad Sci USA* 100:15446; Jung et al., 2003 *Immunity* 18:65; Kondo et al., 2003 *Nucleic Acids Res* 31:e76; Harder, 2004 *Curr Opin Immunol* 16:353; Ko et al., 2004 *J Biol Chem* 279: 7715; Hayashi et al., 2005 *Life Sci* 77:1612; Ivanov et al., 2005 *J Immunol* 174:7773; Kapitonov et al., 2005 *PLoS Biol* 3:e181; Heaney et al., 2006 *Mamm Genome* 17:791; Inlay et al., 2006 *J Exp Med* 203:1721; Jung et al., 2006 *Annu Rev Immunol* 24:541; Heckmann et al., 2007 *Methods Enzymol* 426:463; Hillion et al., 2007 *J Immunol* 179: 6790; Hillion et al., 2007 *Autoimmun Rev* 6:415; Meyerowitz et al., 1980 *Gene* 11:271; Landau et al., 1987 *Mol Cell Biol* 7:3237; Lee et al., 1999 *Immunity* 11:771; Lieber et al., 1987 *Genes Dev* 1:751; McCormick et al., 1987 *Methods Enzymol* 151:397; Lieber et al., 1988 *Cell* 55:7; Lieber et al., 1988 *Proc Natl Acad Sci USA* 85:8588; Lewis, 1994 *Proc Natl Acad Sci USA* 91:1332; Lieber et al., 1994 *Semin Immunol* 6:143; Lonberg et al., 1994 *Nature* 368: 856; Lilie et al., 1995 *J Mol Biol* 248:190; Lonberg et al., 1995 *Int Rev Immunol* 13:65; Mattila et al., 1995 *Eur J Immunol* 25:2578; Livak et al., 1996 *Mol Cell Biol* 16:609; Leu et al., 1997 *Immunity* 7:303; Livak et al., 1997 *J Mol Biol* 267:1; Larijani et al., 1999 *Nucleic Acids Res* 27:2304; Modesti et al., 1999 *Embo J* 18:2008; Maes et al., 2000 *J Immunol* 165:703; Moshous et al., 2000 *Hum Mol Genet* 9:583; Mageed et al., 2001 *Clin Exp Immunol* 123:1; Moshous et al., 2001 *Cell* 105:177; Larin et al., 2002 *Trends Genet* 18:313; Ma et al., 2002 *Cell* 108:781; Lee et al., 2003 *PLoS Biol* 1:E1; Market et al., 2003 *PLoS Biol* 1:E16; Martin et al., 2003 *J Immunol* 171:4663; Montalbano et al., 2003 *J Immunol* 171:5296; Morshead et al., 2003 *Proc Natl Acad Sci USA* 100:11577; Moshous et al., 2003 *Ann N Y Acad Sci* 987:150; Le Deist et al., 2004 *Immunol Rev* 200:142; Li et al., 2005 *J Immunol* 174:2420; London, 2005 *Biochim Biophys Acta* 1746:203; Maes et al., 2006 *J Immunol* 176:5409; Masuda et al., 2006 *Febs J* 273:2184; Masumoto et al., 2006 *Tanpakushitsu Kakusan Koso* 51:2155; Monaco et al., 2006 *Biochem Soc Trans* 34:324; Lu et al., 2007 *Nucleic Acids Res* 35:6917; Lantelme et al., 2008 *Mol Immunol* 45:328; Ravetch et al., 1981 *Cell* 27:583; Peterson et al., 1984 *Proc Natl Acad Sci USA* 81:4363; Reth, M. G. et al., 1985 *Nature* 317:353; Rinfret et al., 1985 *J Immunol* 135:2574; Padlan et al., 1986 *Mol Immunol* 23:951; Reth, M. G. et al., 1986 *Embo J* 5:2131; Reth, M. et al., 1987 *Embo J* 6:3299; Pavan et al., 1990 *Mol Cell Biol* 10:4163; Ramsden et al., 1991 *Proc Natl Acad Sci USA* 88:10721; Rathbun et al., 1993 *Int Immunol* 5:997; Ramsay, 1994 *Mol Biotechnol* 1:181; Rolink et al., 1995 *Semin Immunol* 7:155; Pan et al., 1997 *Int Immunol* 9:515; Raaphorst et al., 1997 *Int Immunol* 9:1503; Roch et al., 1997 *Nucleic Acids Res* 25:2303; Nadel et al., 1998 *J Exp Med* 187:1495; Ohmori et al., 1998 *Crit Rev Immunol* 18:221; Ripoll et al., 1998 *Gene* 210: 163; Nitschke et al., 2001 *J Immunol* 166:2540; Rooney et al., 2002 *Mol Cell* 10:1379; Oberdoerffer et al., 2003 *Nucleic Acids Res* 31:e140; Roose et al., 2003 *PLoS Biol* 1:E53; Poinsignon et al., 2004 *J Exp Med* 199:315; Repasky et al., 2004 *J Immunol* 172:5478; Reddy et al., 2006 *Genes Dev* 20:1575; Sandri-Goldin et al., 1981 *Mol Cell Biol* 1:743; Schatz et al., 1988 *Cell* 53:107; Schroeder et al., 1988 *Proc Natl Acad Sci USA* 85:8196; Sauer et al., 1990 *New Biol* 2:441; Yamada et al., 1991 *J Exp Med* 173:395; Schatz et al., 1992 *Annu Rev Immunol* 10:359; Seto et al., 1992 *Nucleic Acids Res* 20:3786; Solin et al., 1992 *Immunogenetics* 36:306; Taylor et al., 1992 *Nucleic Acids Res* 20:6287; Shapiro et al., 1993 *Mol Cell Biol* 13:5679; Tuaillon et al., 1993 *Proc Natl Acad Sci USA* 90:3720; Wei et al., 1993 *J Biol Chem* 268:3180; Schlissel et al., 1994 *J Immunol* 153:1645; Slightom et al., 1994 *Gene* 147:77; Woo et al., 1994 Nucleic Acids Res 22:4922; Schatz, 1997 Semin Immunol 9:149; Sauer, 1998 Methods 14:381; Skowronek et al., 1998 *Proc Natl Acad Sci USA* 95:1574; Tuaillon et al., 1998 *Proc Natl Acad Sci USA* 95:1703; Yu, C. C. et al., 1998 *J Immunol* 161:3444; Sun et al., 1999 *Mol Immunol* 36:551; Yu, K. et al., 1999 *Mol Cell Biol* 19:8094; Soderlind et al., 2000 *Nat Biotechnol* 18:852; Tevelev et al., 2000 *J Biol Chem* 275:8341; Tuaillon et al., 2000 *J Immunol* 164:6387; Tuaillon et al., 2000 *Eur J Immunol* 30:2998; Shizuya et al., 2001 *Keio J Med* 50:26; Wang et al., 2001 *Genome Res* 11:137; Williams et al., 2001 *J Immunol* 167:257; Sauer, 2002 Endocrine 19:221; Schlissel, 2002 Cell 109:1; Tsai et al., 2002 *Genes Dev* 16:1934; Verkaik et al., 2002 *Eur J Immunol* 32:701; Yu, Y. et al., 2003 *DNA Repair (Amst)* 2:1239; Yurchenko et al., 2003 *Genes Dev* 17:581; Schatz, 2004 Immunol Rev 200:5; Shockett et al., 2004 *Mol Immunol* 40:813; Souto-Carneiro et al., 2004 *J Immunol* 172:6790; That et al., 2004 *J Immunol* 173:4009; Wollscheid et al., 2004 *Subcell Biochem* 37:121; Schatz et al., 2005 *Curr Top Microbiol Immunol* 290:49; Schelonka et al., 2005 *J Immunol* 175: 6624; Spicuglia et al., 2006 *Curr Opin Immunol* 18:158; Suarez et al., 2006 *Mol Immunol* 43:1827; Semprini et al., 2007 *Nucleic Acids Res* 35:1402; Takada et al., 2007 *Genome Biol* 8:215; VanDyk et al., 1996 *J. Immunol* 157: 4005-4015; Vanura et al., 2007 *PLoS Biol* 5:e43; Zheng et al., 2007 *Mol Immunol* 44:2221; Zou et al., 2007 *Chin Med J (Engl)* 120:410.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08012714B2). An electronic copy of the "Sequence Listing" will also be available from the USPTO upon request and payment of the fee set forth in 37 CFR 1.19(b)(3).

What is claimed is:

1. An isolated host cell that is capable of in vitro immunoglobulin gene rearrangement and which comprises a first nucleic acid composition for generating immunoglobulin structural diversity comprising a tripartite recombination substrate, wherein the tripartite recombination substrate comprises:
    (a) a first nucleic acid that comprises one or a plurality of mammalian immunoglobulin heavy chain variable ($V_H$) region genes each operably linked to an expression control sequence, each $V_H$ region gene consisting essentially of (i) an isolated immunoglobulin $V_H$ region encoding polynucleotide sequence, and (ii) a non-endogenous $V_H$ region recombination signal sequence that is located 3' to the isolated immunoglobulin $V_H$ region encoding polynucleotide sequence;
    (b) a second nucleic acid that comprises one or a plurality of mammalian immunoglobulin heavy chain diversity (D) segment genes, each of said immunoglobulin D segment genes consisting essentially of (i) an isolated D segment encoding polynucleotide sequence, (ii) a D segment upstream recombination signal sequence that is located 5' to each of said D segment encoding polynucleotide sequences and that is capable of functional recombination with the non-endogenous $V_H$ region recombination signal sequence, and (iii) a D segment downstream recombination signal sequence that is located 3' to each of said isolated D segment encoding polynucleotide sequences; and
    (c) a third nucleic acid that comprises one or a plurality of mammalian immunoglobulin heavy chain joining ($J_H$) segment genes, each of said immunoglobulin $J_H$ segment genes consisting essentially of (i) an isolated $J_H$ segment encoding polynucleotide sequence in operable linkage to an immunoglobulin heavy chain constant ($C_H$) region gene, and (ii) a non-endogenous $J_H$ segment recombination signal sequence that is located 5' to the $J_H$ segment encoding polynucleotide sequence and that is capable of functional recombination with the D segment downstream recombination signal sequence of (b)
    wherein the first nucleic acid composition is integrated in the isolated host cell and wherein the tripartite recombination substrate can undergo at least two or more recombination events in any order in the isolated host cell to form a recombined polynucleotide that encodes an immunoglobulin heavy chain polypeptide, and wherein the isolated host cell expresses said immunoglobulin heavy chain polypeptide.

2. The isolated host cell of claim 1 wherein the first nucleic acid composition further comprises a fourth nucleic acid that comprises a polynucleotide sequence encoding a membrane anchor domain polypeptide operably linked to said tripartite recombination substrate, and wherein said immunoglobulin heavy chain polypeptide comprises a membrane anchor domain.

3. The isolated host cell of either claim 1 or claim 2 wherein in the tripartite recombination substrate:
    (a) (i) the mammalian immunoglobulin $V_H$ region genes and the mammalian immunoglobulin heavy chain D segment genes are present at a ratio of about 1:1 to 1:2, and (ii) the mammalian immunoglobulin $J_H$ segment genes and the mammalian immunoglobulin heavy chain D segment genes are present at a ratio of about 1:1 to 1:2;
    (b) the mammalian immunoglobulin $V_H$ region genes and the mammalian immunoglobulin $J_H$ segment genes are present at a ratio of about 1:2 (V to J) to 2:1 (V to J);
    (c) the one or a plurality of mammalian immunoglobulin $V_H$ region genes, together with the one or a plurality of mammalian immunoglobulin $J_H$ segment genes, are not greater in number than the mammalian immunoglobulin heavy chain D segment genes; or
    (d) there are 6, 7, 8, 9, 10, 11 or 12 mammalian immunoglobulin heavy chain D segment genes.

4. The isolated host cell of either claim 1 or claim 2 wherein:
    (a) the first nucleic acid comprises 12-50 contiguous $V_H$ region genes of which about 10% to about 30% of said $V_H$ region genes that are contiguous with a 5'-most located $V_H$ region gene each comprise a $V_H$ region RSS of low or medium RSS efficiency, and about 70% to about 90% of said $V_H$ region genes that are contiguous with a 3'-most located $V_H$ region gene each comprise a $V_H$ region RSS of high RSS efficiency; and
    (b) the second nucleic acid comprises a plurality of contiguous D segment genes of which about 80% to about 90% of said D segment genes that are contiguous with a 5'-most located D segment gene each comprises a D segment upstream RSS of high RSS efficiency and a D segment downstream RSS of high RSS efficiency, and about 10% to about 20% of said D segment genes that are contiguous with a 3'-most located D segment gene each comprises a D segment upstream RSS of low or medium RSS efficiency and a D segment downstream RSS of low or medium RSS efficiency, wherein (i) the plurality of $V_H$ region genes, together with (ii) the one or a plurality of $J_H$ segment genes, are not greater in number than said plurality of D segment genes.

5. The isolated host cell of either claim 1 or claim 2 that is characterized by one or more of:
    (a) the first nucleic acid comprises 12-50 contiguous $V_H$ region genes of which about 10% to about 30% of said $V_H$ region genes that are contiguous with a 5'-most located $V_H$ region gene each comprise a $V_H$ region RSS of low or medium RSS efficiency;

(b) the first nucleic acid comprises 12-50 contiguous $V_H$ region genes of which about 70% to about 90% of said $V_H$ region genes that are contiguous with a 3'-most located $V_H$ region gene each comprise a $V_H$ region RSS of high RSS efficiency;

(c) the second nucleic acid comprises a plurality of contiguous D segment genes of which about 80% to about 90% of said D segment genes that are contiguous with a 5'-most located D segment gene each comprise a D segment upstream RSS of high RSS efficiency and a D segment downstream RSS of high RSS efficiency; and (d) the second nucleic acid comprises a plurality of contiguous D segment genes of which about 10% to about 20% of said D segment genes that are contiguous with a 3'-most located D segment gene each comprise a D segment upstream RSS of low or medium RSS efficiency and a D segment downstream RSS of low or medium RSS efficiency.

6. The isolated host cell of claim 2 wherein the membrane anchor domain polypeptide comprises a polypeptide that is selected from the group consisting of a transmembrane domain polypeptide, a glycosyl-phosphatidylinositol-linkage polypeptide, a lipid raft-associating polypeptide and a specific protein-protein association domain polypeptide.

7. The isolated host cell of claim 1 wherein the first nucleic acid composition comprises the first, second, and third nucleic acids joined in operable linkage as a single nucleic acid molecule.

8. The isolated host cell of claim 1 wherein the first, second, and third nucleic acids are joined in operable linkage in a vector.

9. The isolated host cell of claim 8 wherein the vector is selected from the group consisting of a viral vector, a plasmid, a cosmid, a transposon and an artificial chromosome.

10. The isolated host cell of either claim 1 or claim 2 wherein the mammalian immunoglobulin $V_H$ gene is selected from the group consisting of a human $V_H$ gene, a mouse $V_H$ gene, a rat $V_H$ gene, a rabbit $V_H$ gene, a canine $V_H$ gene, a feline $V_H$ gene, an equine $V_H$ gene, a bovine $V_H$ gene, a monkey $V_H$ gene, a baboon $V_H$ gene, a macaque $V_H$ gene, a chimpanzee $V_H$ gene, a gorilla $V_H$ gene, an orangutan $V_H$ gene, a camel $V_H$ gene, a llama $V_H$ gene, an alpaca $V_H$ gene and an ovine $V_H$ gene.

11. The isolated host cell of either claim 1 or claim 2 wherein the tripartite recombination substrate is under control of at least one operably linked recombination control element.

12. The isolated host cell of claim 11 wherein the recombination control element is an inducible recombination control element.

13. The isolated host cell of claim 12 wherein the inducible recombination control element is tightly regulated.

14. The isolated host cell of either claim 1 or 2 wherein the cell is selected from the group consisting of a human cell, a non-human primate cell, a camelid cell, a hamster cell, a mouse cell, a rat cell, a rabbit cell, a canine cell, a feline cell, an equine cell, a bovine cell and an ovine cell.

15. The isolated host cell of claim 1 or claim 2 wherein the expression control sequence is selected from the group consisting of a constitutive promoter, a regulated promoter, a repressor binding site and an activator binding site.

16. The isolated host cell of claim 15 wherein the regulated promoter is selected from the group consisting of a tightly regulated promoter and an inducible promoter.

17. A method for generating structural diversity in one or a plurality of immunoglobulin heavy chain variable (VH) region genes, comprising, maintaining the isolated host cell of either claim 1 or claim 2 under conditions and for a time sufficient for the tripartite recombination substrate to undergo two or more recombination events to form a recombined polynucleotide that encodes an immunoglobulin heavy chain polypeptide, and thereby generating structural diversity in one or a plurality of immunoglobulin $V_H$ region genes.

18. The method of claim 17 wherein the recombination events result in formation of a recombined polynucleotide that encodes an immunoglobulin heavy chain polypeptide having a membrane anchor domain.

19. The method of claim 17, wherein the step of maintaining the isolated host cell comprises maintaining under conditions and for a time sufficient for expression of the immunoglobulin heavy chain polypeptide.

20. The method of claim 17 wherein less than one of said recombination events occurs per cell cycle of the isolated host cell.

21. The method of claim 19 comprising, prior to the step of maintaining, expanding the isolated host cell to obtain a plurality of host cells that are capable of immunoglobulin gene rearrangement and that comprise at least one chromosomally integrated tripartite recombination substrate.

22. The method of claim 21 wherein the at least one chromosomally integrated tripartite recombination substrate is under control of at least one operably linked recombination control element.

23. The method of claim 22 wherein the recombination control element is an inducible recombination control element.

24. The method of claim 23 wherein the inducible recombination control element is tightly regulated.

25. The method of claim 19 further comprising, prior to the step of maintaining, expanding the isolated host cell to obtain a plurality of isolated host cells that are capable of immunoglobulin gene rearrangement and that comprise at least one chromosomally integrated tripartite recombination substrate, wherein the at least one chromosomally integrated tripartite recombination substrate is under control of at least one operably linked recombination control element that is an inducible recombination control element, and wherein the step of maintaining comprises contacting the plurality of isolated host cells with a recombination inducer.

26. The method of claim 17 wherein the isolated host cell that is capable of immunoglobulin gene rearrangement is selected from the group consisting of:

(a) an isolated host cell that is capable of dividing without immunoglobulin gene rearrangement occurring;

(b) an isolated host cell that can be induced to express one or more recombination control elements selected from a RAG-1 gene and a RAG-2 gene; and (c) an isolated host cell that expresses first and second recombination control elements that comprise, respectively, a RAG-1 gene, and a RAG-2 gene, wherein expression of at least one of said recombination control elements by the host cell can be substantially impaired.

27. The isolated host cell of claim 2, wherein the isolated host cell further comprises a second nucleic acid composition for generating immunoglobulin light chain structural diversity which comprises:

(a) a fifth nucleic acid that comprises one or a plurality of mammalian immunoglobulin light chain variable ($V_L$) region genes each operably linked to an expression control sequence, each $V_L$ region gene consisting essentially of (i) an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence;
- (b) a sixth nucleic acid that comprises one or a plurality of mammalian immunoglobulin heavy chain diversity (D) segment genes, each of said immunoglobulin D segment genes consisting essentially of (i) an isolated D segment encoding polynucleotide sequence, (ii) a D segment upstream recombination signal sequence that is located 5' to each of said isolated D segment encoding polynucleotide sequences and that is capable of functional recombination with the non-endogenous $V_L$, region recombination signal sequence, and (iii) a D segment downstream recombination signal sequence that is located 3' to each of said isolated D segment encoding polynucleotide sequences; and
- (c) a seventh nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to an immunoglobulin light chain constant ($C_L$) region gene, and (ii) a non-endogenous $J_L$ segment recombination signal sequence that is located 5' to the isolated $J_L$ segment encoding polynucleotide sequence and that is capable of functional recombination with the D segment downstream recombination signal sequence of (b);

wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having an immunoglobulin $V_L$ region, an immunoglobulin $J_L$ segment, and an immunoglobulin $C_L$ region, and wherein the isolated host cell expresses said immunoglobulin light chain polypeptide.

28. The isolated host cell of claim 2, wherein the isolated host cell further comprises a second nucleic acid composition for generating immunoglobulin light chain structural diversity which comprises:
- (a) a fifth nucleic acid that comprises one or a plurality of mammalian immunoglobulin light chain variable ($V_L$) region genes each operably linked to an expression control sequence, each $V_L$ region gene consisting essentially of (i) an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence;
- (b) a sixth nucleic acid that comprises one or a plurality of mammalian immunoglobulin heavy chain diversity (D) segment genes, each of said immunoglobulin D segment genes consisting essentially of (i) an isolated D segment encoding polynucleotide sequence, (ii) a D segment upstream recombination signal sequence that is located 5' to each of said isolated D segment encoding polynucleotide sequences and that is capable of functional recombination with the non-endogenous $V_L$ region recombination signal sequence, and (iii) a D segment downstream recombination signal sequence that is located 3' to each of said isolated D segment encoding polynucleotide sequences; and
- (c) a seventh nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to either a specific protein-protein association domain encoding polynucleotide or a membrane anchor domain encoding polynucleotide, and (ii) a non-endogenous $J_L$ segment recombination signal sequence that is located 5' to the $J_L$ segment encoding polynucleotide sequence and that is capable of functional recombination with the D segment downstream recombination signal sequence of (b), wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having (i) an immunoglobulin $V_L$ region, (ii) an immunoglobulin $J_L$ segment and (iii) either a specific protein-protein association domain or a membrane anchor domain, and wherein the isolated host cell expresses said immunoglobulin light chain polypeptide.

29. The isolated host cell of claim 2, wherein the isolated host cell further comprises a second nucleic acid composition for generating immunoglobulin light chain structural diversity which comprises:
- (a) a fifth nucleic acid that comprises one or a plurality of mammalian immunoglobulin light chain variable ($V_L$) region genes each operably linked to an expression control sequence, each $V_L$ region gene consisting essentially of (i), an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence; and
- (b) a sixth nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to an immunoglobulin light chain constant ($C_L$) region gene, and (ii) a non-endogenous $J_L$ segment recombination signal sequence that is located 5' to the isolated $J_L$ segment encoding polynucleotide sequence and that is capable of functional recombination with the non-endogenous $V_L$ region recombination signal sequence of (b);

wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having an immunoglobulin $V_L$ region, an immunoglobulin $J_L$ segment, and an immunoglobulin $C_L$ region, and wherein the isolated host cell expresses said immunoglobulin light chain polypeptide.

30. The isolated host cell of claim 2, wherein the isolated host cell further comprises a second nucleic acid composition for generating immunoglobulin light chain structural diversity which comprises:
- (a) a fifth nucleic acid that comprises one or a plurality of mammalian immunoglobulin light chain variable ($V_L$) region genes each operably linked to an expression control sequence, each $V_L$ region gene consisting essentially of (i) an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence; and (b) a sixth nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to either a specific protein-protein association domain encoding polynucleotide or a membrane anchor domain encoding polynucleotide, and (ii) a non-endogenous $J_L$ segment recombination signal sequence that is located 5' to the isolated $J_L$ segment encoding polynucleotide sequence and that is capable of functional recombination with the non-endogenous $V_L$ region recombination signal sequence of (b), wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having (i) an immunoglobulin $V_L$ region, (ii) an immunoglobulin $J_L$ segment and (iii) either a specific protein-protein association domain or a membrane anchor domain, and wherein the isolated host cell expresses said immunoglobulin light chain polypeptide.

31. The isolated host cell of claim 1, wherein the isolated host cell further comprises a second nucleic acid composition for generating immunoglobulin light chain structural diversity which comprises:

(a) a fifth nucleic acid that comprises one or a plurality of mammalian immunoglobulin light chain variable ($V_L$) region genes each operably linked to an expression control sequence, each $V_L$ region gene consisting essentially of (i) an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence; and (b) a sixth nucleic acid that comprises one or a plurality of mammalian immunoglobulin heavy chain diversity (D) segment genes, each of said immunoglobulin D segment genes consisting essentially of (i) an isolated D segment encoding polynucleotide sequence, (ii) a D segment upstream recombination signal sequence that is located 5' to each of said isolated D segment encoding polynucleotide sequences and that is capable of functional recombination with the non-endogenous $V_L$ region recombination signal sequence, and (iii) a D segment downstream recombination signal sequence that is located 3' to each of said isolated D segment encoding polynucleotide sequences; and (c) a seventh nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to either a specific protein-protein association domain encoding polynucleotide or a membrane anchor domain encoding polynucleotide, and (ii) a non-endogenous $J_L$ segment recombination signal sequence that is located 5' to the isolated $J_L$ segment encoding polynucleotide sequence and that is capable of functional recombination with the D segment downstream recombination signal sequence of (b), wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having (i) an immunoglobulin $V_L$ region, (ii) an immunoglobulin $J_L$ segment and (iii) either a specific protein-protein association domain or a membrane anchor domain, and wherein the isolated host cell expresses said immunoglobulin light chain polypeptide.

32. The isolated host cell of claim 1, wherein the isolated host cell further comprises a second nucleic acid composition for generating immunoglobulin light chain structural diversity which comprises:

(a) a fifth nucleic acid that comprises one or a plurality of mammalian immunoglobulin light chain variable ($V_L$) region genes each operably linked to an expression control sequence, each $V_L$ region gene consisting essentially of (i) an isolated immunoglobulin $V_L$ region encoding polynucleotide sequence, and (ii) a non-endogenous $V_L$ region recombination signal sequence that is located 3' to the isolated immunoglobulin $V_L$ region encoding polynucleotide sequence; and (b) a sixth nucleic acid that comprises one or a plurality of mammalian immunoglobulin light chain joining ($J_L$) segment genes, each of said immunoglobulin $J_L$ segment genes consisting essentially of (i) an isolated $J_L$ segment encoding polynucleotide sequence in operable linkage to either a specific protein-protein association domain encoding polynucleotide or a membrane anchor domain encoding polynucleotide, and (ii) a non-endogenous $J_L$ segment recombination signal sequence that is located 5' to the isolated $J_L$ segment encoding polynucleotide sequence and that is capable of functional recombination with the non-endogenous $V_L$ region recombination signal sequence of (b), wherein the second nucleic acid composition is integrated in the isolated host cell and wherein the second nucleic acid composition for generating immunoglobulin light chain diversity can undergo at least two or more recombination events in any order in the isolated host cell to form a recombined polynucleotide that encodes an immunoglobulin light chain polypeptide having (i) an immunoglobulin $V_L$ region, (ii) an immunoglobulin $J_L$ segment and (iii) either a specific protein-protein association domain or a membrane anchor domain, and wherein the isolated host cell expresses said immunoglobulin light chain polypeptide.

33. The isolated host cell of any one of claims 28, 31 and 32 wherein the protein-protein association domain is selected from the group consisting of a mammalian immunoglobulin light chain ($C_L$) constant region, an RGD-containing polypeptide that is capable of integrin binding, a lipid raft-associating polypeptide domain, and a heterodimer-promoting polypeptide domain.

34. The isolated host cell of claim 33 wherein the mammalian immunoglobulin light chain ($C_L$) constant region is selected from a kappa constant region and a lambda constant region.

35. The isolated host cell of claim 28 wherein at least one mammalian immunoglobulin heavy chain diversity (D) segment gene comprises one or a plurality of artificial D gene segments.

36. The isolated host cell of claim 27 wherein the fifth, sixth and seventh isolated nucleic acids are joined in operable linkage as a single nucleic acid molecule.

37. The isolated host cell of claim 27 wherein the second nucleic acid composition comprises a vector which comprises the fifth, sixth and seventh isolated nucleic acids joined in operable linkage.

38. The isolated host cell of any one of claims 27-30 wherein the second nucleic acid composition is selected from the group consisting of a viral vector, a plasmid, a cosmid, a transposon and an artificial chromosome.

39. The isolated host cell of claim 27 wherein the mammalian immunoglobulin $V_L$ gene is selected from the group consisting of a human $V_L$ gene, a mouse $V_L$ gene, a rat $V_L$ gene, a rabbit $V_L$ gene, a canine $V_L$ gene, a feline $V_L$ gene, an equine $V_L$ gene, a bovine $V_L$ gene, a monkey $V_L$ gene, a baboon $V_L$ gene, a macaque $V_L$ gene, a chimpanzee $V_L$, gene, a gorilla $V_L$ gene, an orangutan $V_L$ gene, and an ovine $V_L$ gene.

40. The isolated host cell of claim 27 wherein the second isolated nucleic acid composition for generating immunoglobulin light chain structural diversity is under control of at least one operably linked recombination control element.

41. The isolated host cell of claim 40 wherein the recombination control element is an inducible recombination control element.

42. The isolated host cell of claim 41 wherein the inducible recombination control element is tightly regulated.

43. The isolated host cell according to any one of claims 1, 2, 27 and 31 that is genetically engineered to express a mammalian RAG-1 gene, a mammalian RAG-2 gene and a mammalian TdT gene, or a fragment thereof that encodes a protein that is capable of mediating immunoglobulin gene rearrangement and junctional diversity.

44. The isolated host cell of claim 43 in which expression of one or more of the mammalian RAG-1 gene, mammalian RAG-2 gene and mammalian TdT gene, or a fragment thereof that encodes a protein that is capable of mediating immunoglobulin gene rearrangement and junctional diversity, is inducible expression.

* * * * *